(12) United States Patent
Draghia-Akli et al.

(10) Patent No.: US 7,338,656 B2
(45) Date of Patent: Mar. 4, 2008

(54) COMPOSITION AND METHOD TO ALTER LEAN BODY MASS AND BONE PROPERTIES IN A SUBJECT

(75) Inventors: Ruxandra Draghia-Akli, Houston, TX (US); Robert J. Schwartz, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 517 days.

(21) Appl. No.: 10/281,067

(22) Filed: Oct. 25, 2002

(65) Prior Publication Data

US 2004/0138111 A1 Jul. 15, 2004

Related U.S. Application Data

(60) Provisional application No. 60/357,808, filed on Oct. 26, 2001.

(51) Int. Cl.
*A61K 48/00* (2006.01)
*A01N 63/00* (2006.01)
(52) U.S. Cl. .................................... 424/93.2
(58) Field of Classification Search ............... 424/93.2
See application file for complete search history.

(56) References Cited

U.S. PATENT DOCUMENTS

| | | |
|---|---|---|
| 4,223,019 A | 9/1980 | Momany |
| 4,223,020 A | 9/1980 | Momany |
| 4,223,021 A | 9/1980 | Momany |
| 4,224,316 A | 9/1980 | Momany |
| 4,226,857 A | 10/1980 | Momany |
| 4,228,156 A | 10/1980 | Momany |
| 4,228,158 A | 10/1980 | Momany |
| 4,410,512 A | 10/1983 | Bowers |
| 4,684,611 A | 8/1987 | Schilperoort |
| 4,833,166 A | 5/1989 | Grosvenor |
| 4,839,344 A | 6/1989 | Bowers |
| 4,952,500 A | 8/1990 | Finnerty |
| 4,956,288 A | 9/1990 | Barsoum |
| 5,023,322 A | 6/1991 | Kovacs |
| 5,036,045 A | 7/1991 | Thorner |
| RE33,699 E | 9/1991 | Drengler |
| 5,061,690 A | 10/1991 | Kann |
| 5,084,442 A | 1/1992 | Felix |
| 5,134,120 A | 7/1992 | Boyd |
| 5,137,872 A | 8/1992 | Seely |
| 5,292,721 A | 3/1994 | Boyd |
| 5,302,523 A | 4/1994 | Coffee |
| 5,322,783 A | 6/1994 | Tomes |
| 5,384,253 A | 1/1995 | Krzyzek |
| 5,439,440 A | 8/1995 | Hofmann |
| 5,464,765 A | 11/1995 | Coffee |
| 5,486,505 A | 1/1996 | Bowers |
| 5,538,877 A | 7/1996 | Lundquist |
| 5,538,880 A | 7/1996 | Lundquist |
| 5,550,318 A | 8/1996 | Adams |
| 5,563,055 A | 10/1996 | Townsend |
| 5,580,859 A | 12/1996 | Felgner |
| 5,589,466 A | 12/1996 | Felgner |
| 5,591,616 A | 1/1997 | Hiei |
| 5,610,042 A | 3/1997 | Chang |
| 5,656,610 A | 8/1997 | Shuler |
| 5,696,089 A | 12/1997 | Felix |
| 5,702,384 A | 12/1997 | Umeyama |
| 5,702,932 A | 12/1997 | Hoy |
| 5,704,908 A | 1/1998 | Hofmann |
| 5,736,524 A | 4/1998 | Content |
| 5,756,264 A | 5/1998 | Schwartz |
| 5,776,901 A | 7/1998 | Bowers |
| 5,780,448 A | 7/1998 | Davis |
| 5,789,215 A | 8/1998 | Berns |
| 5,792,747 A | 8/1998 | Schally |
| 5,846,936 A | 12/1998 | Felix |
| 5,847,066 A | 12/1998 | Coy |
| 5,874,534 A | 2/1999 | Vegeto |
| 5,935,934 A | 8/1999 | Vegeto |
| 5,945,100 A | 8/1999 | Fick |
| 5,981,274 A | 11/1999 | Tyrrell |
| 5,994,624 A | 11/1999 | Trolinder |
| 6,165,755 A | 12/2000 | Sherwood et al. |
| 6,423,693 B1 | 7/2002 | Schwartz et al. |
| 6,486,134 B2 * | 11/2002 | Lee et al. ............... 514/44 |
| 6,759,393 B1 * | 7/2004 | Morsey et al. ............ 514/44 |
| 2004/0192593 A1 * | 9/2004 | Draghia-Akli et al. ..... 514/12 |

FOREIGN PATENT DOCUMENTS

| | | |
|---|---|---|
| WO | WO 94/09699 | 5/1994 |
| WO | WO- 95/06128 | 3/1995 |
| WO | WO 99/05300 | 2/1999 |
| WO | WO 01/06988 | 2/2001 |
| WO | WO 01/06988 A2 | 2/2001 |
| WO | WO 01/21801 A1 | 3/2001 |
| WO | WO 01/66149 A2 | 9/2001 |
| WO | WO 02/061037 A2 | 8/2002 |
| WO | WO 04/018697 A2 | 3/2004 |

OTHER PUBLICATIONS

Anderson et al., Nature, vol. 392, pp. 25-30, 1998.*

(Continued)

*Primary Examiner*—Brian Whiteman
(74) *Attorney, Agent, or Firm*—Pepper Hamilton LLP

(57) ABSTRACT

A method for decreasing the body fat proportion, increasing lean body mass, increasing bone density, or improving the rate of bone healing, or all, of a subject. Embodiments of the invention include delivering a heterologous nucleic acid sequence encoding GHRH or functional biological equivalent thereof into the cells of the subject and allowing expression of the encoded gene to occur while the modified cells are within the subject.

55 Claims, 18 Drawing Sheets

OTHER PUBLICATIONS

Verma, Nature, vol. 389, pp. 239-242, 1997.*

Romano et al. Stem Cells, 18:19-39, 2000.*

Fenske et al., 2001, Current Opnion in Molecular Therapeutics, 3: 153-158.*

Abruzzese, R. V., D. Godin, M. Burcin, V. Mehta, M. French, Y. Li, B. W. O'Malley, and J. L. Nordstrom. 1999. Ligand-dependent regulation of plasmid-based transgene expression in vivo. Hum. Gene Ther. 10:1499-1507.

Abruzzese, R. V., D. Godin, V. Mehta, J. L. Perrard, M. French, W. Nelson, G. Howell, M. Coleman, B. W. O'Malley, and J. L. Nordstrom. 2000. Ligand-dependent regulation of vascular endothelial growth factor and erythropoietin expression by a plasmid-based autoinducible GeneSwitch system. Mol. Ther. 2:276-287.

Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bernabeu. 1996. Cloning of the human platelet endothelial cell adhesion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucleic Acids Res. 20:4795-4801.

Argente, J., J. Pozo, and J. A. Chowen. 1996. The growth hormone axis: control and effects. Hormone Research 45 Suppl 1:9-11.

Barr, E. and J. M. Leiden. 1991. Systemic delivery of recombinant proteins by genetically modified myoblasts. Science 254:1507-1509.

Bercu, B. B., R. F. Walker 1997. Growth Hormone Secretagogues In Children With Altered Growth. Acta Paediatrica 86:102-106.

Bergsma, D. J., J. M. Grichnik, L. M. Gossett, and R. J. Schwartz. 1986. Delimitation and characterization of cis-acting DNA sequences required for the regulated expression and transcriptional control of the chicken skeletal alpha-actin gene. Molecular & Cellular Biology 6:2462-2475.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Blethen, S. L. and A. C. Rundle. 1996. Slipped capital femoral epiphysis in children treated with growth hormone. A summary of the National Cooperative Growth Study experience. Horm. Res. 46:113-116.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Bureau, M. F., J. Gehl, V. Deleuze, L. M. Mir, and D. Scherman. 2000. Importance of association between permeabilization and electrophoretic forces for intramuscular DNA electrotransfer. Biochim. Biophys. Acta 1474:353-359.

Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U. S. A. 94:3596-3601.

Chen, C. and H. Okayama. 1987. High-efficiency transformation of mammalian cells by plasmid DNA. Mol. Cell Biol. 7:2745-2752.

Chevalier, R. L., S. Goyal, A. Kim, A. Y. Chang, D. Landau, and D. Leroith. 2000. Renal tubulointerstitial injury from ureteral obstruction in the neonatal rat is attenuated by IGF-1. Kidney Int. 57:882-890.

Cocea, L. 1997. Duplication of a region in the multiple cloning site of a plasmid vector to enhance cloning-mediated addition of restriction sites to a DNA fragment. Biotechniques 23:814-816.

Cohn, S. H., A. N. Vaswani, S. Yasumura, K. Yuen, and K. J. Ellis. 1984. Improved models for determination of body fat by in vivo neutron activation. Am. J Clin. Nutr. 40:255-259.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. Journal of Clinical Endocrinology & Metabolism 76:134-138.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. [Review]. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dhawan, J., L. C. Pan, G. K. Pavlath, M. A. Travis, A. M. Lanctot, and H. M. Blau. 1991. Systemic delivery of human growth hormone by injection of genetically engineered myoblasts. Science 254:1509-1512.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U. S. A 82:8325-8329.

Draghia-Akli, R., X. G. Li, and R. J. Schwartz. 1997. Enhanced growth by ectopic expression of growth hormone releasing hormone using an injectable myogenic vector. nature biotechnology 15:1285-1289.

Draghia-Akli, R., P. B. Malone, L. A. Hill, K. M. Ellis, R. J. Schwartz, and J. L. Nordstrom. 2002. Enhanced animal growth via ligand-regulated GHRH myogenic-injectable vectors. FASEB J. 16:426-428.

Dubreuil, P., Y. Couture, G. Pelletier, D. Petitclerc, L. Delorme, H. Lapierre, P. Gaudreau, J. Morisset, and P. Brazeau. 1990a. Effect of long-term administration of porcine growth hormone-releasing factor and(or) thyrotropin-releasing factor on growth hormone, prolactin and thyroxine concentrations in growing pigs. J. Anim Sci. 68:95-107.

Dubreuil, P., D. Petitclerc, G. Pelletier, P. Gaudreau, C. Farmer, Mowles, TF, and P. Brazeau. 1990b. Effect of dose and frequency of administration of a potent analog of human growth hormone-releasing factor on hormone secretion and growth in pigs. Journal of Animal Science 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. Journal of Clinical Endocrinology & Metabolism 75:1115-1120.

Evans, W. S., S. M. Anderson, L. T. Hull, P. P. Azimi, C. Y. Bowers, and J. D. Veldhuis. 2001, Continuous 24-hour intravenous infusion of recombinant human growth hormone (GH)-releasing hormone-(1-44)-amide augments pulsatile, entropic, and daily rhythmic GH secretion in postmenopausal women equally in the estrogen-withdrawn and estrogen-supplemented states. J. Clin. Endocrinol. Metab 86:700-712.

Evans, W. S., M. L. Vance, D. L. Kaiser, R. P. Sellers, J. L. Borges, T. R. Downs, L. A. Frohman, J. Rivier, W. Vale, and M. O. Thorner. 1985. Effects of intravenous, subcutaneous, and intranasal administration of growth hormone (GH)-releasing hormone-40 on serum GH concentrations in normal men. Journal of Clinical Endocrinology & Metabolism 61:846-850.

Fechheimer, M., J. F. Boylan, S. Parker, J. E. Sisken, G. L. Patel, and S. G. Zimmer. 1987. Transfection of mammalian cells with plasmid DNA by scrape loading and sonication loading. Proc. Natl. Acad. Sci. U. S. A. 84:8463-8467.

Fewell, J. G., F. Maclaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Frohman, L. A., T. R. Downs, E. P. Heimer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and . 1995. The insulin gene promoter. A simplified nomenclature. Diabetes 44:1002-1004.

Gesundheit, N. and J. K. Alexander. 1995. Endocrine Therapy with Recombinant Hormones and Growth Factors. In: B. D. Weintraub (Ed.) Molecular Endocrinology: Basic Concepts and Clinical Correlations. pp. 491-507. Raven Press,Ltd., New York.

Gilbert, R. A., M. J. Jaroszeski, and R. Heller. 1997. Novel electrode designs for electrochemotherapy. Biochim. Biophys. Acta 1334:9-14.

Gopal, T. V. 1985. Gene transfer method for transient gene expression, stable transformation, and cotransformation of suspension cell cultures. Mol. Cell Biol. 5:1188-1190.

Graham, F. L. and A. J. Van Der Eb. 1973. Transformation of rat cells by DNA of human adenovirus 5. Virology 54:536-539.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Hafez, I. M., N. Maurer, and P. R. Cullis. 2001. On the mechanism whereby cationic lipids promote intracellular delivery of polynucleic acids. Gene Ther. 8:1188-1196.

Hamm, A., N. Krott, I. Breibach, R. Blindt, and A. K. Bosserhoff. 2002. Efficient transfection method for primary cells. Tissue Eng 8:235-245.

Harland, R. and H. Weintraub. 1985. Translation of mRNA injected into Xenopus oocytes is specifically inhibited by antisense RNA. J. Cell Biol. 101:1094-1099.

Heller, R., M. J. Jaroszeski, L. F. Glass, J. L. Messina, D. P. Rapaport, R. C. Deconti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Horlick, R. A. and P. A. Benfield. 1989. The upstream muscle-specific enhancer of the rat muscle creatine kinase gene is composed of multiple elements. Mol. Cell Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell. Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Klamut, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell. Biol. 10:193-205.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lareyre, J. J. , T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Lee, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration of pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer. Res. 6:2829-2834.

Li, X., E. M. Eastman, R. J. Schwartz, and R. Draghia-Akli. 1999. Synthetic muscle promoters: activities exceeding naturally occurring regulatory sequences. nature biotechnology 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macejak, D. G. and P. Sarnow. 1991. Internal initiation of translation mediated by the 5' leader of a cellular mRNA. Nature 353:90-94.

Madry, H., R. Reszka, J. Bohlender, and J. Wagner. 2001. Efficacy of cationic liposome-mediated gene transfer to mesangial cells in vitro and in vivo. J. Mol. Med. 79:184-189.

Matsubara, H., Y, Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Mir, L. M., M. F. Bureau, J. Gehl, R. Rangara, D. Rouy, J. M. Caillaud, P. Delaere, D. Branellec, B. Schwartz, and D. Scherman. 1999. High-efficiency gene transfer into skeletal muscle mediated by electric pulses. Proc. Natl. Acad. Sci. U. S. A 96:4262-4267.

Morel, G., R. Gallego, L. Boulanger, E. Pintos, T. Garcia-Caballero, and P. Gaudreau. 1999. Restricted presence of the growth hormone-releasing hormone receptor to somatotropes in rat and human pituitaries. Neuroendocrinology 70:128-136.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., A. Nakamura, and H. M. Park. 1998. In vivo electroporation: A powerful and convenient means of nonviral gene transfer to tissues of living animals. Int. J. Mol. Med. 1:55-62.

Murray, R. A., H. G. Maheshwari, E. J. Russell, and G. Baumann. 2000. Pituitary hypoplasia in patients with a mutation in the growth hormone-releasing hormone receptor gene. AJNR Am. J Neuroradiol. 21:685-689.

Nabel, E. G., G. Plautz, F. M. Boyce, J. C. Stanley, and G. J. Nabel. 1989. Recombinant gene expression in vivo within endothelial cells of the arterial wall. Science 244:1342-1344.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhrmann, H. Liang, M. Oakley, A. Taye, B. K. Sim, and S. L. Hoffman. 2001. Codon optimization of gene fragments encoding *Plasmodium falciparum* merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potrykus, I., J. Paszkowski, M. W. Saul, J. Petruska, and R. D. Shillito. 1985. Molecular and general genetics of a hybrid foreign gene introduced into tobacco by direct gene transfer. Mol. Gen. Genet. 199:169-177.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U. S. A. 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. Journal of Molecular & Cellular Cardiology 26:1393-1401.

Raghavachari, N. and W. E. Fahl. 2002. Targeted gene delivery to skin cells in vivo: a comparative study of liposomes and polymers as delivery vehicles. J. Pharm. Sci. 91:615-622.

Rippe, R. A., D. A. Brenner, and H. L. Leffert. 1990. DNA-mediated gene transfer into adult rat hepatocytes in primary culture. Mol. Cell Biol. 10:689-695.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10:187-192.

Smith, L. C. and J. L. Nordstrom. 2000. Advances in plasmid gene delivery and expression in skeletal muscle. Curr. Opin. Mol. Ther. 2:150-154.

Somiari, S., J. Glasspool-Malone, J. J. Drabick, R. A. Gilbert, R. Heller, M. J. Jaroszeski, and R. W. Malone. 2000. Theory and in vivo application of electroporative gene delivery. Mol. Ther. 2:178-187.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Thorner, M. O., M. L. Vance, W. S. Evans, A. D. Rogol, J. Rivier, W. Vale, Blizzard, and RM. 1986. Clinical Studies With GHRH in Man. Hormone Research 24:91-98.

Thorner, M. O., M. L. Vance, M. L. Hartman, R. W. Holl, W. S. Evans, J. D. Veldhuis, E. Van Cauter, G. Copinschi, and C. Y. Bowers. 1990. Physiological role of somatostatin on growth hormone regulation in humans. Metabolism: Clinical & Experimental 39:40-42.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Toner, M. S., R. H. King, F. R. Dunshea, H. Dove, and C. S. Atwood. 1996. The effect of exogenous somatotropin on lactation performance of first-litter sows. J. Anim Sci. 74:167-172.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2(XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, ansd J. M. Isner. 1996. Direct intramuscular gene transfer of naked DNA encoding vascular endothelial growth factor augments collateral development and tissue perfusion [see comments]. Circulation 94:3281-3290.

Tur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell. Biol. 6:716-718.

Vance, M. L. 1990. Growth-hormone-releasing hormone. [Review] [52 refs]. Clinical Chemistry 36:415-420.

Vance, M. L., D. L. Kaiser, W. S. Evans, R. Furlanetto, W. Vale, J. Rivier, and M. O. Thorner. 1985a. Pulsatile growth hormone secretion in normal man during a continuous 24-hour infusion of human growth hormone releasing factor (1-40). Evidence for intermittent somatostatin secretion. J. Clin. Invest. 75:1584-1590.

Vance, M. L., D. L. Kaiser, W. S. Evans, M. O. Thorner, R. Furlanetto, J. Rivier, W. Vale, G. Perisutti, and L. A. Frohman. 1985B. Evidence for a limited growth hormone (GH)-releasing hormone (GHRH)-releasable quantity of GH: effects of 6-hour infusions of GHRH on GH secretion in normal man. Journal of Clinical Endocrinology & Metabolism 60:370-375.

Vegeto, E., G. F. Allan, W. T. Schrader, M. J. Tsai, D. P. McDonnell, and B. W. O'Malley. 1992. The mechanism of RU486 antagonism is dependent on the conformation of the carboxy-terminal tail of the human progesterone receptor. Cell 69:703-713.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two years of replacement therapy in adults with growth hormone deficiency. Clin. Endocrinol. (Oxf) 47:485-494.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wiethoff, C. M., J. G. Smith, G. S. Koe, and C. R. Middaugh. 2001. The potential role of proteoglycans in cationic lipid-mediated gene delivery. Studies of the interaction of cationic lipid-DNA complexes with model glycosaminoglycans. J. Biol. Chem. 276:32806-32813.

Wilson, J. M., L. K. Birinyi, R. N. Salomon, P. Libby, A. D. Callow, and R. C. Mulligan. 1989. Implantation of vascular grafts lined with genetically modified endothelial cells. Science 244:1344-1346.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wu, G. Y. and C. H. Wu. 1988A. Evidence for targeted gene delivery to Hep G2 hepatoma cells in vitro. Biochemistry 27:887-892.

Wu, G. Y. and C. H. Wu. 1988B. Receptor-mediated gene delivery and expression in vivo. J. Biol. Chem. 263:14621-14624.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Xu, J., Z. Nawaz, S. Y. Tsai, M. J. Tsai, and B. W. O'Malley. 1996. The extreme C terminus of progesterone receptor contains a transcriptional repressor domain that functions through a putative corepressor. Proc. Natl. Acad. Sci. USA 93:12195-12199.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

U.S. Appl. No. 10/021,403, Apr. 1, 2003, Schwartz et al.

Bohlen,P., Esch,F., Brazeau,P., Ling,N., and Guillemin,R. (1983). Isolation and characterization of the porcine hypothalamic growth hormone releasing factor. Biochem. Biophys. Res. Commun. 116, 726-734.

Draghia-Akli,R., Fiorotto,M.L., Hill,L.A., Malone,P.B., Deaver,D.R., and Schwartz,R.J. (1999). Myogenic expression of an injectable protease-resistant growth hormone-releasing hormone augments long-term growth in pigs. Nat. Biotechnol. 17, 1179-1183.

Iranmanesh A, South S, Liem AY, Clemmons D, Thorner MO, Weltman A, Veldhuis JD., "Unequal impact of age, percentage body fat, and serum testosterone concentrations on the somatotrophic, IGF-I, and IGF-binding protein responses to a three-day intravenous growth hormone-releasing hormone pulsatile infusion in men." Eur J Endocrinol. Jul. 1998;139(1):59-71.

Gonzalez L. et al., Up-regulation of GH-binding protein by mouse GH in transgenic mice overexpressing GH-releasing hormone. Journal of endocrinology, Nov. 1999, vol. 163, No. 2, pp. 299-307.

Kovacs, M et al., Effects of antagonists of growth hormone-releasing hormone on GH and insulin-like growth factor I levels in transgenic mice oerexpressing the human GHRH gene, and animal model of acromegaly. Endocrinology Nov. 1997, vol. 138, No. 11, pp. 4536-4542.

Wojtkiewicz PW, Phelps CJ, Hurley Dlworjte, "Transcript abundance in mouse pituitaries with altered growth hormone expression quantified by reverse transcriptase polymerase chain reaction implicates transcription factor ZN-16 in gene regulation in vivo." Endocrine. Jun. 2002;18(1):67-74.

Enright WJ, Prendiville DJ, Spicer LJ, Stricker PR, Moloney AP, Mowles TF, Campbell RM. Effects of growth hormone-releasing factor and(or) thyrotropin-releasing hormone on growth, feed efficiency, carcass characteristics, and blood hormones and metabolites in beef heifers. J Anim Sci. Sep. 1993;71(9):2395-405. XP002401644. Abstract only.

Moellers RF, Cogburn LA. Pulsatile infusion of growth hormone-releasing factor depresses growth of young broiler chickens. Comp Biochem Physiol Comp Physiol. Apr. 1994;107(4):665-72. XP002401645. Abstract only.

Draghia-Akli R, Fiorotto MI., Hill LA, Malone PB, Deaver DR, Schwartz RJ. Myogenic expression of an injectable protease-resistant growth hormone-releasing hormone augments long-term growth in pigs. Nat Biotechnol. Dec. 1999;17(12):1179-83.

Dubreuil P, Abribat T, Broxup B, Brazeau P. Long-term growth hormone-releasing factor administration on growth hormone, insulin-like growth factor-I concentrations, and bone healing in the Beagle. Can J Vet Res. Jan. 1996;60(1):7-13.

* cited by examiner

Figure 1

| Sequence | Name |
|---|---|
| YADAIFTNSYRKVLGQLSARKLLQDIMSRQQGERNQEQGA-OH | porcine wild-type (SeqID No.:10) |
| HVDAIFTNSYRKVLAQLSARKLLQDILNRQQGERNQEQGA-OH | HV-GHRH (SeqID No.: 1) |
| YIDAIFTNSYRKVLAQLSARKLLQDILNRQQGERNQEQGA-OH | TI-GHRH (SeqID No.: 2) |
| YVDAIFTNSYRKVLAQLSARKLLQDILNRQQGERNQEQGA-OH | TV-GHRH (SeqID No.: 3) |
| YADAIFTNSYRKVLAQLSARKLLQDILNRQQGERNQEQGA-OH | 15/27/28-GHRH (SeqID No.: 4) |

COMPOSITION AND METHOD TO ALTER LEAN BODY MASS AND BONE PROPERTIES IN A SUBJECT

RELATED APPLICATIONS

This application claims priority to U.S. Provisional Patent Application Ser. No. 60/357,808 entitled "increase Body mass, decrease body fat proportion, increase bone density and improve bone healing rate," filed on Oct. 26, 2001, the entire content of which is hereby incorporated by reference.

BACKGROUND

The present invention pertains to compositions and methods for plasmid-mediated gene supplementation. The present invention relates to a method of decreasing body fat proportions and increasing lean body mass ("LBM") in an animal subject. Overall, the embodiments of the invention can be accomplished by delivering a nucleic acid expression construct that encodes a GHRH or functional biological equivalent thereof into a tissue of a subject and allowing expression of the encoded gene in the subject. For example, when such a nucleic acid sequence is delivered into the specific cells of the subject tissue specific constitutive expression is achieved. Furthermore, external regulation of the GHRH or functional biological equivalent thereof gene can be accomplished by utilizing inducible promoters that are regulated by molecular switch molecules, which are given to the subject. The preferred method to deliver the constitutive or inducible nucleic acid encoding sequences of GHRH or the functional biological equivalents thereof is directly into the cells of the subject by the process of in vivo electroporation. In addition, this invention also relates to a method of increasing bone density and improvising the rate of bone healing in an animal subject. More specifically, this invention pertains to both an in vivo and an ex vivo method for delivering a heterologous nucleic acid sequence encoding growth hormone releasing hormone "GHRH" or functional biological equivalent thereof into the cells of the subject and allowing expression of the encoded gene to occur while the modified cells are within the subject. Another embodiment of the present invention relates to regulating the expression of the GHRH using a molecular switch (e.g. mifepistone).

Growth Hormone ("GH") and Immune Function: The central role of growth hormone ("GH") in controlling somatic growth in humans and other vertebrates, and the physiologically relevant pathways regulating GH secretion from the pituitary are well known. The GH production pathway is composed of a series of interdependent genes whose products are required for normal growth. The GH pathway genes include: (1) ligands, such as GH and insulin-like growth factor-I ("IGF-I"); (2) transcription factors such as prophet of pit 1, or prop 1, and pit 1: (3) agonists and antagonists, such as growth hormone releasing hormone ("GHRH") and somatostatin ("SS"), respectively, and (4) receptors, such as GHRH receptor ("GHRH-R") and the GH receptor ("GH-R"). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism GH synthesis and secretion from the anterior pituitary is stimulated by GHRH and inhibited by somatostatin, both hypothalamic hormones. GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

The principal feature of GH deficiencies in children is short stature. Similar phenotypes are produced by genetic defects at different points in the GH axis, as well as non-GH-deficient short stature. Non-GH-deficiencies have different etiology, such as: (1) genetic diseases, Turner syndrome, hypochondroplasia; and (2) chronic renal insufficiency. Cases where the GH axis is unaffected (i.e., patients have normal hormones, genes and receptors) account for more than 50% of the total cases of growth retardation. In these cases GHRH and GH therapy has been shown to be effective (Gesundheit and Alexander, 1995).

Reduced GH secretion from the anterior pituitary causes skeletal muscle mass to be lost during aging from 25 years to senescence. The GHRH-GH-IGF-I axis undergoes dramatic changes through aging and in the elderly with decreased GH production rate and GH half-life, decreased IGF-I response to GH and GHRH stimuli leads to loss of skeletal muscle mass (sarcopenia), osteoporosis, and increase in fat and decrease in lean body mass. Previous studies have shown that in elderly the level of GH secretion is significant reduced by 70-80% of teenage level. It has been demonstrated that the development of sarcopenia can be offset by exogenous GH therapy. However, this remains a controversial therapy in the elderly because of its cost and frequent side effects.

The production of recombinant proteins allows a useful tool for the treatment of these conditions. Although GH replacement therapy is widely used in patients with growth deficiencies and provides satisfactory growth, and may have positive psychological effects on the children being treated, this therapy has several disadvantages, including an impractical requirement for frequent administration of GH and undesirable secondary effects.

GH is released in a distinctive pulsatile pattern that has profound importance for its biological activity (Argente et al., 1996). Secretion of GH is stimulated by the natural GH secretagogue, GHRH, and inhibited by somatostatin (SS), and both hypothalamic hormones (Thorner et al., 1990). GH pulses are a result of GHRH secretion that is associated with a diminution or withdrawal of somatostatin secretion. In addition, the pulse generator mechanism is timed by GH-negative feedback The endogenous rhythm of GH secretion becomes entrained to the imposed rhythm of exogenous GH administration. Effective and regulated expression of the GH and insulin-like growth factor I ("IGF-I") pathway is essential for optimal linear growth, homeostasis of carbohydrate, protein, and fat metabolism, and for providing a positive nitrogen balance (Murray and Shalet, 2000). Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (Dubreuil et al., 1990a; Vance et al., 1985b; Vance, 1990; Vance et al., 1985a). Thus, GHRH recombinant protein treatment may be more physiologically relevant than GH therapy. However, due to the short half-life of GHRH in vivo, frequent (one to three times per day intravenous, subcutaneous or intranasal (requiring 300-fold higher dose) administrations are necessary (Evans et al., 2001; Thorner et al., 1986). Thus, as a chronic therapy, recombinant GHRH protein administration is not practical.

Extracranially secreted GHRH, as mature peptide or truncated molecules (as seen with pancreatic islet cell tumors and variously located carcinoids) are often biologically active and can even produce acromegaly (Thorner et al., 1984). Administration of recombinant GHRH to GH-deficient children or adult humans augments IGF-I levels, increases GH secretion proportionally to the GHRH dose, yet still invokes a response to bolus doses of GHRH (Bercu et al., 1997). Thus, GHRH administration represents a more physiological alternative of increasing subnormal GH and IGF-I levels (Corpas et al., 1993).

Although GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical. Extracranially secreted GHRH, as processed protein species GHRH(1-40) hydroxy or GHRH(1-44) amide or even as shorter truncated molecules, are biological active (Thorner et al., 1984). It has been reported that a low level of GHRH (100 pg/ml) in the blood supply stimulates GH secretion (Corpas et al., 1993). Direct plasmid DNA gene transfer is currently the basis of many emerging therapy strategies and thus does not require viral genes or lipid particles (Aihara and Miyazaki, 1998; Muramatsu et al., 1998). Skeletal muscle is target tissue, because muscle fiber has a long life span and can be transduced by circular DNA plasmids that express over months or years in an immunocompetent host (Davis et al., 1993; Tripathy et al., 1996). Previous reports demonstrated that human GHRH cDNA could be delivered to muscle by an injectable myogenic expression vector in mice where it transiently stimulated GH secretion to a modes extent over a period of two weeks (Draghia-Akli et al., 1997).

Wild type GHRH has a relatively short half-life in the circulatory system, both in humans (Frohman et al., 1984) and in farm animals. After 60 minutes of incubation m plasma 95% of the GHRH(1-44)NH2 is degraded, while incubation of the shorter (1-40)OH form of the hormone, under similar conditions, shows only a 77% degradation of the peptide after 60 minutes of incubation (Frohman et al., 1989). Incorporation of cDNA coding for a particular protease-resistant GHRH analog in a therapeutic nucleic acid vector results in a molecule with a longer half-life in serum, increased potency, and provides greater GH release in plasmid-injected animals (Draghia-Akli et al., 1999), herein incorporated by reference). Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors (Draghia-Akli et al., 1999).

Administering novel GHRH analog proteins (U.S. Pat. Nos. 5,847,066; 5846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833,166; 4,228,158; 4,228,156; 4,226,857; 4,224,316; 4,223,021; 4,223,020; 4,223,019) for the purpose of increasing release of growth hormone have been reported. A GHRH analog containing the following mutations has been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. patent application Ser. No. 09/624,268 (now U.S. Pat. No. 6,551,996) ("the '268 patent application"), which teaches application of a GHRH analog containing mutations that improve the ability to elicit the release of growth hormone. In addition, the '268 patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference. In the embodiments of the '268 patent application and specific embodiments herein, the mutated GHRH-encoding molecules lack the Gln, Ser or Thr mutations of the Asn at position 8.

U.S. Pat. No. 5,061,690 is directed toward increasing both birth weight and milk production by supplying to pregnant female mammals an effective amount of human GHRH or one of it analogs for 10-20 days. Application of the analogs lasts only throughout the lactation period. However, multiple administrations are presented, and there is no disclosure regarding administration of the growth hormone releasing hormone (or factor) as a DNA molecule, such as with plasmid mediated supplementation techniques.

U.S. Pat. Nos. 5,134,120 ("the '120 patent") and 5,292,721 ("the '721 patent") teach that by deliberately increasing growth hormone in swine during the last 2 weeks of pregnancy through a 3 week lactation resulted in the newborn piglets having marked enhancement of the ability to maintain plasma concentrations of glucose and free fatty acids when fasted after birth. In addition, the '120 and '721 patents teaches that treatment of the sow during lactation results in increased milk fat in the colostrum and an increased milk yield. These effects are important in enhancing survivability of newborn pigs and weight gain prior to weaning. However the '120 and '721 patents provide no teachings regarding administration of the growth hormone releasing hormone as a DNA form In contrast to protein therapy, nucleic acid transfer delivers polynucleotides to somatic tissue in a manner that, in some embodiments, can correct inborn or acquired deficiencies and imbalances. In other embodiments, vectors such as plasmids are used to supplement basal levels of an expressed endogenous gene product. Gene-based drug delivery offers a number of advantages over the administration of recombinant proteins. These advantages include the conservation of native protein structure, improved biological activity, avoidance of systemic toxicities, and avoidance of infectious and toxic impurities. In addition, nucleic acid transfer, for therapeutic purposes, and plasmid-mediated supplementation of an endogenous gene product allow for prolonged exposure to the protein in the therapeutic range, because the newly secreted protein is present continuously in the blood circulation.

The primary limitation of using recombinant protein is the limited availability of protein after each administration. Plasmid-mediated gene supplementation using injectable DNA plasmid vectors overcomes this, because a single injection into the patient's skeletal muscle permits physiologic expression for extensive periods of time (WO 99/05300 and WO 01/06988). Injection of the vectors promotes the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

In a plasmid-mediated supplementation expression system, a non-viral nucleic acid vector, such as a plasmid, may comprise a synthetic nucleic acid delivery system in addition to a nucleic acid encoding the GHRH being supplemented. In this way, the risks associated with the use of most viral vectors can be avoided. The non-viral expression vector products generally have low toxicity due to the use of "species-specific" components for nucleic acid delivery, which minimizes the risks of immunogenicity generally associated with viral vectors. Additionally, no integration of plasmid sequences into host chromosomes has been reported in vivo to date, so that this type of plasmid-mediated supplementation of GHRH should neither activate oncogenes nor inactivate tumor suppressor genes. As episomal systems residing outside the chromosomes, plasmids have defined pharmacokinetics and elimination profiles, leading to a finite duration of gene expression in target tissues. Furthermore, the plasmid DNA could be engineered so it would be delivered to the cells in a linear rather than circular form (which would further prevent any genomic integration event); the plasmid could be deleted of the antibiotic resistance gene and bacterial origin of replication, making it completely safe for in vivo therapy.

Efforts have been made to enhance the delivery of plasmid DNA to cells by physical means including electroporation, sonoporation, and pressure. Injection by electroporation involves the application of a pulsed electric field to create transient pores in the cellular membrane without causing permanent damage to the cell. It thereby allows for the introduction of exogenous molecules (Smith and Nordstrom, 2000). By adjusting the electrical pulse generated by an electroporetic system, nucleic acid molecules can travel through passageways or pores in the cell that are created during the procedure. U.S. Pat. No. 5,704,908 describes an electroporation apparatus for delivering molecules to cells at a selected location within a cavity in the body of a patient. These pulse voltage injection devices are also described in U.S. Pat. Nos. 5,439,440 and 5,702,304, and PCT WO 96/12520, 96/12006, 95/19805, and 97/07826.

Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone ("GHRH") showed that plasmid therapy with electroporation is scalable and represents a promising approach to induce production and regulated secretion of proteins in large animals and humans (Draghia-Akli et al., 1999; Draghia-Akli et al., 2002).

The ability of electroporation to enhance plasmid uptake into the skeletal muscle has been well documented, as described above. In addition, plasmid formulated with poly-L-glutamate ("PLG") or polyvinylpyrolidone (PVP) has been observed to increase plasmid transfection and consequently expression of the desired transgene. The anionic polymer sodium PLG could enhance plasmid uptake at low plasmid concentrations, while reducing any possible tissue damage caused by the procedure. The ability of electroporation to enhance plasmid uptake into the skeletal muscle has been well documented, as previously described. PLG is a stable compound and resistant to relatively high temperatures (Dolnik et al., 1993). PLG has been previously used to increase stability in vaccine preparations (Matsuo et al., 1994) without increasing their immunogenicity. It also has been used as an anti-toxin post-antigen inhalation or exposure to ozone (Fryer and Jacoby, 1993). In addition, plasmid formulated with PLG or polyvinylpyrrolidone (PVP) has been observed to increase gene transfection and consequently gene expression to up to 10 fold in the skeletal muscle of mice, rats and dogs (Fewell et al., 2001; Mumper et al., 1998). PLG has been used to increase stability of anti-cancer drugs (Li et al., 2000) and as "glue" to close wounds or to prevent bleeding from tissues during wound and tissue repair (Otani et al., 1996; Otani et al., 1998).

Although not wanting to be bound by theory, PLG will increase the transfection of the plasmid during the electroporation process, not only by stabilizing the plasmid DNA, and facilitating the intracellular transport through the membrane pores, but also through an active mechanism For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency.

The use of directly injectable DNA plasmid vectors has been limited in the past. The inefficient DNA uptake into muscle fibers after simple direct injection has led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996).

Although there are references in the art directed to electroporation of eukaryotic cells with linear DNA (McNally et al., 1988; Neumann et al., 1982) (Toneguzzo et al., 1988) (Aratani et al., 1992; Nairn et al., 1993; Xie and Tsong, 1993; Yorifuji and Mikawa, 1990), these examples illustrate transfection into cell suspensions, cell cultures, and the like, and the transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

U.S. Pat. No. 5,874,534 ("the '534 patent") and U.S. Pat. No. 5,935,934 ("the '934 patent") describe mutated steroid receptors, methods for their use and a molecular switch for nucleic acid transfer, the entire content of each is hereby incorporated by reference. A molecular switch for regulating expression in nucleic acid transfer and methods of employing the molecular switch in humans, animals, transgenic animals and plants (e.g. GeneSwitch®) are described in the '534 patent and the '934 patent. The molecular switch is described as a method for regulating expression of a heterologous nucleic acid cassette for nucleic acid transfer and is comprised of a modified steroid receptor that includes a natural steroid receptor DNA binding domain attached to a modified ligand binding domain. The modified binding domain usually binds only non-natural ligands, anti-hormones or non-native ligands. One skilled in the art readily recognizes natural ligands do not readily bind the modified ligand-binding domain and consequently have very little, if any, influence on the regulation and/or expression of the gene contained in the nucleic acid cassette.

Thus, the present invention is directed to a novel method of increasing lean body mass, decreasing body fat proportions, increasing bone density, and/or increasing the rate of bone healing in an animal by plasmid-mediated supplementation of GHRH

SUMMARY

One embodiment of the present invention pertains to a method for decreasing the body fat proportion, increasing lean body mass ("LBM"), increasing bone density, and increasing the rate of bone healing of a subject by utilizing a nucleic acid sequence containing both a constitutive promoter and an encoding sequence for growth hormone releasing hormone ("GHRH") or analog thereof. When this nucleic acid sequence is delivered into the specific cells of the subject (e.g. somatic cells, stem cells, or germ cells), tissue specific constitutive expression of GHRH is achieved. The preferred method to deliver the nucleic acid sequence with the constitutive promoter and the encoding sequence of GHRH or the analog thereof is directly into the cells of the subject by the process of in vivo electroporation. Electroporation may involve externally supplied electrodes, or in the case of needles, internally supplied electrodes to aid in the inclusion of desired nucleotide sequences into the cells of a subject while the cells are within a tissue of the subject.

Another embodiment of the present invention pertains to a method for decreasing the body fat proportion, increasing LBM, increasing bone density, and increasing bone healing rate of a subject by utilizing the ability to regulate the expression of GHRH or analog thereof. Regulation is achieved by delivering into the cells of the subject a first nucleic acid sequence, and a second nucleic acid sequence, followed by a molecular switch; where the first nucleic acid sequence contains an inducible-promoter with a coding region for a growth-hormone-releasing-hormone ("inducible-GHRH") or an analog thereof and the second nucleic acid sequence has a constitutive promoter with a coding region for an inactive regulator protein. By delivering a molecular switch molecule (e.g. mifepistone) into the subject, the inactive regulator protein becomes active and initiates transcription of the inducible-GHRH in the subject. The expression and ensuing release of GHRH or analog thereof by the modified-cells within the subject will decrease the body fat proportion and increase the LBM of the subject in a manner that can be regulated by external molecular switch molecules (e.g. mifepistone). The delivery of the nucleic acid sequences that allow external regulation of GHRH or the analog thereof directly into the cells of the subject can be accomplished by the process of in vivo electroporation.

A further embodiment of the present invention pertains to a method for increasing lean body mass, decreasing body fat proportion, increasing bone density, increasing the rate of bone healing, or a combination thereof, of a subject by utilizing therapy that introduces specific recombinant GHRH-analog protein into the subject.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the amino acid sequence of GHRH or functional biological equivalent thereof. All mutant sequences were obtained by site directed mutagenesis of the porcine wild type sequence.

DETAILED DESCRIPTION OF PREFERRED EMBODIMENTS

Figure 2:
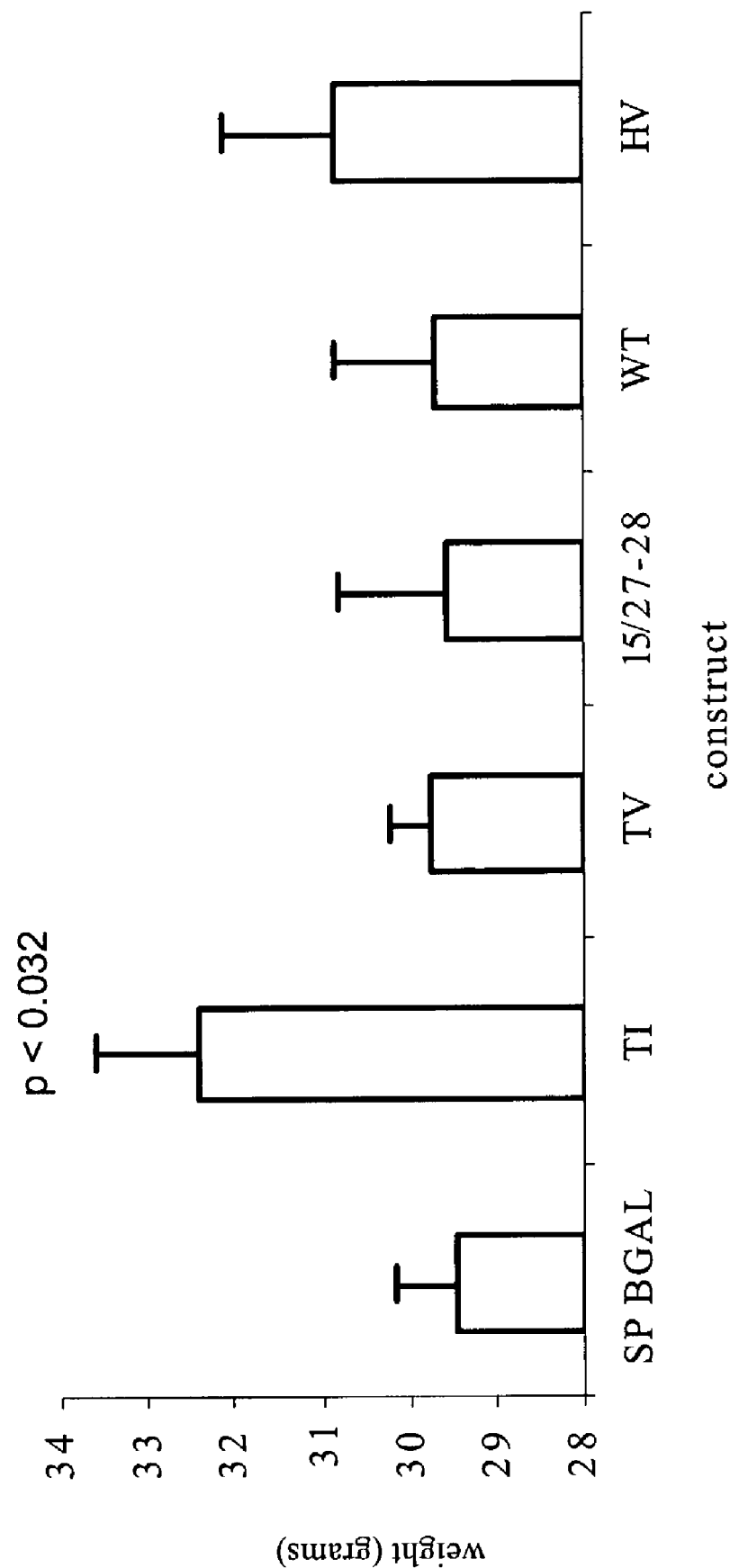
FIG. 2 shows the body weight of SCID mice that were injected with 7.5 micrograms of pSP-GHRH mutants.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Definitions

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "any range derivable therein" as used herein means a range selected from the numbers described in the specification, and "any integer derivable therein" means any integer between such a range.

The term "analog" as used herein includes any mutant of GHRH, or synthetic or naturally occurring peptide fragments of GHRH, such as HV-GHRH (Seq ID No: 1), TI-GHRH (Seq ID No: 2), TV-GHRH (Seq ID No: 3), 15/27/28-GHRH (Seq ID No: 4), (1-44)NH$_2$ (Seq ID No: 5) or (1-40)OH (Seq ID No: 6) forms, or any shorter form to no less than (1-29) amino acids.

The term "bone density" as used herein is defined as the density of minerals in the bone as measured by a standard means in the art, such as x-ray, MI, dual-energy x-ray absorbitometry (DEXA), or any advanced imaging system in the art.

The term "cassette" as used herein is defined as one or more transgene expression vectors.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "coding region" as used herein refers to any portion of the DNA sequence that is transcribed into messenger RNA (mRNA) and then translated into a sequence of amino acids characteristic of a specific polypeptide.

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "donor-cells" as used herein refers to any cells that have been removed and maintained in a viable state for any period of time outside the donor-subject.

The term "donor-subject" as used herein refers to any species of the animal kingdom wherein cells have been removed and maintained in a viable state for any period of time outside the subject.

The term "DNA fragment" or "nucleic acid expression construct" as used herein refers to a substantially double stranded DNA molecule. Although the fragment may be generated by any standard molecular biology means known in the art, in some embodiments the DNA fragment or expression construct is generated by restriction digestion of a parent DNA molecule. The terms "expression vector," "expression cassette," or "expression plasmid" can also be used interchangeably. Although the parent molecule may be any standard molecular biology DNA reagent, in some embodiments the parent DNA molecule is a plasmid.

The term "electroporation" as used herein refers to a method that utilizes electrical pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide of GHRH The term "functional biological equivalent" of GHRH as used herein is a polypeptide that has a distinct amino acid sequence from a wild type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis.

The term "GeneSwitch®" (which is a registered trademark of Valentis, Inc. (Burlingame, Calif.)) as used herein refers to the technology of mifepristone-inducible heterologous nucleic acid sequences encoding regulator proteins, GHRH, functional biological equivalent or combination thereof. Such a technology is schematically diagramed in FIG. 1A. A skilled artisan recognizes that antiprogesterone agent alternatives to mifepristone are available, including onapristone, ZK112993, ZK98734, and 5α pregnane-3,2-dione.

The term "growth hormone" ("GH") as used herein is defined as a hormone that relates to growth and acts as a chemical messenger to exert its action on a target cell. In a specific embodiment, the growth hormone is released by the action of growth hormone releasing hormone.

The term "growth hormone releasing hormone" ("GHRH") as used herein is defined as a hormone that facilitates or stimulates release of growth hormone, and in a lesser extent other pituitary hormones, such as prolactin. It is understood that the GHRH, the recombinant GHRH, or a functional biological equivalent are biologically active.

The term "heterologous nucleic acid sequence" as used herein is defined as a DNA sequence comprising differing regulatory and expression elements.

The term "lean body mass" ("LBM") as used herein is defined as the mass of the body of an animal attributed to non-fat tissue such as muscle.

The term "modified cells" as used herein is defined as the cells from a subject that have an additional nucleic acid sequence introduced into the cell.

The term "modified-donor-cells" as used herein refers to any donor-cells that harbor a GHRH encoding nucleic acid sequence.

The term "molecular switch" as used herein refers to a molecule that is delivered into a subject that can regulate transcription of a gene. A skilled artisan recognizes that there are many such switches known in the art, such as a tetracycline switch, a zinc finger switch, a glucocorticoid switch, and so forth.

The term "nucleic acid expression construct" as used herein refers to any type of genetic construct comprising a nucleic acid coding for a RNA capable of being transcribed. The term "expression vector" can also be used interchangeably herein. In specific embodiments, the nucleic acid expression construct comprises: a promoter, a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette (that contains heterologous nucleic acid sequence encoding GHRH or functional biological equivalent thereof) into the cells of a subject and the allowing of the expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing a nucleic acid expression construct in vivo.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly linear DNA fragments, into the cells of the organism.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vivo amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "rate of bone healing" as used herein is defined as the time required to repair a bone fracture.

The term "recipient-subject" as used herein refers to any species of the animal kingdom wherein modified-donor-cells can be introduced from a donor-subject.

The term "regulator protein" as used herein refers to a protein that increases or facilitates transcription of a target nucleic acid sequence.

The term "residual linear plasmid backbone" as used herein comprises any fragment of the plasmid backbone that is left at the end of the process making the nucleic acid expression plasmid linear.

The terms "subject" or "animal" as used herein refers to any species of the animal kingdom In preferred embodiments, it refers more specifically to humans and domesticated animals used for pets (e.g. cats, dogs, etc.); work (e.g. horses, etc.); food (cows, chicken, fish, lambs, pigs, etc); and all others known in the art.

The term "tissue" as used herein refers to a collection of similar cells and the intercellular substances surrounding them A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of linear DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly A sequence, or a 3' or 5' UTR.

The term "transfects" as used herein refers to introduction of a nucleic acid into a eukaryotic cell. In some embodiments, the cell is not a plant tissue or a yeast cell.

The term "viral backbone" as used herein refers to a nucleic acid sequence that does not contain a promoter, a gene, and a 3' poly A signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The term "vascular pressure pulse" refers to a pulse of pressure from a large volume of liquid to facilitate uptake of a vector into a cell. A skilled artisan recognizes that the amount and duration of the vascular pressure pulse is dependent on the tissue, size, and overall health of the recipient animal, and furthermore knows how to determine such parameters empirically.

The term "vector" as used herein refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

The present invention concerns a method for decreasing the body fat proportion, increasing lean body mass ("LBM"), increasing bone density, increasing the rate of bone healing, or a combination thereof, of an animal subject. In general the present invention can be accomplished by delivering a nucleic acid sequence encoding GHRH or functional biological equivalent thereof into the cells of the subject (e.g. somatic, stem, or germ cells) and allowing expression of the encoded gene to occur while the modified cells are within the living organism. The subsequent expression of the GHRH or functional biological equivalent thereof is regulated by a tissue specific promoter (e.g. muscle), and/or by a regulator protein that contains a modified ligand binding domain (e.g. molecular switch), which will only be active when the correct modified ligand (e.g. mifepistone) is administered to the subject. The expression and ensuing release of GHRH or functional biological equivalent thereof by the modified cells within the living organism will decrease the body fat proportion, increase the LBM, increase the bone density, and/or increase the bone healing rate of the subject.

One aspect of the current invention is a method for altering lean body mass in a subject by utilizing a nucleic acid expression vector regulated by a constitutive promoter. The method comprises delivering into cells of the subject the nucleic acid expression construct that encodes a growth-hormone-releasing-hormone ("GHRH") or functional biological equivalent thereof. In a specific embodiment, the nucleic acid expression construct is delivered into the cells of the subject via electroporation, wherein the cells comprise somatic, stem or germ cells. In another specific embodiment the nucleic acid expression construct comprises Seq ID No: 11, Seq ID No: 12, Seq ID No: 13, Seq ID No: 14, Seq ID No: 17, Seq ID No: 18, Seq ID No: 19, Seq ID No: 20, or Seq ID No: 21. Transfection of the nucleic acid expression construct can be expedited by utilizing a transfection-facilitating polypeptide (e.g. charged polypeptide or poly-L-glutamate). The encoded GHRH or functional biological equivalent thereof are expressed in tissue specific cells of the subject, which comprises muscle cells. The encoded GHRH or the encoded functional biological equivalent of GHRH are biologically active polypeptides that have been engineered to contain a distinct amino acid sequence while simultaneously having similar or improved biologically activity when compared to the GHRH polypeptide. In a preferred embodiment the encoded GHRH or functional biological equivalent thereof is of formula (SEQ ID No: 6). Additionally, the encoded GHRH or functional biological equivalent thereof facilitates growth hormone ("GH") secretion in the subject.

A second aspect of the current invention is a method for altering lean body mass in a subject by utilizing a nucleic acid expression vector regulated by a molecular switch molecule. The method comprises steps of delivering into cells of the subject a first nucleic acid expression construct (Seq ID No: 26), a second nucleic acid expression construct (Seq ID No: 27), and a molecular switch; wherein the first nucleic acid expression construct encodes growth-hormone-releasing-hormone ("GHRH") or functional biological equivalent thereof; and wherein the second nucleic acid expression construct has an encoding region of a regulator protein; and delivering a molecular switch molecule into the subject, wherein the molecular switch molecule governs activation of the regulator protein and the regulator protein governs the activation of the first nucleic acid expression construct. In some specific embodiments, the nucleic acid expression construct further comprises a transfection-facilitating polypeptide (e.g. a charged polypeptide or poly-L-glutamate). The delivering step of the first nucleic acid and the second nucleic acid expression construct into the cells of the subject is via electroporation. A specific embodiment of this method comprises that delivering the nucleic acid expression construct into the cells of the subject initiates expression of the encoded regulatory protein, but the regulatory protein is inactive. However, upon delivering a molecular switch (e.g. mifepristone) into the subject, the regulatory protein becomes active, and the active regulatory protein initiates expression of the GHRH or functional biological equivalent encoded on the first nucleic acid sequence. The encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide. The encoded GHRH or functional biological equivalent thereof is of formula (SEQ ID No: 6). The encoded GHRH or functional biological equivalent thereof facilitates growth hormone ("GH") secretion in the subject. In another specific embodiment, the first nucleic acid expression vector encodes a polypeptide of sequence Seq ID No: 1, Seq ID No: 2, Seq ID No: 3, or Seq ID No: 4.

A third aspect of the current invention is a altering lean body mass in a subject comprising the steps of: delivering into a subject a recombinant growth-hormone-releasing-hormone ("GHRH") or a biological functional equivalent thereof, wherein the recombinant GHRH is a biologically active polypeptide. In specific embodiments, the recombinant functional biological equivalent of GHRH is a polypeptide that has been engineered to contain a distinct amino acid sequence while simultaneously having similar or improved biologically activity when compared to the GHRH polypeptide. In another specific embodiment, the recombinant GHRH or functional biological equivalent thereof is of formula (SEQ ID No: 6). The recombinant GHRH or functional biological equivalent thereof facilitates growth hormone ("GH") secretion in the subject.

A fourth aspect of the current invention is a method for altering bone properties in a subject by utilizing a nucleic acid expression vector regulated by a constitutive promoter. The method comprises delivering into cells of the subject the nucleic acid expression construct that encodes a growth-hormone-releasing-hormone ("GHRH") or functional biological equivalent thereof. In a specific embodiment, the nucleic acid expression construct is delivered into the cells of the subject via electroporation, wherein the cells comprise somatic, stem or germ cells. In another specific embodiment the nucleic acid expression construct comprises Seq ID No: 11, Seq ID No: 12, Seq ID No: 13, Seq ID No: 14, Seq ID No: 17, Seq ID No: 18, Seq ID No: 19, Seq ID No: 20, or Seq ID No: 21. Transfection of the nucleic acid expression construct can be expedited by utilizing a transfection-facilitating polypeptide (e.g. charged polypeptide or poly-L-glutamate). The encoded GHRH or functional biological equivalent thereof are expressed in tissue specific cells of the subject, which comprises muscle cells. The encoded GHRH or the encoded functional biological equivalent of GHRH are biologically active polypeptides that have been engineered to contain a distinct amino acid sequence while simultaneously having similar or improved biologically activity when compared to the GHRH polypeptide. In a preferred embodiment the encoded GHRH or functional biological equivalent thereof is of formula (SEQ ID No: 6). Additionally, the encoded GHRH or functional biological equivalent thereof facilitates growth hormone ("GH") secretion in the subject.

A fifth aspect of the current invention is a method for altering bone properties in a subject by utilizing a nucleic acid expression vector regulated by a molecular switch molecule. The method comprises steps of delivering into cells of the subject a first nucleic acid expression construct, a second nucleic acid expression construct, and a molecular switch; wherein the first nucleic acid expression construct encodes growth-hormone-releasing-hormone ("GHRH") or functional biological equivalent thereof; and wherein the second nucleic acid expression construct has an encoding region of a regulator protein; and delivering a molecular switch molecule into the subject, wherein the molecular switch molecule governs activation of the regulator protein and the regulator protein governs the activation of the first nucleic acid expression construct. In some specific embodiments, the nucleic acid expression construct further comprises a transfection-facilitating polypeptide (e.g. a charged polypeptide or poly-L-glutamate). The delivering step of the first nucleic acid and the second nucleic acid expression construct into the cells of the subject is via electroporation. A specific embodiment of this method comprises that delivering the nucleic acid expression construct into the cells of the subject initiates expression of the encoded regulatory protein, but the regulatory protein is inactive. However, upon delivering a molecular switch (e.g. mifepristone) into the subject, the regulatory protein becomes active, and the active regulatory protein initiates expression of the GHRH or functional biological equivalent encoded on the first nucleic acid sequence. The encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide. The encoded GHRH or functional biological equivalent thereof is of formula (SEQ ID No: 6). The encoded GHRH or functional biological equivalent thereof facilitates growth hormone ("GH") secretion in the subject. In another specific embodiment, the first nucleic acid expression vector encodes a polypeptide of sequence Seq ID No: 1, Seq ID No: 2, Seq ID No: 3, or Seq ID No: 4.

A sixth aspect of the current invention is a method for altering bone properties in a subject comprising the steps of: delivering into a subject a recombinant growth-hormone-releasing-hormone ("GHRH") or a biological functional equivalent thereof, wherein the recombinant GHRH is a biologically active polypeptide. In specific embodiments, the recombinant functional biological equivalent of GHRH is a polypeptide that has been engineered to contain a distinct amino acid sequence while simultaneously having similar or improved biologically activity when compared to the GHRH polypeptide. In another specific embodiment, the recombinant GHRH or functional biological equivalent thereof is of formula (SEQ ID No: 6). The recombinant GHRH or functional biological equivalent thereof facilitates growth hormone ("GH") secretion in the subject.

The plasmid-mediated supplementation of GHRH approach described herein offers advantages over the limitations of directly injecting recombinant GHRH protein. Expression of nucleic acid sequences encoding novel functional biological equivalents of GHRH that are serum protease resistant can be directed by an expression plasmid controlled by a synthetic muscle-specific promoter. Expression of such GHRH or functional biological equivalent thereof elicited high GH and IGF-I levels in pigs following delivery by intramuscular injection and in ziw electroporation (Draghia-Akli et al., 1999). The process of in ziw electroporation may involve externally supplied electrodes, or in the case of needles, internally supplied electrodes to aid in the inclusion of desired nucleotide sequences into the cells of the subject within the living organism. Although in vivo electroporation is the preferred method of introducing the heterologous nucleic acid encoding system into the cells of the subject, other methods exist and are known by a person skilled in the art (e.g. electroporation, lipofectamine, calcium phosphate, ex vivo transformation, direct injection, DEAE dextran, sonication loading, receptor mediated transfection, microprojectile bombardment, etc.). For example, it is also possible to introduce the nucleic acid sequence that encodes the GHRH or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). The GHRH sequence can be cloned into an adenovirus vector or an adeno-associated vector and delivered by simple intramuscular injection, or intravenous or intra-arterial injection. Plasmid DNA carrying the GHRH sequence can be complexed with cationic lipids or liposomes and delivered intramuscularly, intravenously or subcutaneously.

Administration as used herein refers to the route of introduction of a vector or carrier of DNA into the body. Administration can be directly to a target tissue or by targeted delivery to the target tissue after systemic administration. In particular, the present invention can be used for supplementing GHRH by administration of the vector, such as a plasmid, to the body in order to establish controlled expression of the specific nucleic acid sequence within tissues at certain useful levels.

The preferred means for administration of vector and use of formulations for delivery are described above. The preferred embodiment is by in vivo electroporation.

The route of administration of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhanced by utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determines the bioavailability of the vector within the body. Other elements of the formulation function as ligand which interact with specific receptors on the surface or interior of the cell. Other elements of the formulation function to enhance entry into the cell, release from the endosome, and entry into the nucleus.

Delivery can also be through use of DNA transporters. DNA transporters refers to molecules which bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. One element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such a ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not only tolerated but nurtured. Myoblasts can easily be obtained by taking muscle tissue from an individual who needs supplementation of GHRH, and the genetically engineered cells can also be easily put back with out causing damage to the patient Is muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the El region of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

Although not wanting to be bound by theory, it is believed that in order to provide an acceptable safety margin for the use of such heterologous nucleic acid sequences in humans, a regulated gene expression system is mandated to possess low levels of basal expression of GHRH, and still retain a high inducibility. Thus, target gene expression can be regulated by incorporating molecular switch technology as schematically diagramed in FIG. 1A. The commercially available GeneSwitch® system for ligand-dependent induction of transgene expression is based on a C-terminally truncated progesterone receptor that fails to bind to its natural agonist, progesterone, but instead is activated by antiprogestins, such as mifepristone ("MFP") (Vegeto et al., 1992; Xu et al., 1996). Thus, the heterologous nucleic acid sequence introduced into the cells of the subject requires MFP to be transcriptionally activated. The chimeric regulator protein of the GeneSwitch® system consists of the ligand binding domain of the truncated human progesterone receptor that has been fused to the DNA binding domain of the yeast GAL4 protein (which binds a specific 17 bp recognition sequence) and a transcriptional activation domain from the p65 subunit of human NF-kB (Abruzzese et al., 1999; Abruzzese et al., 2000). The gene for the GeneSwitch® regulator protein was inserted into a myogenic expression vector, designated pGS1633, which is expressed constitutively under the control of a muscle-specific skeletal alpha-actin ("SK") promoter The GHRH plasmid, designated, p6xGa14/TATA-GHRH, or pGHRH1633 contains an inducible promoter that consists of six copies of the 17-mer Ga14 binding site fused to a minimal TATA box promoter. The GHRH coding sequence is a 228-bp fragment of super-porcine mutated GHRH cDNA, termed HV-GHRH (Draghia-Akli et al., 1999). The HV-GHRH molecule displays a high degree of stability in serum, with a half-life of 6 hours, versus the natural GHRH, that has a 6-12 min half-life. The muscle-specific GeneSwitch® and inducible GHRH plasmids both have a 5' untranslated region that contains a synthetic intron, and a 3' untranslated region/poly (A) site that is from the human GH gene.

Recombinant GH replacement therapy is widely used clinically, with beneficial effects, but generally, the doses are supraphysiological. Such elevated doses of recombinant GH are associated with deleterious side-effects, for example, up to 30% of the recombinant GH treated patients report a higher frequency of insulin resistance (Blethen, 1995; Verhelst et al., 1997) or accelerated bone epiphysis growth and closure in pediatric patients (Blethen and Rundle, 1996). In addition, molecular heterogeneity of circulating GH may have important implications in growth and homeostasis, which can lead to a less potent GH that has a reduced ability to stimulate the prolactin receptor; it has also been described that the 20 kDa form of GH has less potency to cause urine retention than the 22 kDa form (Satozawa et al., 2000; Tsunekawa et al., 1999; Wada et al., 1998). These unwanted side effects result from the fact that treatment with recombinant exogenous GH protein raises basal levels of GH and abolishes the natural episodic pulses of GH. In contradistinction, no side effects have been reported for recombinant GHRH therapies. The normal levels of GHRH in the pituitary portal circulation range from about 150-to-800 pg/ml, while systemic circulating values of the hormone are up to about 100-500 pg/ml. Some patients with acromegaly caused by extracranial tumors have level that is nearly 10 times as high (e.g. 50 ng/ml of immunoreactive GHRH) (Thorner et al., 1984). Long-term studies using recombinant GHRH therapies (1-5 years) in children and elderly humans have shown an absence of the classical GH side-effects, such as changes in fasting glucose concentration or, in pediatric patients, the accelerated bone epiphysal growth and closure or slipping of the capital femoral epiphysis (Chevalier et al., 2000) (Duck et al., 1992; Vittone et al., 1997). Numerous studies in humans, sheep or pigs showed that continuous infusion with recombinant GHRH protein restores the normal GH pattern without desensitizing GHRH receptors or depleting GH supplies (Dubreuil et al., 1990b). As this system is capable of a degree of feed-back which is abolished in the GH therapies, GHRH recombinant protein therapy may be more physiological than GH therapy. However, due to the short half-life of GHRH in vivo, frequent (one to three times per day) intravenous, subcutaneous or intranasal (requiring 300-fold higher dose) administrations are necessary (Evans et al., 1985; Thorner et al., 1986). Thus, as a chronic therapy, recombinant GHRH protein administration is not practical. A gene transfer approach, however could overcome this limitations to GHRH use. Moreover, a wide range of doses can be therapeutic. The choice of GHRH for a gene therapeutic application is favored by the fact that the gene, cDNA and native and several mutated molecules have been characterized for the pig and other species (Bohlen et al., 1983; Guillemin et al., 1982), and the measurement of therapeutic efficacy is straightforward and unequivocal.

Among the non-viral techniques for gene transfer in vivo, the direct injection of plasmid DNA into muscle is simple, inexpensive, and safe. The inefficient DNA uptake into muscle fibers after simple direct injection hag led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996). Recently, significant progress to enhance plasmid delivery in vivo and subsequently to achieve physiological levels of a secreted protein was obtained using the electroporation technique. Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Preliminary experiments indicated that for a large animal model, needle electrodes give consistently better reproducible results than external caliper electrodes.

Combining the powerful electroporation delivery method with an improved plasmid DNA vector system produced significant changes that decreased the body fat proportion, increased lean body mass ("LBM"), or both, in an animal, such as a large animal, at very low plasmid dosage.

I. Vectors

The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques (see, for example, (Sambrook et al., 1989).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operatively linked coding sequence in a particular host cell. In addition to control sequences that govern transcription and translation, vectors and expression vectors may contain nucleic acid sequences that serve other functions as well and are described infra.

II. Plasmid Vectors

In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is derived from pBlueScript KS+ and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase ("GST") soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

III. Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example (Sambrook et al., 1989)). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | Relevant References |
|---|---|
| Immunoglobulin Heavy Chain | |
| Immunoglobulin Light Chain | |
| T-Cell Receptor | |
| HLA DQ a and/or DQ β | |
| β-Interferon | |
| Interleukin-2 | |
| Interleukin-2 Receptor | |
| MHC Class II 5 | |
| MHC Class II HLA-Dra | |
| β-Actin | (Kawamoto et al., 1988; Kawamoto et al., 1989) |
| Muscle Creatine Kinase (MCK) | (Horlick and Benfield, 1989; Jaynes et al., 1988) |
| Prealbumin (Transthyretin) | |
| Elastase I | |
| Metallothionein (MTII) | (Inouye et al., 1994; Narum et al., 2001; Skroch et al., 1993) |
| Collagenase | |
| Albumin | (Pinkert et al., 1987; Tronche et al., 1989) |
| α-Fetoprotein | |
| γ-Globin | |
| β-Globin | (Tronche et al., 1990; Trudel and Costantini, 1987) |
| c-fos | |
| c-HA-ras | |
| Insulin | (German et al., 1995; Ohlsson et al., 1991) |
| Neural Cell Adhesion Molecule (NCAM) | |
| α₁-Antitrypsin | |
| H2B (TH2B) Histone | |
| Mouse and/or Type I Collagen | |
| Glucose-Regulated Proteins (GRP94 and GRP78) | |
| Rat Growth Hormone | (Larsen et al., 1986) |
| Human Serum Amyloid A (SAA) | |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| SV40 | |
| Polyoma | |
| Retroviruses | |

TABLE 1-continued

Promoter and/or Enhancer

| Promoter/Enhancer | Relevant References |
|---|---|
| Papilloma Virus | |
| Hepatitis B Virus | |
| Human Immunodeficiency Virus | |
| Cytomegalovirus (CMV) | (Boshart et al., 1985; Dorsch-Hasler et al., 1985) |
| Gibbon Ape Leukemia Virus | |
| Synthetic muscle specific promoters (c5-12,c1-28) | (Draghia-Akli et al., 1999; Draghia-Akli et al., 2002; Li et al., 1999) |

TABLE 2

Element/Inducer

| Element | Inducer |
|---|---|
| MT II | Phorbol Ester (TFA) |
| | Heavy metals |
| MMTV (mouse mammary tumor virus) | Glucocorticoids |
| β-Interferon | Poly(rI)x/Poly(rc) |
| Adenovirus 5 E2 | E1A |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | E1A, SV40 Large T Antigen |
| Proliferin | Phorbol Ester-TPA |
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Nonlimiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), D1A dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (Li et al., 1999), which contains a proximal serum response element ("SRE") from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

IV. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites ("IRES") elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

V. Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

VI. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, (Chandler et al., 1997), herein incorporated by reference.)

VII. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

VIII. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal, skeletal alpha actin 3'UTR or the human or bovine growth hormone polyadenylation signal, convenient and known to function well in various target cells. Polyadenylation may increase the stability of the transcript or may facilitate cytoplasmic transport.

IX. Origins of Replication

In order to propagate a vector in a host cell, it may contain one or more origins of replication sites (often termed "ori"), which is a specific nucleic acid sequence at which replication is initiated. Alternatively an autonomously replicating sequence ("ARS") can be employed if the host cell is yeast.

X. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase ("tk") or chloramphenicol acetyltransferase ("CAT") may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

XI. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances, maintain a resting transmembrane potential of ca. 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the interelectrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol, and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

One embodiment of the present invention to overcome the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determined by the nature of tissue, the size of the selected tissue and distance between electrodes. It is desirable that the voltage pulse be as homogenous as possible and of the correct amplitude. Excessive field strength results in the lysing of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

XII. Restriction Enzymes

In some embodiments of the present invention, a linear DNA fragment is generated by restriction enzyme digestion of a parent DNA molecule. Examples of restriction enzymes are provided in the following table.

| Name | Recognition Sequence | |
|---|---|---|
| AatII | GACGTC | |
| Acc65 I | GGTACC | |
| Acc I | GTMKAC | |
| Aci I | CCGC | |
| Acl I | AACGTT | |
| Afe I | AGCGCT | |
| Afl II | CTTAAG | |
| Afl III | ACRYGT | |
| Age I | ACCGGT | |
| Ahd I | GACNNNNNGTC | SEQ ID No. 28 |
| Alu I | AGCT | |
| Alw I | GGATC | |
| AlwN I | CAGNNNCTG | SEQ ID No. 29 |
| Apa I | GGGCCC | |
| ApaL I | GTGCAC | |
| Apo I | RAATTY | |
| Asc I | GGCGCGCC | |
| Ase I | ATTAAT | |
| Ava I | CYCGRG | |
| Ava II | GGWCC | |
| Avr II | CCTAGG | |
| Bae I | NACNNNNGTAPyCN | SEQ ID No. 30 |
| BamH I | GGATCC | |
| Ban I | GGYRCC | |
| Ban II | GRGCYC | |
| Bbs I | GAAGAC | |
| Bbv I | GCAGC | |
| BbvC I | CCTCAGC | |

| Name | Recognition Sequence | | Name | Recognition Sequence | |
|---|---|---|---|---|---|
| Bcg I | CGANNNNNNTGC SEQ ID No. 31 | | BssS I | CACGAG | |
| BciV I | GTATCC | | BstAP I | GCANNNNNTGC SEQ ID No. 35 | |
| Bcl I | TGATCA | | BstB I | TTCGAA | |
| Bfa I | CTAG | | BstE II | GGTNACC | |
| Bgl I | GCCNNNNNGGC SEQ ID No. 32 | | BstF5 I | GGATGNN | |
| Bgl II | AGATCT | | BstN I | CCWGG | |
| Blp I | GCTNAGC | | BstU I | CGCG | |
| Bmr I | ACTGGG | | BstX I | CCANNNNNNTGG | |
| Bpm I | CTGGAG | | BstY I | RGATCY | |
| BsaA I | YACGTR | | BstZ17 I | GTATAC | |
| BsaB I | GATNNNNATC SEQ ID No. 33 | | Bsu36 I | CCTNAGG | |
| BsaH I | GRCGYC | | Btg I | CCPuPyGG | |
| Bsa I | GGTCTC | | Btr I | CACGTG | |
| BsaJ I | CCNNGG | | Cac8 I | GCNNGC | |
| BsaW I | WCCGGW | | Cla I | ATCGAT | |
| BseR I | GAGGAG | | Dde I | CTNAG | |
| Bsg I | GTGCAG | | Dpn I | GATC | |
| BsiE I | CGRYCG | | Dpn II | GATC | |
| BsiHKA I | GWGCWC | | Dra I | TTTAAA | |
| BsiW I | CGTACG | | Dra III | CACNNNGTG SEQ ID No. 37 | |
| Bsl I | CCNNNNNNNGG SEQ ID No. 34 | | Drd I | GACNNNNNNGTC SEQ ID No. 38 | |
| BsmA I | GTCTC | | Eae I | YGGCCR | |
| BsmB I | CGTCTC | | Eag I | CGGCCG | |
| BsmF I | GGGAC | | Ear I | CTCTTC | |
| Bsm I | GAATGC | | Eci I | GGCGGA | |
| BsoB I | CYCGRG | | EcoN I | CCTNNNNNAGG SEQ ID No. 39 | |
| Bsp1286 I | GDGCHC | | EcoO109 I | RGGNCCY | |
| BspD I | ATCGAT | | EcoR I | GAATTC | |
| BspE I | TCCGGA | | EcoR V | GATATC | |
| BspH I | TCATGA | | Fau I | CCCGCNNNN SEQ ID No. 40 | |
| BspM I | ACCTGC | | Fnu4H I | GCNGC | |
| BsrB I | CCGCTC | | Fok I | GGATG | |
| BsrD I | GCAATG | | Fse I | GGCCGGCC | |
| BsrF I | RCCGGY | | Fsp I | TGCGCA | |
| BsrG I | TGTACA | | Hae II | RGCGCY | |
| Bsr I | ACTGG | | Hae III | GGCC | |
| BssH II | GCGCGC | | Hga I | GACGC | |
| BssK I | CCNGG | | Hha I | GCGC | |
| Bst4C I | ACNGT | | | | |

| Name | Recognition Sequence | | Name | Recognition Sequence | |
|---|---|---|---|---|---|
| Hinc II | GTYRAC | | PleI | GAGTC | |
| Hind III | AAGCTT | | Pme I | GTTTAAAC | |
| Hinf I | GANTC | | Pml I | CACGTG | |
| HinP1 I | GCGC | | PpuM I | RGGWCCY | |
| Hpa I | GTTAAC | | PshA I | GACNNNNGTC | SEQ ID No. 46 |
| Hpa II | CCGG | | Psi I | TTATAA | |
| Hph I | GGTGA | | PspG I | CCWGG | |
| Kas I | GGCGCC | | PspOM I | GGGCCC | |
| Kpn I | GGTACC | | Pst I | CTGCAG | |
| Mbo I | GATC | | Pvu I | CGATCG | |
| Mbo II | GAAGA | | Pvu II | CAGCTG | |
| Mfe I | CAATTG | | Rsa I | GTAC | |
| Mlu I | ACGCGT | | Rsr II | CGGWCCG | |
| Mly I | GAGTCNNNNN | SEQ ID No. 41 | Sac I | GAGCTC | |
| Mnl I | CCTC | | Sac II | CCGCGG | |
| Msc I | TGGCCA | | Sal I | GTCGAC | |
| Mse I | TTAA | | Sap I | GCTCTTC | |
| Msl I | CAYNNNNRTG | SEQ ID No. 42 | Sau3A I | GATC | |
| MspA1 I | CMGCKG | | Sau96 I | GGNCC | |
| Msp I | CCGG | | Sbf I | CCTGCAGG | |
| Mwo I | GCNNNNNNNGC | SEQ ID No. 43 | Sca I | AGTACT | |
| Nae I | GCCGGC | | ScrF I | CCNGG | |
| Nar I | GGCGCC | | SexA I | ACCWGGT | |
| Nci I | CCSGG | | SfaN I | GCATC | |
| Nco I | CCATGG | | Sfc I | CTRYAG | |
| Nde I | CATATG | | Sfi I | GGCCNNNNNGGCC | SEQ ID No. 47 |
| NgoMI V | GCCGGC | | Sfo I | GGCGCC | |
| Nhe I | GCTAGC | | SgrA I | CRCCGGYG | |
| Nla III | CATG | | Sma I | CCCGGG | |
| Nla IV | GGNNCC | | Sml I | CTYRAG | |
| Not I | GCGGCCGC | | SnaB I | TACGTA | |
| Nru I | TCGCGA | | Spe I | ACTAGT | |
| Nsi I | ATGCAT | | Sph I | GCATGC | |
| Nsp I | RCATGY | | Ssp I | AATATT | |
| Pac I | TTAATTAA | | Stu I | AGGCCT | |
| PaeR7 I | CTCGAG | | Sty I | CCWWGG | |
| Pci I | ACATGT | | Swa I | ATTTAAAT | |
| PflF I | GACNNNGTC | SEQ ID No. 44 | Taq I | TCGA | |
| PflM I | CCANNNNNTGG | SEQ ID No. 45 | | | |

-continued

| Name | Recognition Sequence | |
|---|---|---|
| Tfi I | GAWTC | |
| Tli I | CTCGAG | |
| Tse I | GCWGC | |
| Tsp45 I | GTSAC | |
| Tsp509 I | AATT | |
| TspR I | CAGTG | |
| Tth111 I | GACNNNGTC | SEQ ID No. 48 |
| Xba I | TCTAGA | |
| Xcm I | CCANNNNNNNNNTGG | SEQ ID No. 49 |
| Xho I | CTCGAG | |
| Xma I | CCCGGG | |
| Xmn I | GAANNNNTTC | SEQ ID No. 50 |

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of DNA Vectors and Methods in Animal Subject

In order to increase lean body mass, decrease body fat proportions, increase bone density, and improve bone healing rate, it was first necessary to design several GHRH expression constructs. Briefly, the plasmid vectors contained the muscle specific synthetic promoter SPc5-12 (Li et al., 1999) attached to a wild type or analog porcine GHRH. The analog GHRH sequences were generated by site directed mutagenesis as described in methods section. Nucleic acid sequences encoding GHRH or analog were cloned into the BamHI/HindIII sites of pSPc5-12 plasmid, to generate pSP-GHRH. Other elements contained in the plasmids include a 3' untranslated region ("3'UTR") (SEQ ID No: 8) of growth hormone and an SV403'UTR from pSEAP-2 Basic Vector as described in the methods section. The unique nucleic acid sequences for the constructs used are shown in FIG. 1.

DNA constructs: Plasmid vectors containing the muscle specific synthetic promoter SPc5-12 (Seq ID No: 7) were previously described (Li et al., 1999). Wild type and mutated porcine GHRH cDNAs were generated by site directed mutagenesis of GHRH cDNA (Seq ID No: 9) (Altered Sites II in vitro Mutagenesis System, Promega, Madison, Wis.), and cloned into the BamHI/Hind III sites of pSPc5-12, to generate pSP-wt-GHRH (Seq ID No: 15), or pSP-HV-GHRH (Seq ID No: 11), respectively. The 3' untranslated region (3'UTR) of growth hormone was cloned downstream of GHRH cDNA. The resultant plasmids contained mutated coding region for GHRH, and the resultant amino acid sequences were not naturally present in mammals. Although not wanting to be bound by theory, the effects on increased bone density, and increased healing rate of bone in the animals are determined ultimately by the circulating levels of mutated hormones. Several different plasmids that encoded different mutated amino acid sequences of GHRH or functional biological equivalent thereof are as follows:

| Plasmid | Encoded Amino Acid Sequence | |
|---|---|---|
| wt-GHRH | YADAIFTNSYRKVLGQLSARKLLQDIMSRQQGERNQEQGA-OH | (SeqID No: 10) |
| HV-GHRH | HVDAIFTNSYRKVLAQLSARKLLQDILNRQQGERNQEQGA-OH | (SeqID No: 1) |
| TI-GHRH | YIDAIFTNSYRKVLAQLSARKLLQDILNRQQGERNQEQGA-OH | (SeqID No: 2) |

| Plasmid | Encoded Amino Acid Sequence |
|---|---|
| TV-GHRH | YVDAIFTNSYRKVLAQLSARKLLQDILNRQQGERNQEQGA-OH (SeqID No: 3) |
| 15/27/28-GHRH | YADAIFTNSYRKVLAQLSARKLLQDILNRQQGERNQEQGA-OH (SeqID No: 4) |

In general, the encoded GHRH or functional biological equivalent thereof is of formula:

-$X_1$-$X_2$-DAIFTNSYRKVL-$X_3$-QLSARKLLQDI-$X_4$-$X_5$-RQQGERNQEQGA-OH (Seq ID No: 6)

wherein: $X_1$ is a D- or L-isomer of an amino acid selected from the group consisting of tyrosine ("Y"), or histidine ("H"); $X_2$ is a D- or L-isomer of an amino acid selected from the group consisting of alanine ("A"), valine ("V"), or isoleucine ("I"); $X_3$ is a D- or L-isomer of an amino acid selected from the group consisting of alanine ("A") or glycine ("G"); $X_4$ is a D- or L-isomer of an amino acid selected from the group consisting of methionine ("M"), or leucine ("L"); $X_5$ is a D- or L-isomer of an amino acid selected from the group consisting of serine ("S") or asparagine ("N").

Another plasmid that was utilized included the pSP-SEAP construct (Seq ID No: 16) that contains the SacI/HindIII SPc5-12 fragment, SEAP gene and SV40 3'UTR from pSEAP-2 Basic Vector (Clontech Laboratories, Inc.; Palo Alto, Calif.).

The plasmids described above do not contain polylinker, IGF-I gene, a skeletal alpha-actin promoter or a skeletal alpha actin 3' UTR/NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein, polypeptide, and/or polynucleotide, is the concept that there is a limit to the number of changes that may be made within a defined portion of the molecule while retaining a molecule with an acceptable level of equivalent biological activity. Functional biological equivalents are thus defined herein as those proteins (and polynucleotides) in selected amino acids (or codons) that may be substituted. A peptide comprising a functional biological equivalent of GHRH is a polypeptide that has been engineered to contain distinct amino acid sequences while simultaneously having similar or improved biologically activity when compared to GHRH. For example, one biological activity of GHRH is to facilitate growth hormone ("GH") secretion in the subject.

Electroporation devices. A BTX T820 generator (BTX, division of Genetronics Inc., CA) was used to deliver square wave pulses in all experiments. Voltage conditions of 100-200 V/cm, 6 pulses, 60 milliseconds per pulse were used. Caliper and needle electrodes (BTX, division of Genetronics Inc., CA) were used to deliver in vivo electric pulses. The plate (caliper) electrodes consisted of 1.5 cm square metallic blocks mounted on a ruler, so the distance between the plates could be easily assessed; the 6-needle device consists of a circular array (1 cm diameter) of six equally spaced filled 21-gauge needles mounted on a non-conductive material. The 3-needle device consists of two filled and one cannular needle, the last one being used both as an electrode and to deliver the plasmid. All needles were 2 cm in length. In all injections the needles were completely inserted into the muscle.

A skilled artisan recognizes that any similar electroporation device and parameters may be used in the present invention so long as the device delivers the nucleic acid sequence to the cell, tissue, or organism.

Intramuscular injection of plasmid DNA in porcine. Two-to three-week-old hybrid barrows (Yorkshire×Landrace×Hampshire×Duroc)(Huntsville, Tex.), 4-5 kg in weight, or Yorkshire×Landrace pigs were used in the secreted embryonic alkaline phosphatase studies (n=3/group). For the GHRH plasmid studies, time-pregnant sows (Yorkshire×Landrace) were brought three weeks before the scheduled parturition date to the Children Nutrition Research Center at Baylor College of Medicine. Piglets were born in the facility. Piglets were assigned randomly to one of the experimental (n=2 pigs/group/series) or controls (n=3) groups. All experiments were repeated three times. The animals were suckled for the first 21 days and then individually housed with ad-lib access to water. For GHRH studies, after weaning, pigs were fed a 24% protein diet (Producers Cooperative Association, Bryan, Tex.) at 6% of their body weight daily. The animals were weighed twice a week, at the same time of day, and the amount of feed was subsequently determined. Animals were maintained in accordance with NIH Guide, USDA and Animal Welfare Act guidelines, and approved by the Baylor College of Medicine IACUC.

Endotoxin-free plasmid (Qiagen Inc., Chatsworth, Calif., USA) preparations were diluted in PBS, pH 7.4 to 1 mg/ml. Plasmid DNA was injected through the intact skin into the semitendinosus or the longissimus dorsi muscle using a 21 g needle. Two minutes later, external caliper electrodes or injectable electrodes (6-needle array or 3-needle array) were applied to the injected muscle, and 6 pulses of 200V/cm, 60 millisecond/pulse were applied. The polarity of the pulses was either constant or inverted between the needles.

Blood was collected by jugular puncture before plasmid injection, and at 3, 7, 14, 21, 35 and 45 days post-injection. At 50 days post-injection, animals were sacrificed and internal organs and the injected muscle were collected, weighed, frozen in liquid nitrogen, and stored at −80° C., or placed in 10% buffered formalin for histology.

Although in vivo electroporation is the preferred method for delivering the nucleic acid constructs into the cells of the subject, suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Nabel et al., 1989; Wilson et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985) U.S. Pat. No. 5,789,215, incorporated herein by reference); by electroporation (U.S. Pat. No. 5,384,253, incorporated herein by reference; (Potter et al., 1984; Tur-Kaspa et al., 1986); by calcium phosphate precipitation (Chen and Okayama, 1987; Graham and van der Eb, 1973; Rippe et al., 1990); by using DEAE-dextran followed by polyethylene glycol (Gopal, 1985); by direct sonic loading (Fechheimer et al., 1987); by liposome mediated transfection (Hafez et al., 2001; Hamm et al., 2002; Madry et al., 2001; Raghavachari and Fahl, 2002; Wiethoff et al., 2001) and receptor-mediated transfection (Wu and Wu, 1988a; Wu and Wu, 1988b); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers ((Johnson et al., 1992); U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993); U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

Porcine plasma IGF-I and insulin concentrations. Porcine IGF-I was measured by heterologous human radioimmunometric assay (Diagnostic System Lab., Webster, Tex.). The sensitivity of the assay was 0.8 ng/ml; intra-assay and inter-assay variation was 3.4% and 4.5%, respectively. Porcine insulin was measured using a heterologous human radioimmunoassay (Linco Research Inc., St. Charles, Mo.). The sensitivity level of the assay was 2 µU/ml; intra-assay and inter-assay variation was 3.2% and 3.9% respectively.

Body composition data. Weights were measured on the same calibrated scales (certified to have an accuracy to ±0.2 kg and a coefficient of variation of 0.3%) throughout the study, twice a week. Body composition measurements were performed in vivo, 50 days after birth. The piglets were anesthetized using a combination of xylazine (15 mg/kg) and ketamine (2 mg/kg) and the total body content of fat, percent of fat, non-bone lean tissue mass and bone mineral content was measured by dual-energy x-ray absorptiometry (Hologic QDR-2000, Waltham, Mass.) ("DEXA") (Toner et al., 1996). Total body potassium was measured in a potassium chamber ("K40") using a whole body detector (Cohn et al., 1984).

Statistics Data are analyzed using STATISTICA analysis package (StatSoft, Inc. Tulsa, Okla.). Values shown in the figures are the mean±s.e.m. Specific P values were obtained by comparison using ANOVA. A P<0.05 was set as the level of statistical significance.

Example 2

Constitutive GHRH System In Vivo

Figure 3:
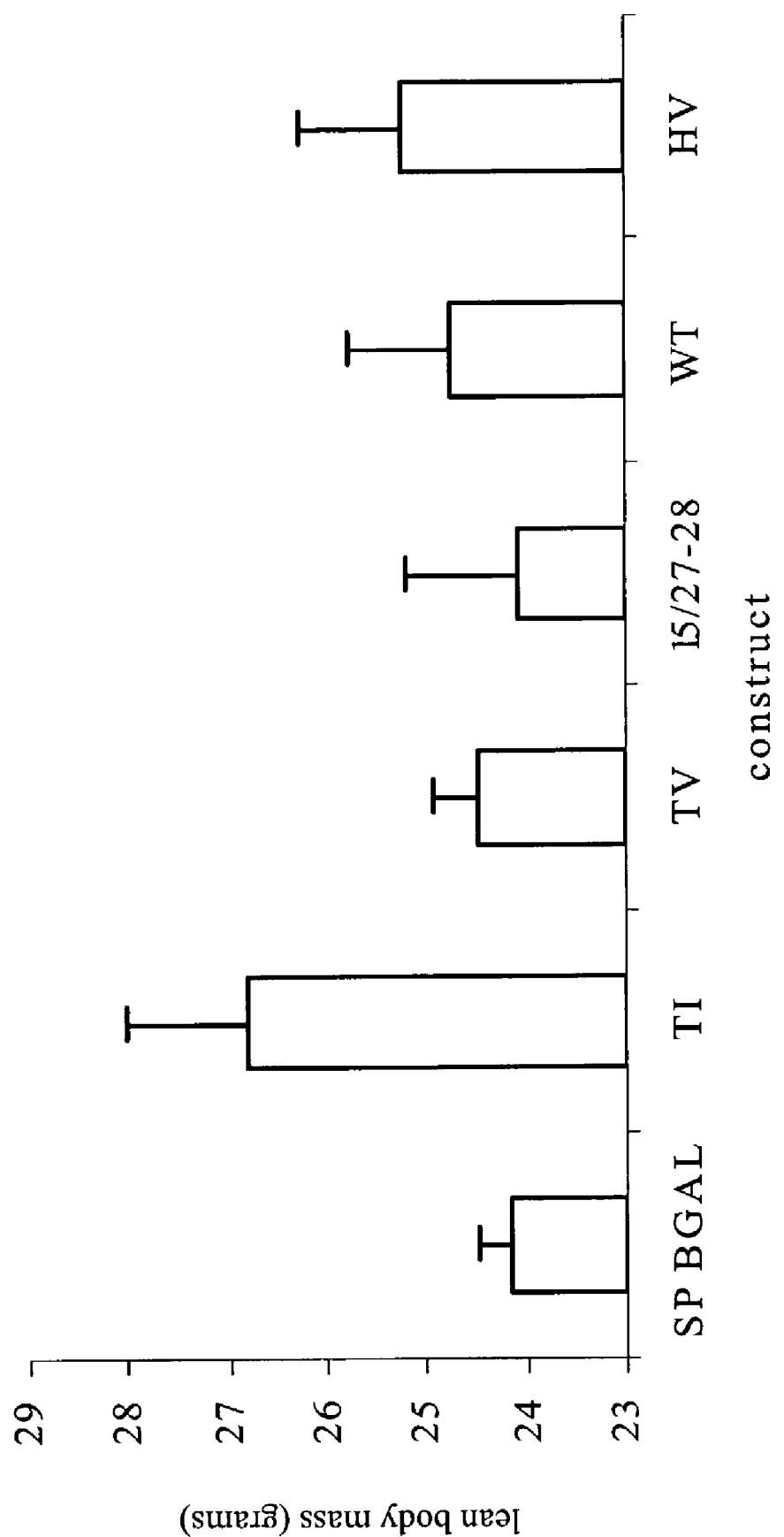
FIG. 3 shows the body composition of SCID mice that were injected with 7.5 micrograms of plasmid expressing either one of the GHRH mutants or a pSP-beta-galactosidase as control.
Figure 4:
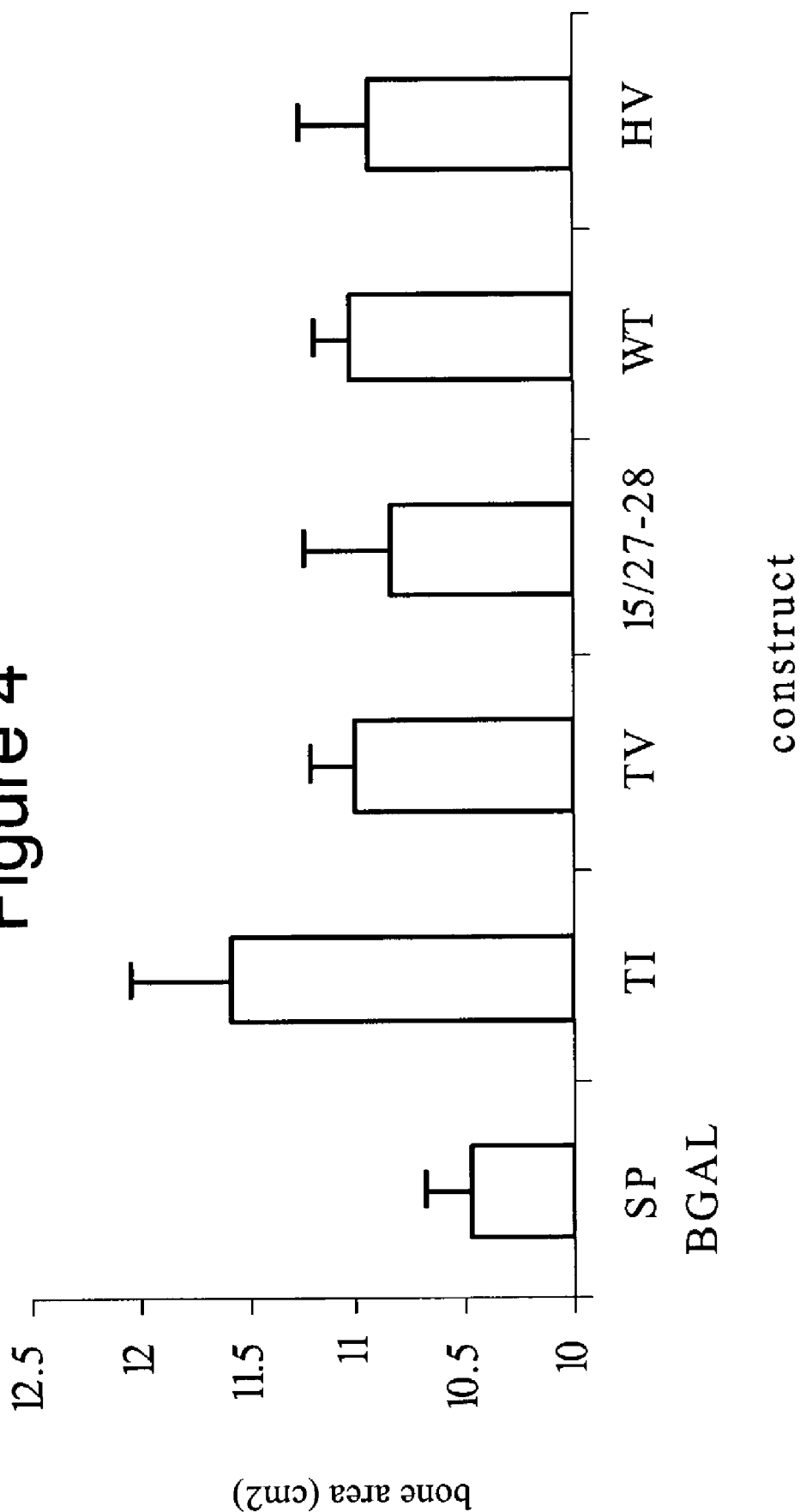
FIG. 4 shows the bone area of SCID mice that were injected with 7.5 micrograms of plasmid expressing either one of the GHRH mutants or a pSP-beta-galactosidase as control.
Figure 5:
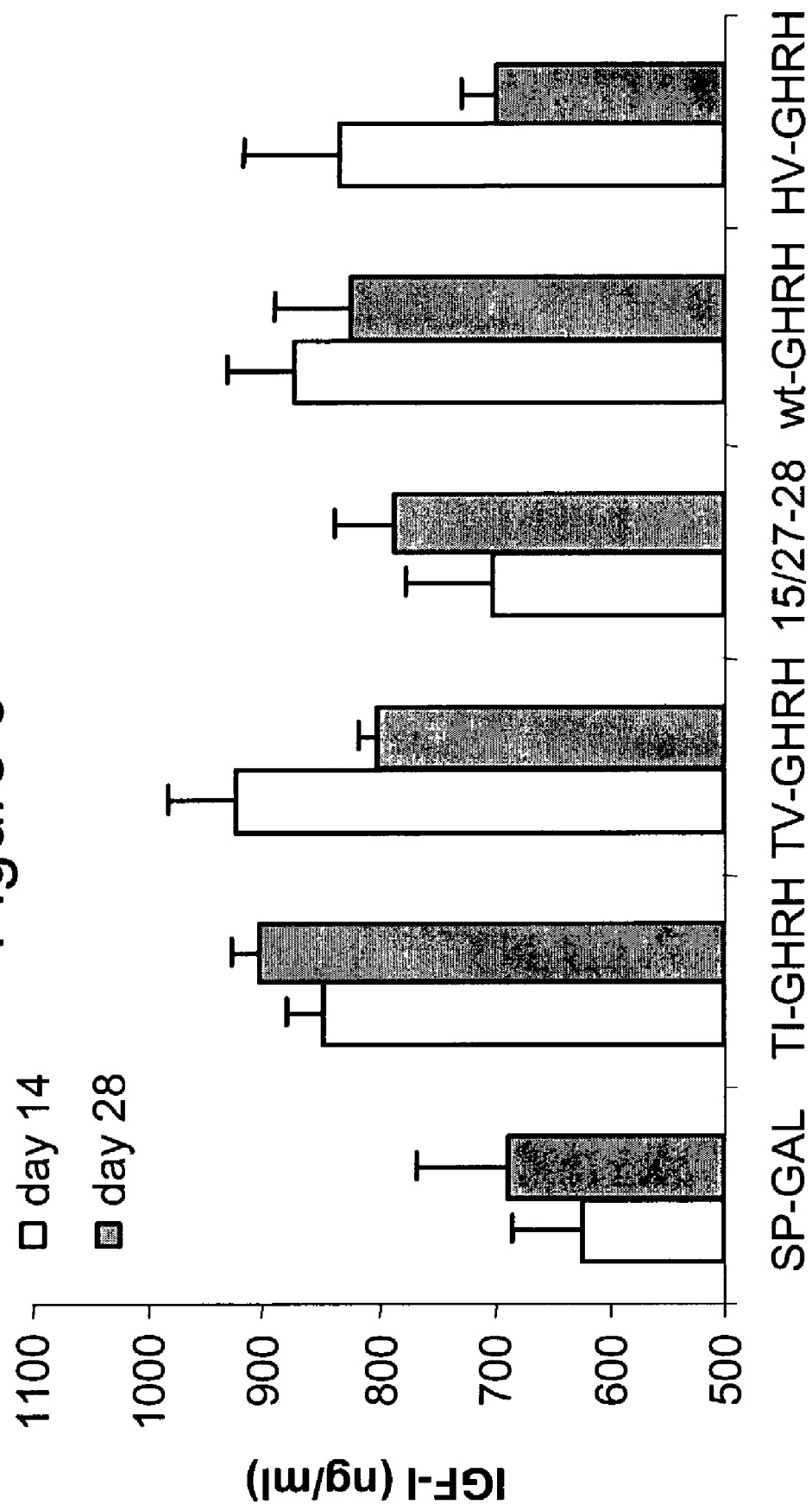
FIG. 5 shows the IGF-I levels of SCID mice that were injected with 7.5 micrograms of plasmid expressing either one of the GHRH mutants or a pSP-beta-galactosidase as control.

To test the constitutive GHRH system in vivo, 7.5 micrograms of pSP-GHRH or functional biological equivalents (FIG. 1) were delivered into SCID mice. All GHRH analog sequences were obtained by site directed mutagenesis of the porcine wild type sequence. Groups of five mice were injected with 7.5 micrograms of plasmid expressing either one of the GHRH analogs, or a pSP-beta-galactosidase as control. At 45 days post-injection, animals were analyzed by PIXImus (Draghia-Akli et al., 2002)(DEXA for mice), sacrificed, blood and organs were collected and weighed. At the end of the experiment, the TI-GHRH and HV-GHRH animals were significantly bigger than controls (FIG. 2). The body composition of the injected SCID mice was also altered. At 45 days post-injection, animals that were injected with the TI mutant had a significant increase in lean body mass of 11% versus controls, p<0.036. The HV-GHRH injected animals had a significant increase of the lean body mass of almost 5% (FIG. 3). All GHRH injected groups had larger bone areas than the control animals, up to 10.7%, in the TI-GHRH injected group, p<0.027. (FIG. 4). At 14 and 28 days post-injection, blood was collected and IGF-I levels were measured (FIG. 5). All GHRH injected groups had significantly increased IGF-I levels compared with control animals, up to p<0.005. Some groups developed neutralizing antibodies, and in these cases the IGF-I levels dropped at the second time point. The animals injected with TI-GHRH did not develop any antibodies, and their GHRH expression continued to 45 days, correlating with significant changes in their body composition.

Example 3

Inducible GHRH System In Vitro

Figure 7:
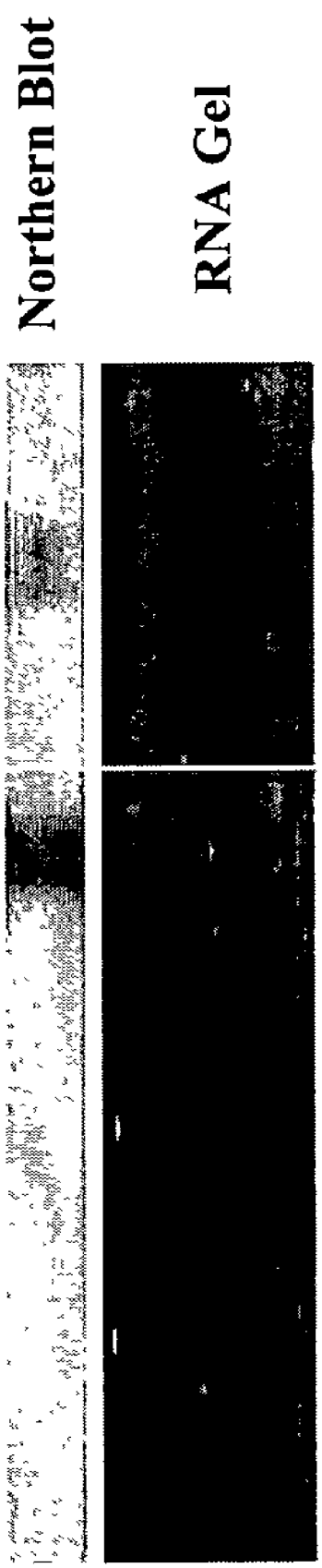
FIG. 7 shows the function of a mifepristone-dependent GHRH/GeneSwitch® system in primary myoblasts in vitro. Northern blot analysis of inducible GHRH constructs. Primary chicken myoblast cultures were obtained and transfected as described previously (Bergsma et al., 1986; Draghia-Akli et al., 1997), with 4 micrograms of a 10:1 mixture of inducible GHRH ("pGR1774") and GeneSwitch® plasmids ("pGS1633"). A Muscle specific synthetic promoter (Li et al., 1999) driven construct coding for E. coli beta-galactosidase, □βgal, is used as a negative control. As a positive control, cells were transfected with a constitutively active pSP-GHRH construct (Draghia-Akli et al., 1999). In the figure, Nt=non-transfected cells; β-gal=cells transfected with pSP-β-gal construct; SP-GHRH=cells transfected with a constitutively active GHRH construct; +MFP=mifepristone was added to the culture media; and –MFP=mifepristone was not added to the culture media. Ethidium bromide gels are included as loading controls.

To test the inducible GHRH system in vitro, primary chicken myoblasts were transfected as described previously (Bergsma et al., 1986; Draghia-Akli et al., 1997) with 4 micrograms of a mixture of the GHRH/GeneSwitch® plasmids, pGR1774 (inducible GHRH)/pGS1633 (Gene Switch®) in a 10:1 w/w ratio, which gave the best overall expression in skeletal muscle cells, and cells were allowed to differentiate into post-mitotic myotubes. At 24 and 48 hours after transfection, cells were washed in PBS, and MFP was added, where indicated, to the culture media. Media and cells were harvested 72 hours post-differentiation. 20% g of total RNA was DNase I treated, size separated in 1.5% agarose-formaldehyde gel and transferred to nylon membrane. The membranes were hybridized with a specific GHRH cDNA probe $^{32}$P-labeled by random priming. Negative controls were cells transfected by the GeneSwitch® and GHRH plasmids, but not treated with MFP, or cells transfected by the inducible GHRH plasmid alone. The positive control was cells transfected by a constitutively expressed GHRH plasmid that was driven by a synthetic muscle-specific promoter ("SP-GHRH"). GHRH transcripts of the expected size of 0.35 kb were only observed in cells transfected with the GeneSwitch®/inducible GHRH plasmids and treated with MFP, and in cells transfected with the positive control (FIG. 7). No GHRH transcripts were detected in cells not treated with MFP or in cells transfected by the inducible GHRH plasmid alone.

Example 4

Figure 8:
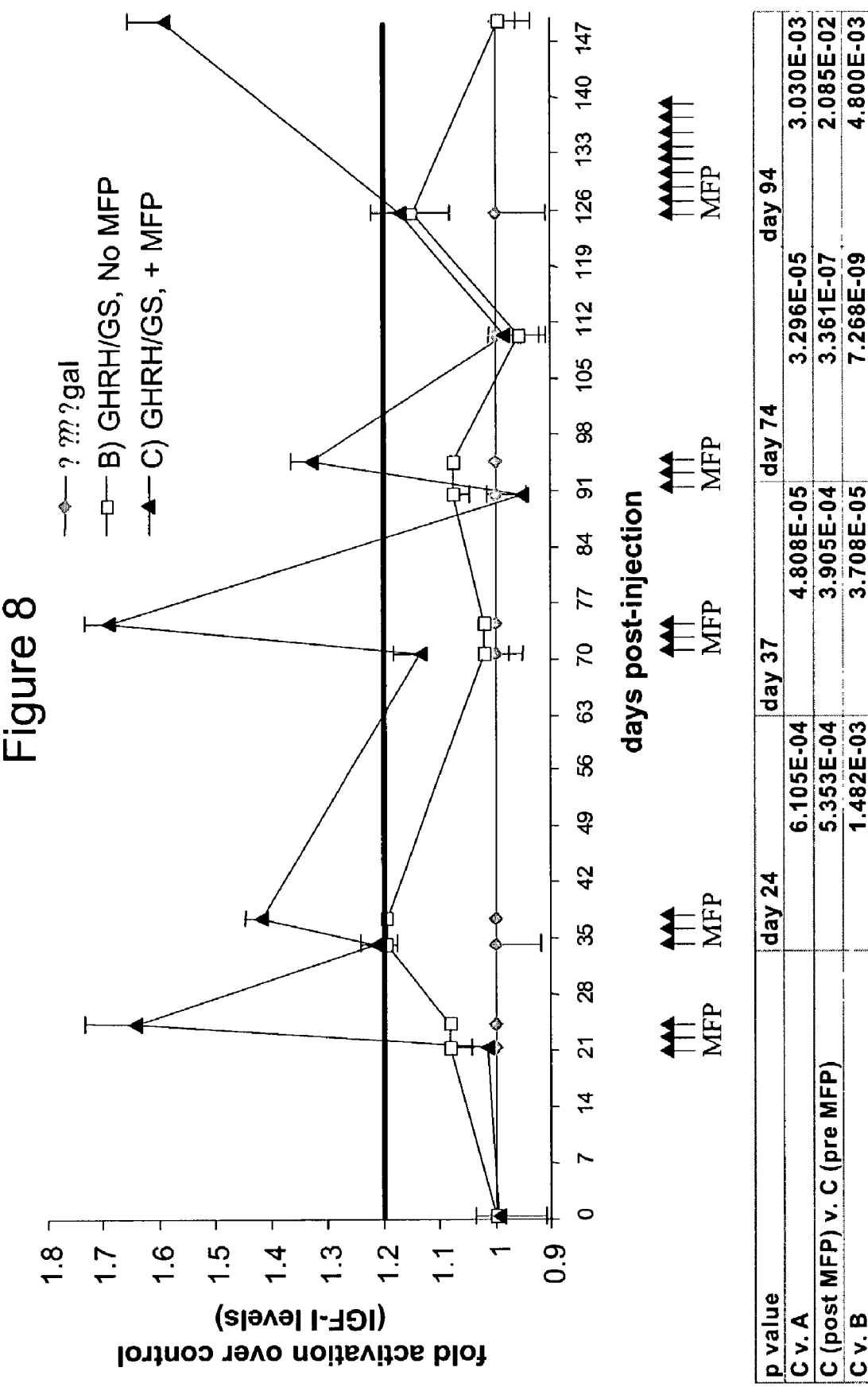
FIG. 8 shows that the mifepristone dosing induces serum IGF-I levels in SCID mice that received a single administration of GHRH/GeneSwitch® plasmids. Values are presented as fold activation over control levels. The area under the dark line represents normal variability of IGF-I levels in adult animals. The table contains the p values for the induced peaks. The p values C v. A indicate comparison between animals injected with the β-gal construct versus animals injected with the IS+MFP; C v. B. indicates comparison between animals injected with the IS with and without the MFP.

GHRH/Geneswitch® System In Vivo—Improved Body Composition and Fat Body Mass/Total Weight For the in vivo experiments, the plasmids for the GHRH/GeneSwitch® system were delivered to the muscles of SCID mice. The left tibialis anterior muscle was injected with 10 µg of a 10:1 mixture of pGR1774/pGS1633, followed by caliper electroporation (Draghia-Akli et al., 1999). At twenty-one days post-injection, animals were injected inter perineum ("i.p.") with 250 micrograms/kg of MFP for 3 days. On the fourth day, the animals were bled and serum was used to measure IGF-I levels. Mouse IGF-I was measured by heterologous, 100% cross-reacting rat radioimmunoassay. The sensitivity of the assay was 0.8 ng/ml; intra-assay and inter-assay variation was 3.4% and 4.5% respectively. Following administration of MFP for 4 consecutive days, IGF-I levels increased from 1100.86±33.67 ng/ml to 1797.28±164.96 ng/ml (p<0.0005). Significant changes in the IGF-I levels were seen when the MFP group was compared with the control group 1086.78±65.34 ng/ml, p<0.0006 (animals that received a control beta-galactosidase plasmid), 1171.79±42 ng/ml, p<0.001 (animals that received the GHRH/GeneSwitch® plasmids but were not dosed with MFP). Upon repeated administration of MFP to the animals using the same protocol followed by recovery to background 7 days over 149 days, serum IGF-I levels rose repeatedly 1.1-1.7 fold over the uninjected controls (FIG. 8). Animals induced with MFP had statistically significant higher IGF-I levels.

Figure 9:
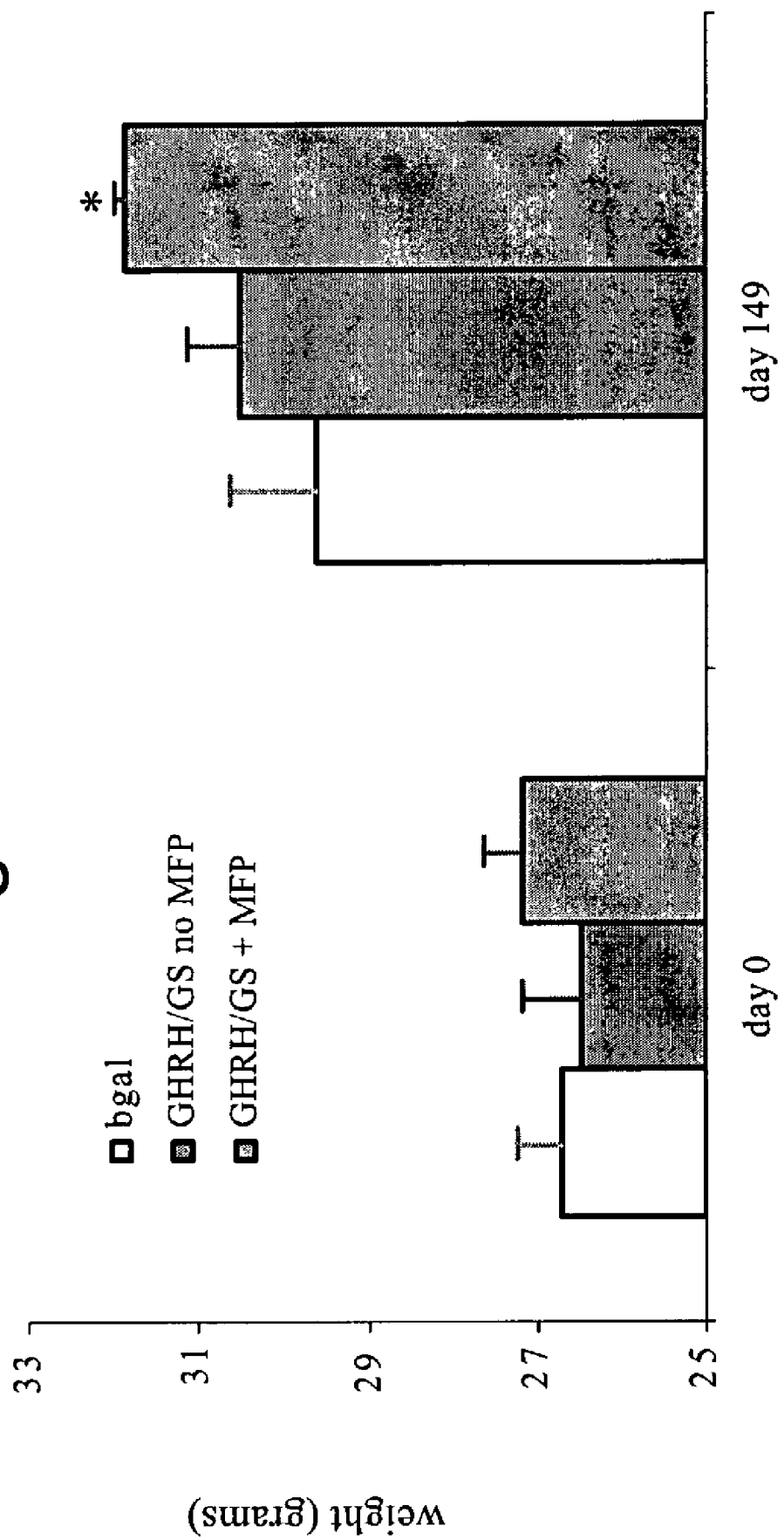
FIG. 9 shows the enhanced weight gain during a chronic 149 day MFP induction. Average weight increased in injected mice upon chronic activation of the GHRH/GeneSwitch® system (*p<0.027).
Figure 10:
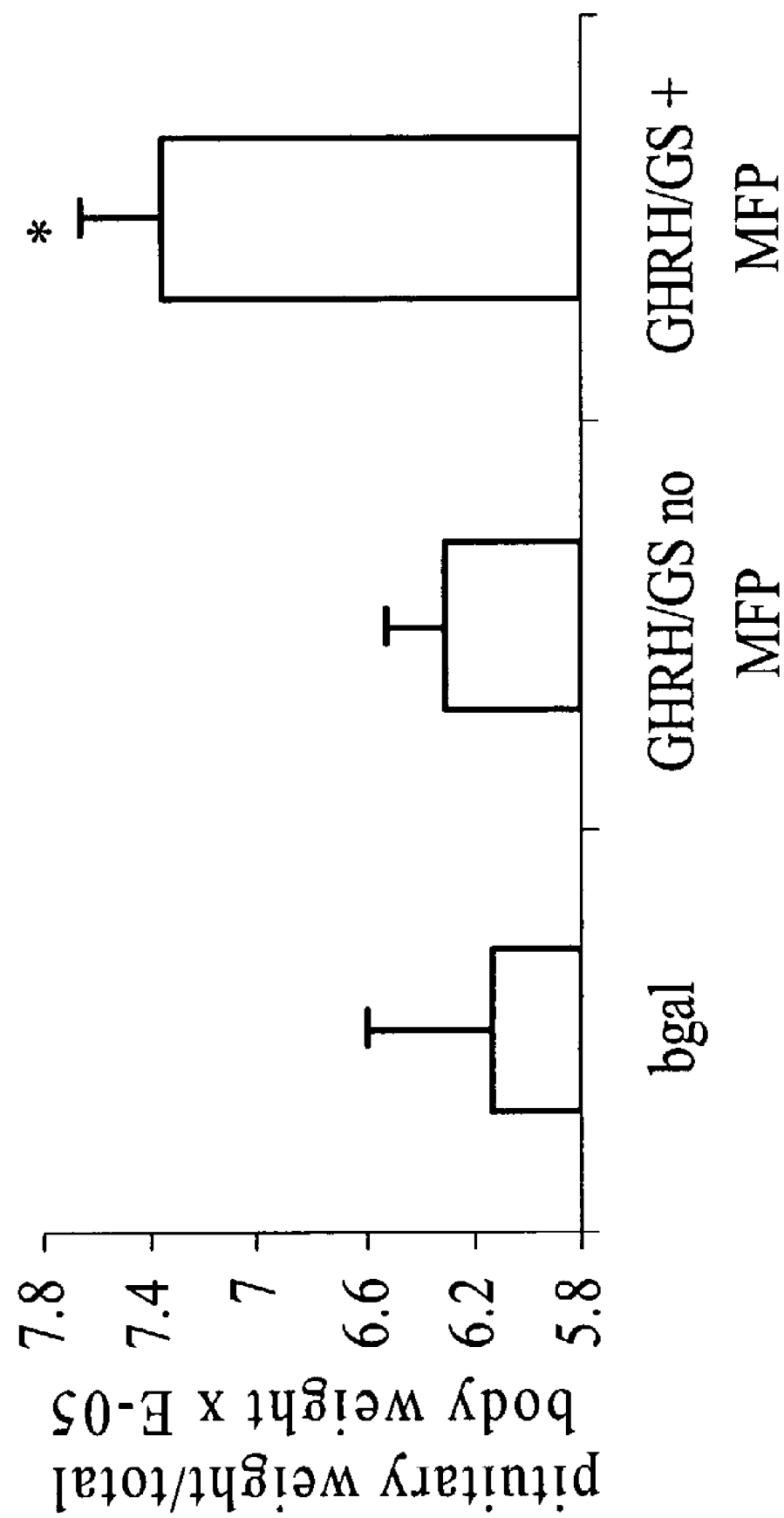
FIG. 10 shows the increase in pituitary weight with a chronic 149 day MFP induction. Pituitary weight/total body weight in +MFP injected animals (*p<0.035).
Figure 11:
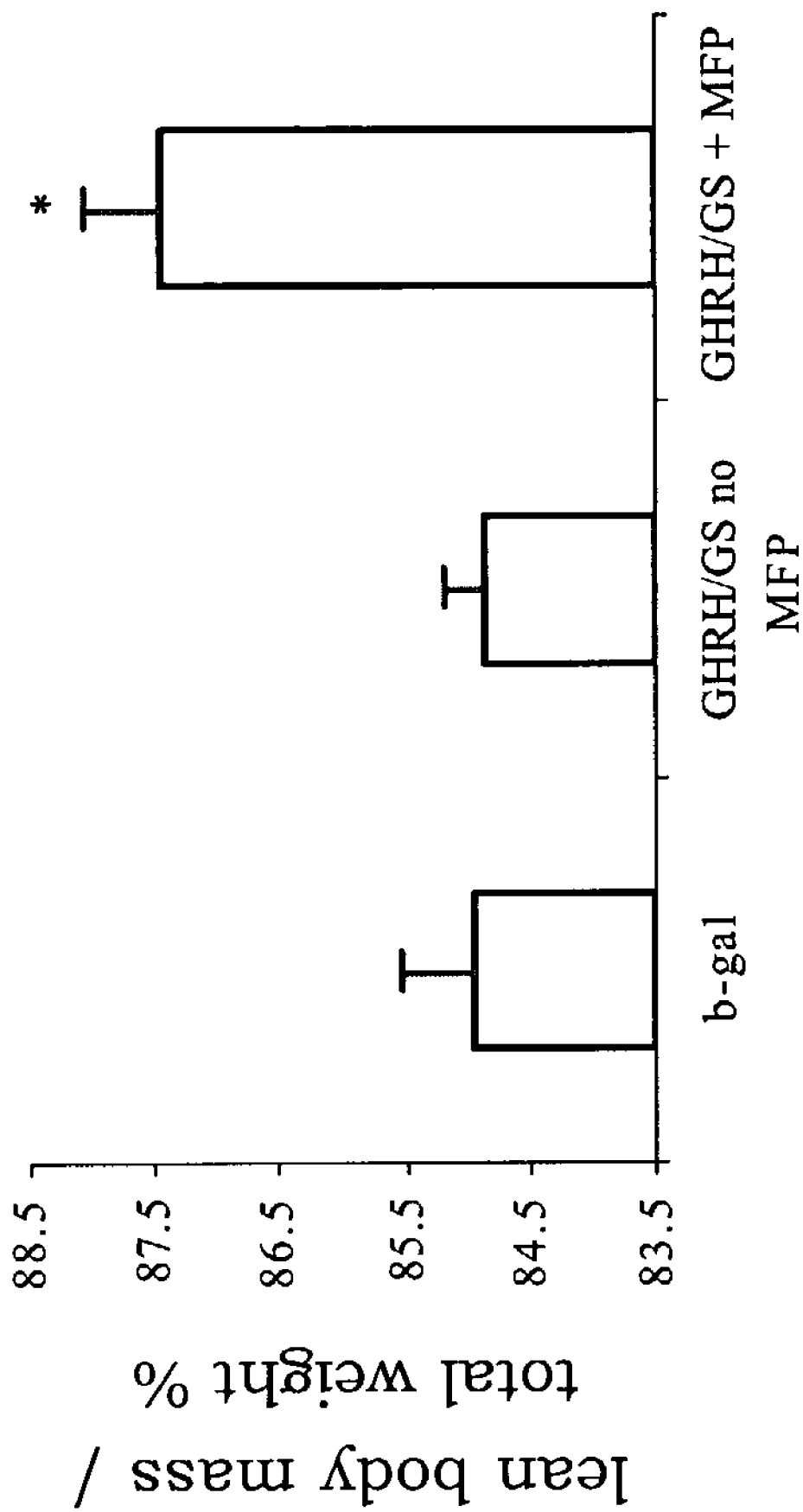
FIG. 11 shows the improved body composition in chronically induced GHRH/GeneSwitch® mice. Body composition measurements were performed either under anesthesia, at day 149 post-injection ("PIXImus") or post-mortem (organ, carcass, body fat, direct dissection of the body. Lean non-bone mass is significantly increased (*p<0.022).
Figure 12:
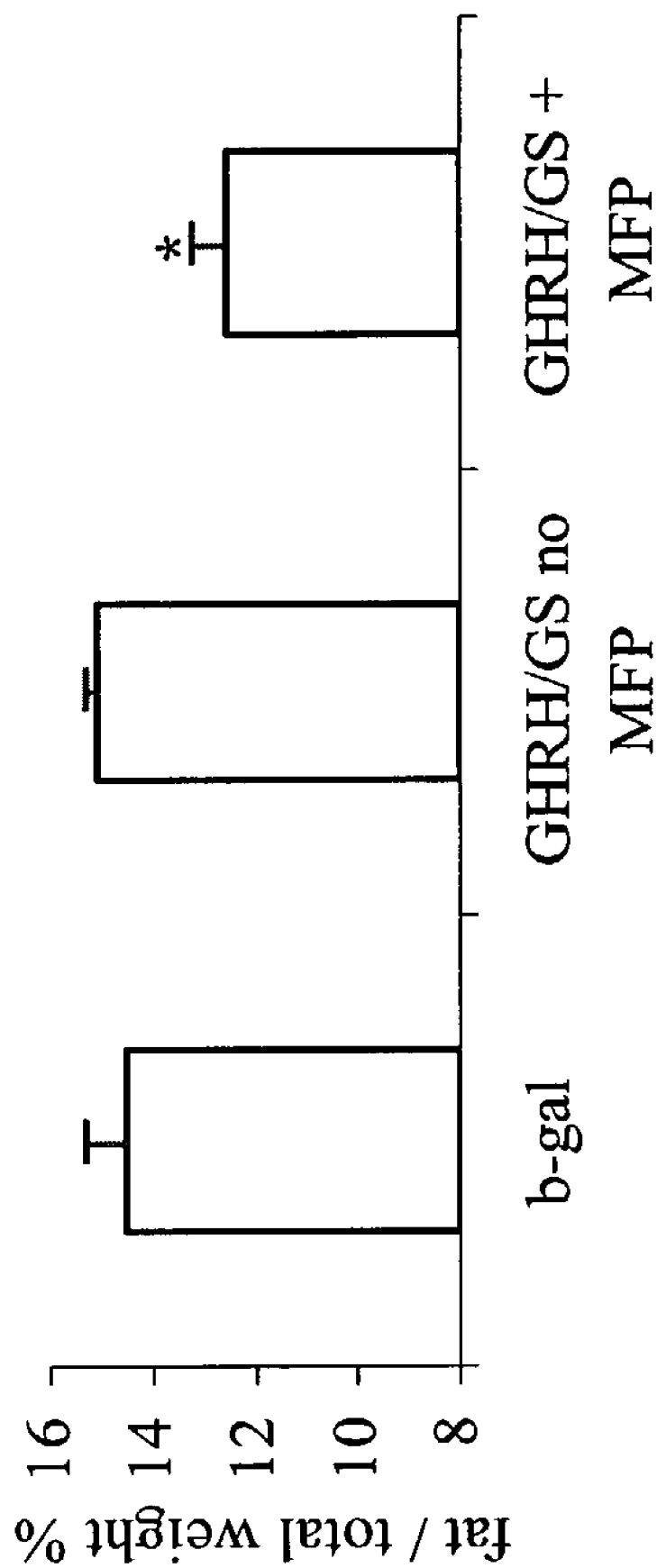
FIG. 12 shows the improved fat body mass total weight in chronically induced GHRH/GeneSwitch® mice. Fat body mass/total weight measurements were performed either under anesthesia, at day 149 post-injection ("PIXImus") or post-mortem (organ, carcass, body fat, direct dissection of the body). Fat body mass/total weight is significantly decreased in induced animals (*p<0.05).

Body weight was similar for all of the groups during the first 125 days of the study (FIG. 9). However, from day 125 to day 149, mice were dosed with MFP every day. A 7.5% increased body weight was observed in the chronically MFP-induced GHRH/GeneSwitch® animals, averaging 31.84±10.12 g (p<0.027), compared with β-gal controls, 29.62±0.98 g, and with animals that were not induced with MFP, 30.53±0.59 g. All values are average±SEM. Organs (lungs, heart, liver, kidney, stomach, intestine, adrenals, gonads, brain) were collected and weighed. No organomegaly or associated pathology was observed in any of the animals. Pituitary glands were dissected within the first minutes post-mortem, and weighed. Pituitary weight/total body weight (FIG. 10) increased upon chronic stimulation of the GHRH/GeneSwitch® by 20% ($7.35\pm0.31\times10^{-5}$), compared with β-gal controls ($6.13\pm0.46\times10^{-5}$), and animals not dosed with MFP ($6.3\pm0.22\times10^{-5}$), p<0.035. There was no significantly statistical difference between the β-gal injected animals and animals that were injected with the GHRH/GeneSwitch® system, but not given MFP. Although not to be bound by theory, the increase in pituitary weight was probably due to somatotrophs hypertrophy, as it is known that GHRH is capable of stimulating the synthesis/secretion of GH from the anterior pituitary and has a specific hypertrophic effect on somatotrophs (Morel et al., 1999; Murray et al., 2000). At the end of the experiment, body composition was analyzed in vivo, by dual-energy x-ray absorptiometry ("DEXA"), using a high resolution PIXImus scanner. Body composition studies by PIXImus (total body fat, non-bone lean tissue mass and bone mineral area, content and density) showed significant changes in chronically MFP induced animals injected with the GHRH/GeneSwitch® system. Lean body mass (non-bone) (FIG. 11) increased by 2.5% in GHRH/GeneSwitch® animals +MFP (87.44±0.65%, versus β-gal 84.94±0.6%, and no MFP animals 84.88±0.3%), p<0.022. Fat mass (FIG. 12) decreased by 2% in GHRH/GeneSwitch® animals (12.59±0.62%, versus β-gal 14.57±0.75%, and no MFP animals 15.09±0.3%), p<0.05.

Example 5

GHRH/Geneswitch® In Vivo—Increased Bone Area And Mineral Content

Figure 6:
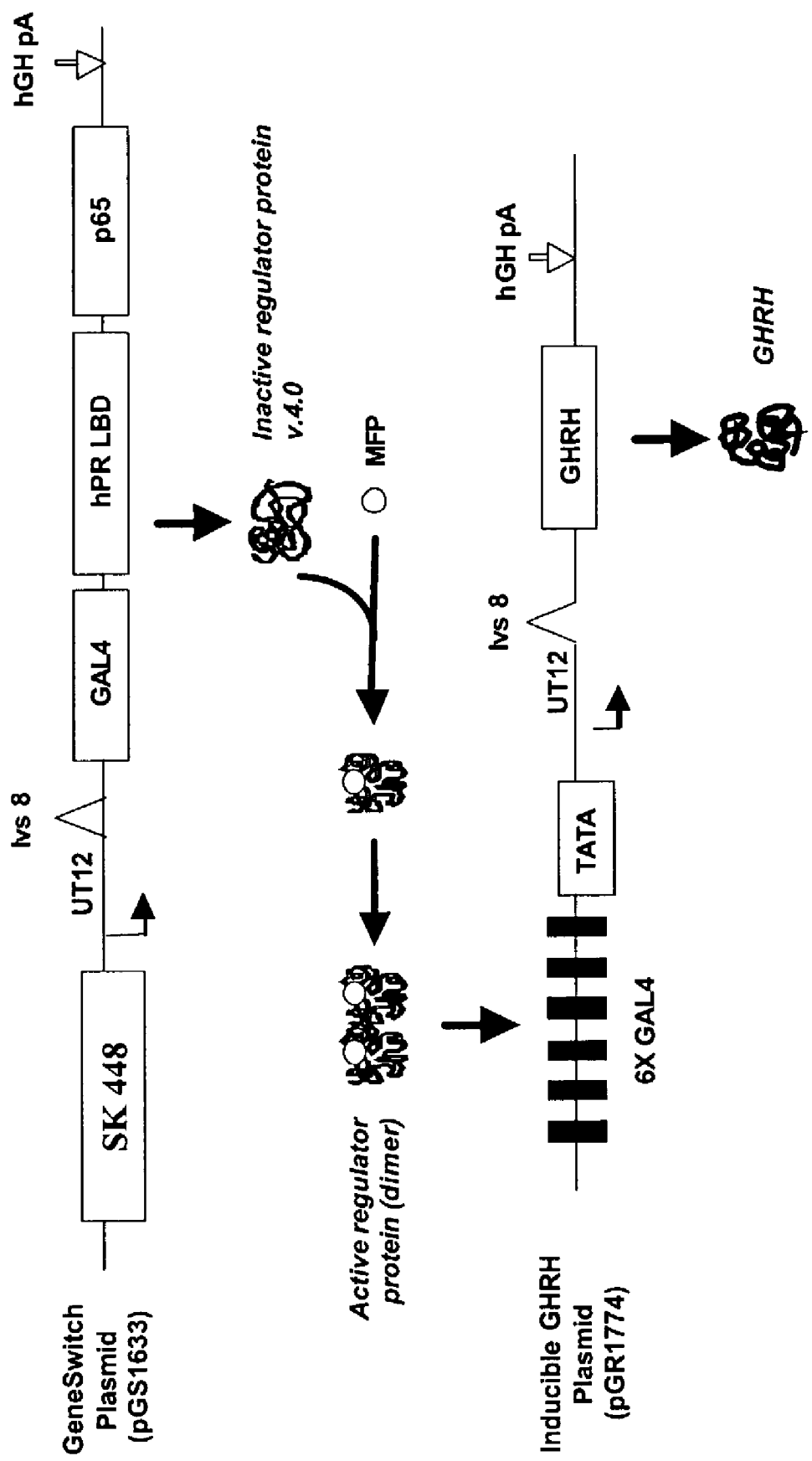
FIG. 6 shows a schematic of the mifepristone-dependent GHRH/GeneSwitch® system in primary myoblasts in vitro. Plasmid structures and schematic for how the GeneSwitch® system works are illustrated. Plasmid p1633 encodes for the GeneSwitch® regulator protein, which is a chimera of yeast GAL4 DNA binding domain ("GAL4"), truncated human progesterone receptor ligand-binding domain ("hPR LBD"), and activation domain from the p65 subunit of human NF-κB ("p65"). The protein is synthesized as an inactive monomer. Binding of mifepristone triggers a conformational change that leads to activation and dimerization. Activated homodimers bind to GAL4 sites in the inducible promoter and stimulate transcription of the GHRH gene.

One aspect of the present invention involves demonstrating that the introduction of mifepristone-inducible heterologous nucleic acid sequences encoding GHRH or functional biological equivalent thereof into the cells of subjects can lead to high levels of circulating hormones (Mir et al., 1999), without the disadvantages (e.g. high production costs, safety concerns with the virus backbone, or ex vivo manipulation) associated with viral vector delivery or organoids (Barr and Leiden, 1991; Dhawan et al., 1991; Draghia-Akli et al., 1999). In addition, the invention must demonstrate that animal growth and body composition can be efficiently regulated by mifepristone following in vivo electroporation of the GeneSwitch® technology (i.e. mifepristone-inducible heterologous nucleic acid sequences encoding GHRH or functional biological equivalent thereof) into skeletal muscle of the subject, as schematically diagrammed in FIG. 6. Enhanced biological potency, delivery and proper gene expression regulation was observed over 149 days post-injection, and effectively reduced the theoretical quantity of GHRH needed to achieve physiological levels of GH secretion when compared to the recombinant GHRH therapies. Post-injected subjects did not experience any side effects from the GeneSwitch® technology therapy. For example, mice had normal biochemical profiles, and no associated pathology or organomegaly. From a functional standpoint, the IGF-I levels increased, growth was enhanced by 7.5%, and changes in body composition (e.g. with increased lean body mass by 2.5% and decreased fat by 2%) were observed following chronic induction of the GHRH/Gene Switch system. In addition, bone mineral density increased by 6%, and the stimulation of GHRH on bone metabolism were even more remarkable. Although not to be bound by theory, the observed pituitary hypertrophy was indicative that ectopic expression of myogenic GHRH plasmids operates through the natural GH axis (stimulation of GH synthesis and secretion at the pituitary level). This long-lasting regulated therapy has the potential to replace classical GH therapy regimens and may stimulate the GH axis in a more physiologically appropriate manner. It is known that GHRH stimulates bone formation (Dubreuil et al., 1996), and the described GeneSwitch® therapy may be used to promote post-fracture bone growth.

Figure 13:
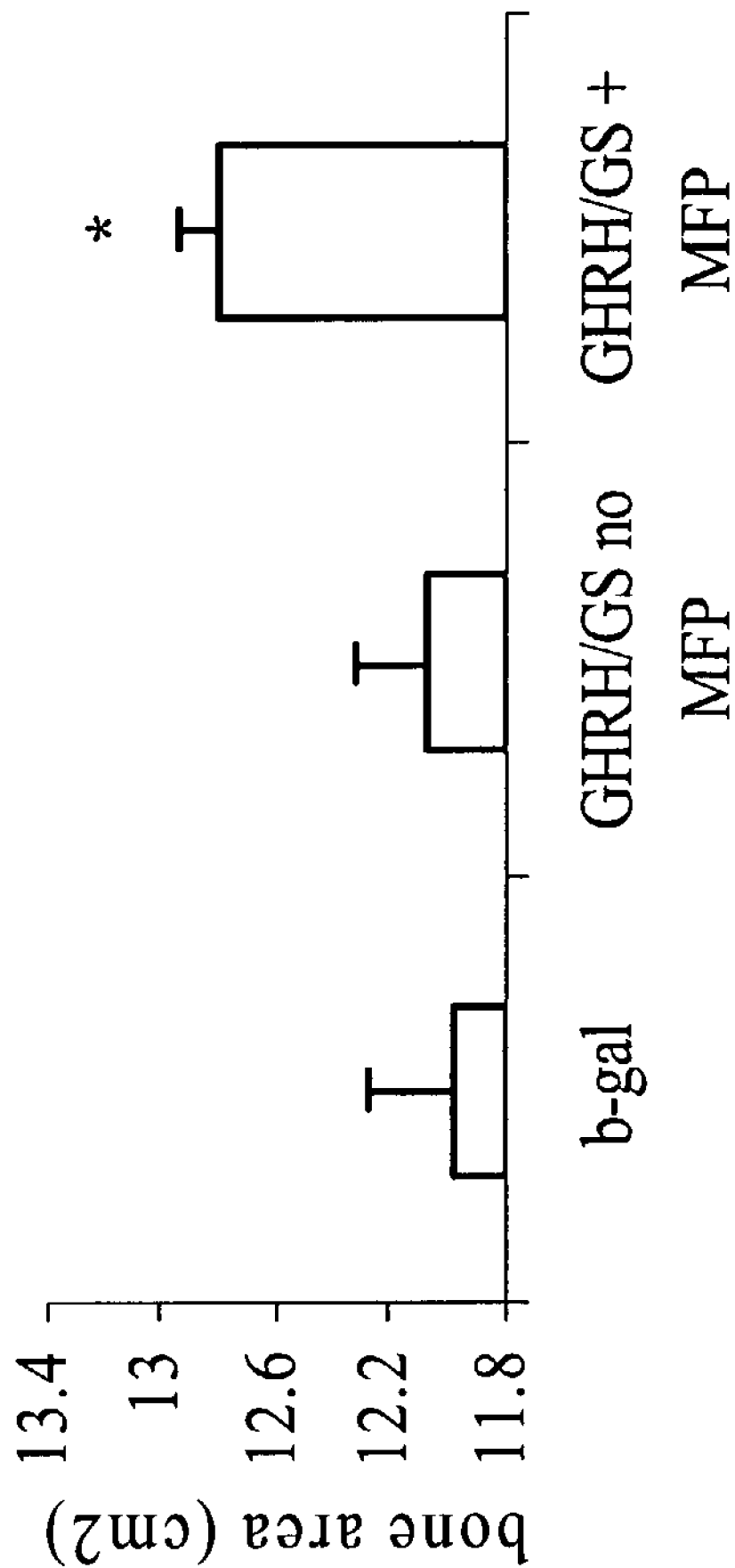
FIG. 13 shows the increased bone area in chronically induced GHRH/GeneSwitch® mice. Bone area measurements were performed either under anesthesia, at day 149 post-injection ("PIXImus") or post-mortem (organ, carcass, body fat, direct dissection of the body). Bone area is increased by PIXImus (*p<0.0006).
Figure 14:
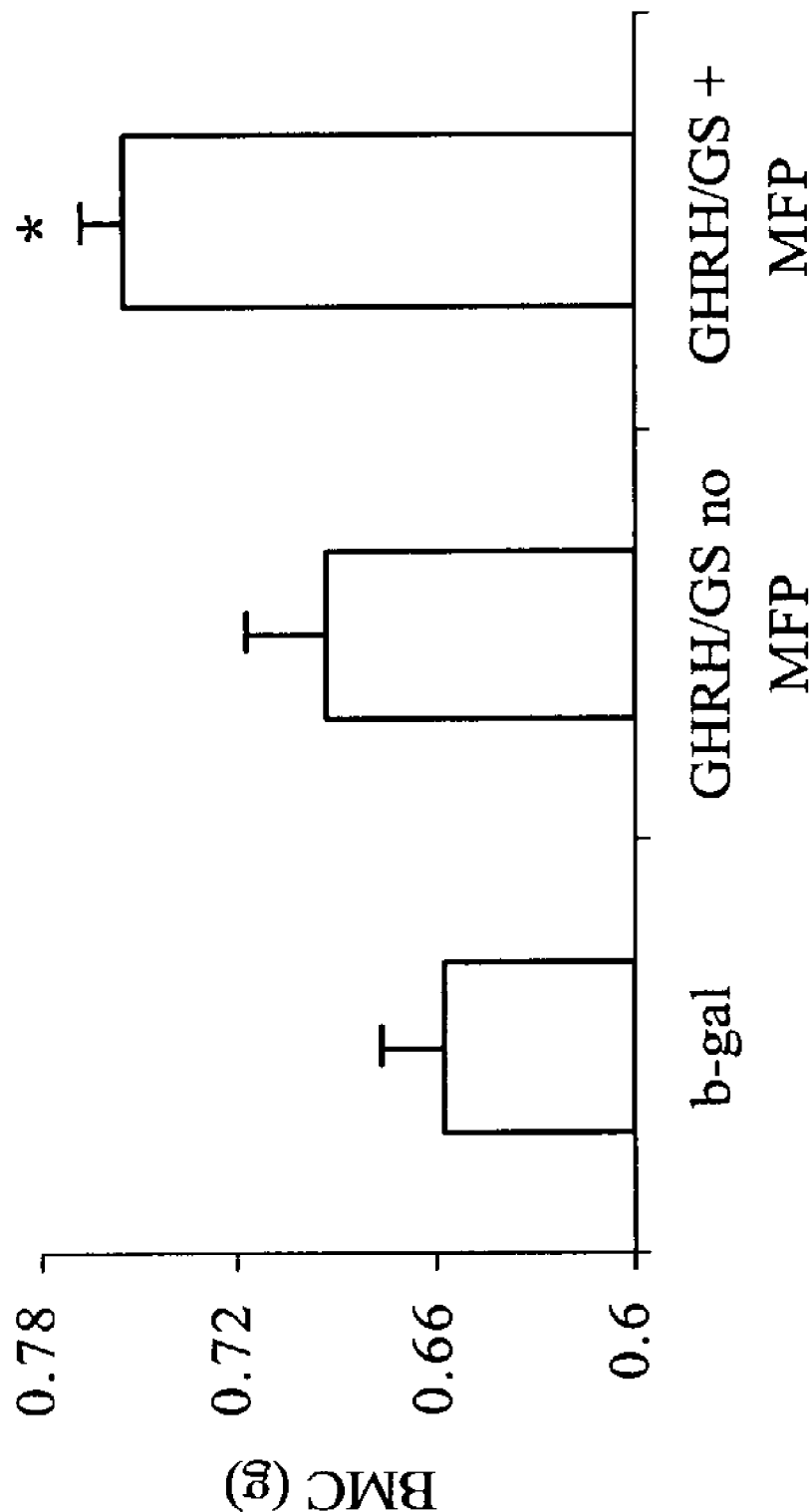
FIG. 14 shows the increased mineral content in chronically induced GHRH/GeneSwitch® mice. Bone mineral content measurements were performed either under anesthesia, at day 149 post-injection ("PIXImus") or post-mortem (organ, carcass, body fat, direct dissection of the body). Bone mineral content is increased in induced animals Q p<0.002).

Upon chronic stimulation of the GHRH/GeneSwitch® system, significant changes occurred in bone area (FIG. 13), that increased by 7%, (12.81+0.14 $cm^2$, versus B=Beta β-gal injected controls 11.98±0.3 $cm^2$, or no MFP animals 12.07±0.26 $cm^2$), p<0.0006, bone mineral content (FIG. 14) increased by 14.6% (0.755±0.012 g, versus β-gal injected controls 0.659±0.019 g, or no MFP animals 0.694±0.023 $cm^2$), p<0.002, and bone mineral density increased by 6% (0.059±0.0007 $g/cm^2$, versus β-gal injected controls 0.056±0.0009 $g/cm^2$, or no MFP animals 0.057±0.0007 $g/cm^2$), p<0.012. Practically, there is no overall difference between the β-gal injected animals and animals that were injected with the GHRH/GeneSwitch®, but were not given MFP, which supports the absence of GHRH expression by the GHRH/GeneSwitch® plasmids in the absence of MFP dosing.

Example 6

Low Voltage Electroporation Increases Plasmid Uptake and Expression In Adult Pigs Direct intra-muscular plasmid DNA injection followed by electroporation is a method for the local and controlled delivery of plasmid DNA into skeletal muscle. It has the advantage that is uses low plasmid quantities (as low as 0.1 mg in pigs), rather than the high quantities typically used with passive delivery modalities. Although not wanting to be bound by theory, the mechanism of the increased plasmid uptake by electroporation probably occurs through newly created membrane pores with or without protein active transport. It has been shown that the degree of permeabilization of the muscle cells is dependent on the electric field intensity, length of pulses, shape and type of electrodes (Bureau et al., 2000; Gilbert et al., 1997), and cell size (Somiari et al., 2000). Classical electrode configuration, plates or a pair of wire electrodes placed 4 mm apart were shown to be effective in rodents, but in large mammals as pigs or humans the increased resistance of the skin, the thickness of the subcutaneous fat tissue, and the concern for tissue damage if the intensity of the electric field would be proportionally increased, make these types of electrodes unpractical. The porcine muscle fibers are quite large and consequently more suitable for electropermeabilization than rodent muscle. Data provided herein indicate that a single injection of an optimum dosage of plasmid followed by electroporation with intramuscular applicators is sufficient to produce therapeutic plasma hormone levels in a large mammal with biologically significant effects on the body fat distribution and lean body mass of the subject.

Figure 15:
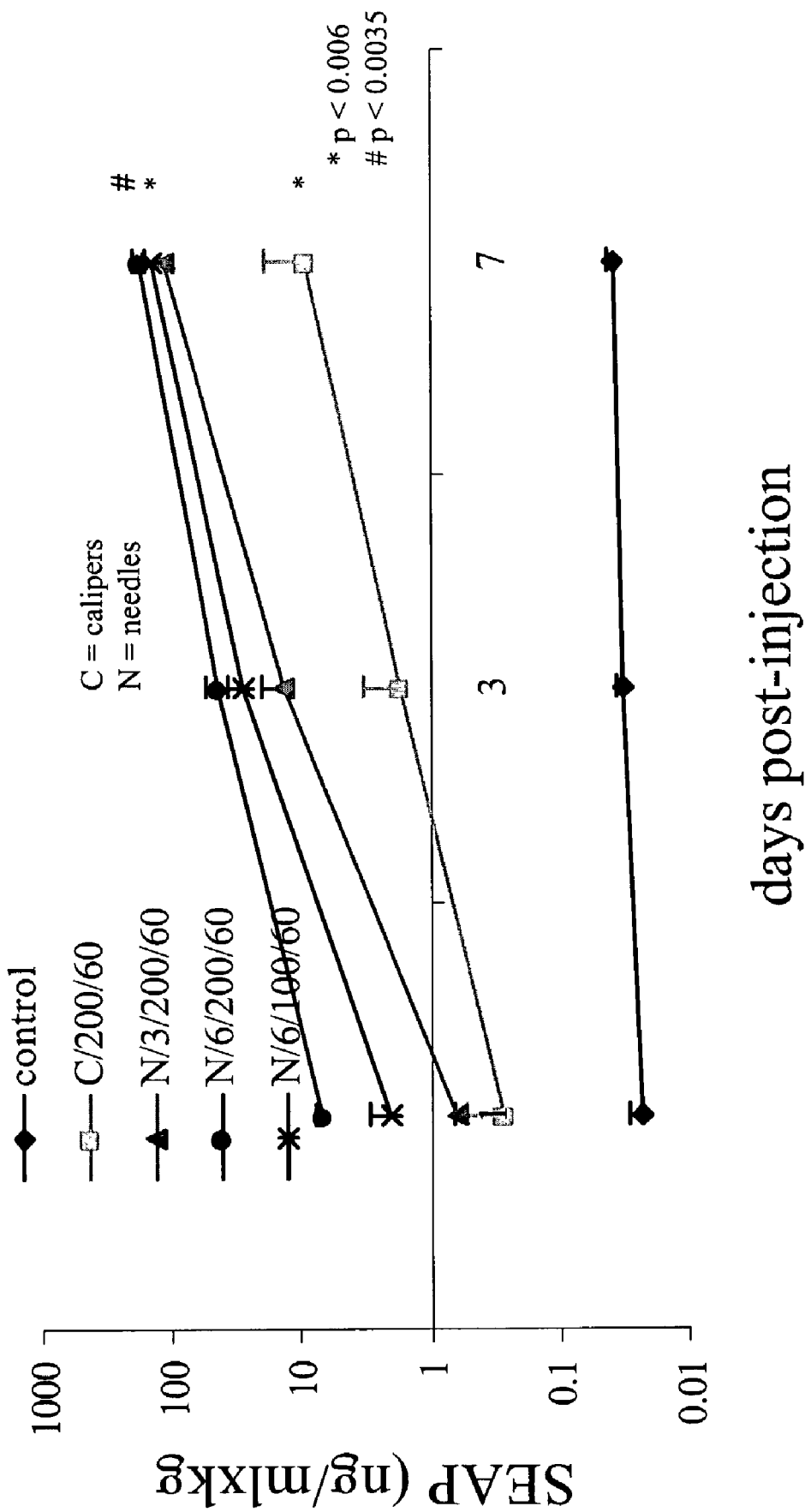
FIG. 15 shows the secreted embryonic alkaline phosphatase ("SEAP") plasma concentration in pigs at 0 to 7 days post-injection. Different needle-type electrodes were compared with calipers electrodes following the plasmid injection into the muscle. In the figure, N6=Six-needle array electrode: 21 gauge needles, 2 cm length mounted on a 1 cm—diameter array, N3=three-needle array device: two solid needles, 1 median hypodermic needle, 21 gauge, 2 cm length; and C=caliper electrode: 2 solid square plate electrodes, 1.5 cm. Voltage and number of pulses are also indicated. At 7 days post-injection p<0.006 for N3/200V/6 pulses and N6/100V/6 pulses groups, and p<0.0035 for N6/200V/6 pulses group.

External caliper electrodes and injectable electrodes were evaluated to determine the type of electrode needed to achieve a physiologically relevant level of a secreted reporter protein in 4-5 kg hybrid pigs. Reporter vectors expressing secreted embryonic alkaline phosphatase ("SEAP") were used in these studies at a dose of 2 mg pSP-SEAP/animal. Six-needle and 3-needle array electrodes were compared with standard caliper electrodes (FIG. 15). Conditions of 6 pulses, 200V/cm, 60 milliseconds/pulse, previously tested as being the most effective in pigs (Draghia-Akli et al., 1999) were applied in all tests. For the three-needle electrode, three pulses were applied in one direction, then the polarity was changed and the next three pulses were delivered in the opposite direction. SEAP values were measured at day 0, day 3 and day 7 post-injection. Seven days post-injection, the SEAP levels were 9.33±2.26 ng/(ml·kg) in plasmid-injected and caliper electroporated animals, compared to 0.02±0.005 ng/(ml·kg) in vehicle-injected animals. Using the 3-needle and 6-needle arrays, a 12.4 and 19 fold increase in SEAP values was obtained compared to caliper delivery (116.07±44.36 ng/(ml·kg), and 177.41±18.44 ng/(ml·kg), respectively). When using the same number of pulses, but lower voltage (100V/cm), and the 6-needle electrodes, the average SEAP increased to 144.64±11.82 ng/(ml·kg) after seven days. When longissimus dorsi and semitendinosus muscles were injected using similar conditions, expression in the semitendinosus muscle was slightly higher. Skin and muscle from the injected pigs were collected at the end of the experiment (at 50 days post-injection) and histologically analyzed. At 100-200 V/cm used in the injectable electrodes experiments, no skin or muscle damage was seen for any of the needle-type electrodes used.

Example 7

Increased Efficiency Using Needle-Type Electroporation Delivery for Therapeutic Proteins Not wanting to be bound by theory, growth hormone releasing hormone ("GHRH") stimulates the production and release from the anterior pituitary of growth hormone ("GH"), which in turn stimulates the production of IGF-I from the liver and other target organs (Frohman et al., 1968). In previous studies (Draghia-Akli et al., 1999), young pigs weighing 4-5 kg, were injected with 10 mg myogenic vector expressing a mutated form of GHRH, stable to proteases ("pSP-HV-GHRH") and electroporated using a caliper electrode.

Figure 16:
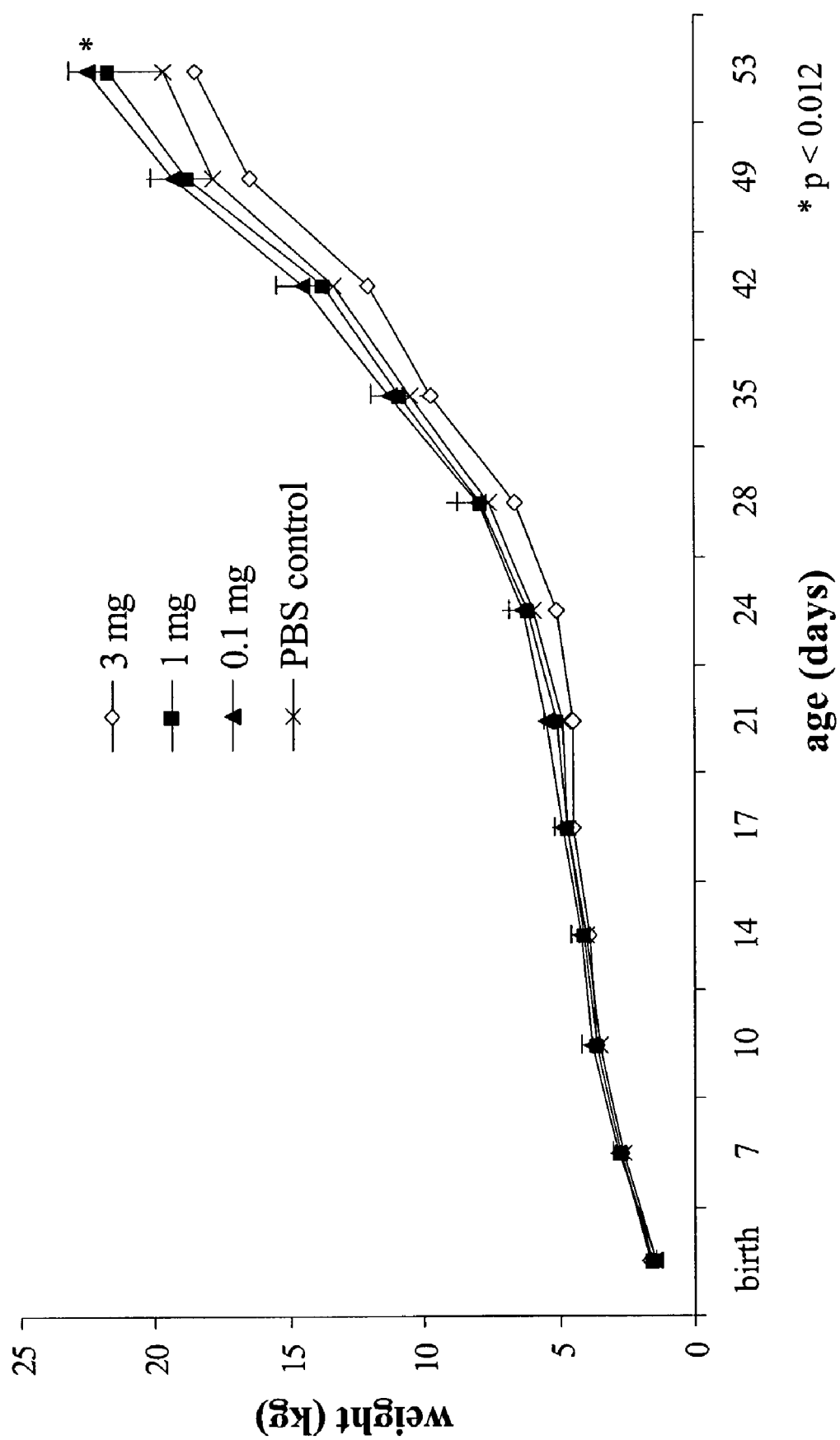
FIG. 16 shows the body weights of pigs injected at 10 days of age with 3, 1 and 0.1 mg of pSP-HV-GHRH or vehicle. The greatest weight gain was achieved by pigs injected with the lowest dose, with statistically significant differences from the controls at all time points tested (p<0.02). Values are means±s.e.m

The present invention involves determination of the best age for treatment of young pigs. Groups of 2 piglets were injected with 2 mg pSP-HV-GHRH using the 6-needle array electrodes at different time points: birth, 7, 14 and 21 days of age (FIG. 16). Each animal received one injection. The group injected at 14 days of age demonstrated the best weight gain, (statistically significant and different from PBS controls (n=3) at every time point (final weights: 25.8±1.5 kg versus 19.7±0.03 kg, p<0.013)). The next best group was injected at 7 days of age, and weighed 21.9+1.5 kg at age 50 days, p<0.02.

Figure 17:
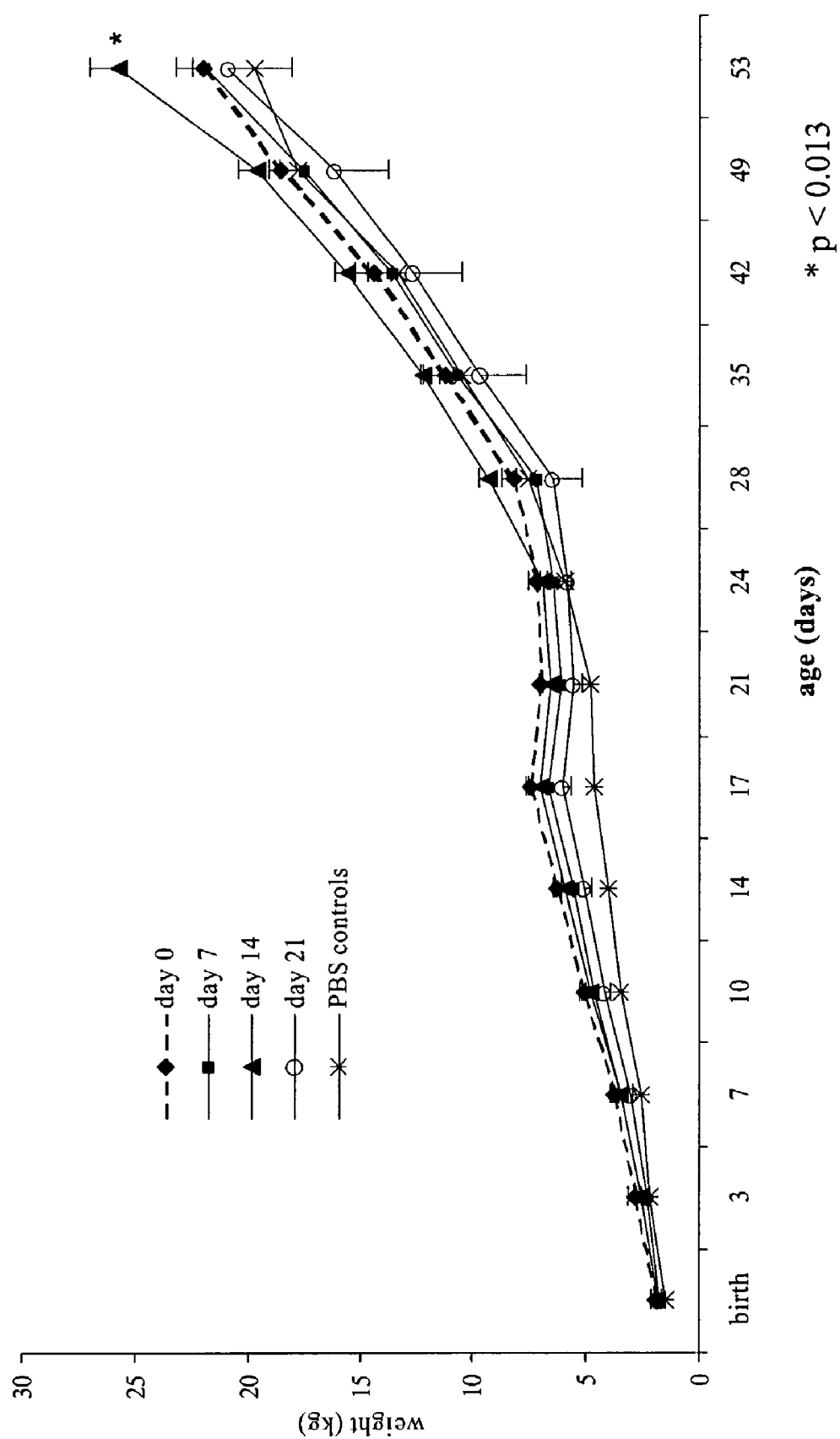
FIG. 17 shows the body weights of pigs injected with 2 milligrams of pSP-HV-GHRH at 0, 7, 14 and 21 days of age. Animal injected at 14 days of age showed the greatest weight gain, statistically different from the controls at all time points tested (p<0.02). Values are means±s.e.m.

In a parallel study, the reduction in the plasmid quantity needed to achieve improved growth and changes in the metabolic and hormonal profile of pigs was explored. Groups of two piglets each (Yorkshire×Landrace) were injected at 10 days of age with pSP-HV-GHRH (3 mg, 1 mg, 0.1 mg), and electroporated using a 6-needle array electrode (FIG. 17). The group injected with 0.1 mg of plasmid had the greater weight gain, with statistically significant differences to controls (n=3) to 50 days of age (22.4±0.8 kg versus 19.7±0.03 kg, p<0.012). One animal in the group injected at 21 days and one animal injected with the highest plasmid dose (3 mg) developed neutralizing antibodies against the mutated HV-GHRH and showed significant reduced rates of weight gain (at 50 days post-injection 15.6 kg and 15.95 kg, respectively, versus more than 21 kg for the paired animal in the same treatment group). No other group developed neutralizing antibodies. Thus, the minimal plasmid dosage (0.1 mg) and injection at optimum age using the 6-needle electrodes resulted in the best growth performances. It is noteworthy that in previous studies the inventors used 100-fold less, i.e., 10 mg pSP-HV-GHRH with the caliper electrodes to produce similar changes.

Figure 18:
FIG. 18 shows the plasma IGF-I concentration after direct intramuscular injection of the different quantities of pSP-HV-GHRH construct. Values are means±s.e.m

An indication of increased systemic levels of GHRH and GH is an increase in serum IGF-I concentration. The level of serum IGF-I started to rise at 3 days post-injection in pigs that received the 0.1 and 1 mg doses of pSP-HV-GHRH (FIG. 18). By 35 days after the injection (age of animals: 45 days), serum IGF-I concentrations were approximately 10-fold higher in pigs injected with 0.1 mg and 7-fold higher in pigs injected with 1 mg plasmid compared with controls (p<0.007 and p<0.04 respectively).

In pSP-HV-GHRH injected pigs, under optimum conditions (Table I) serum urea decreased (8.36±1.33 to 9.67±1.27 mg/ml in pSP-HV-GHRH injected pigs versus 11.14±1.9 mg/ml in controls, respectively (p<0.05), indicating decreased amino acid catabolism. Serum glucose levels were similar between the plasmid pSP-HV-GHRH injected pigs and controls; insulin levels were normal and within the control range.

TABLE 1

The plasma metabolic profile of pSP-HV-GHRH injected and control pigs.

| Group | Glucose (mg/ml) | Urea (mg/ml) | Creatine (mg/ml) | Total Protein (g/dl) |
|---|---|---|---|---|
| Age | | | | |
| Day 0 | 125.82 ± 5.64 | 8.36 ± 1.33 p < 0.01 | 0.85 ± 0.05 | 4.81 ± 0.11 |
| Day 7 | 122.43 ± 5.05 | 9.43 ± 1.67 p < 0.03 | 0.87 ± 0.04 | 5.21 ± 0.19 |

TABLE 1-continued

The plasma metabolic profile of pSP-HV-GHRH injected and control pigs.

| Group | Glucose (mg/ml) | Urea (mg/ml) | Creatine (mg/ml) | Total Protein (g/dl) |
|---|---|---|---|---|
| Day 14 | 129.54 ± 6.39 | 9.62 ± 1.72 $p < 0.02$ | 1.00 ± 0.04 | 5.22 ± 0.20 |
| Day 21 | 110.25 ± 5.02 | 13.83 ± 1.2 | 0.93 ± 0.05 | 4.81 ± 0.21 |
| Dose | | | | |
| 3 mg | 111.07 ± 3.88 | 10.50 ± 1.87 $p < 0.05$ | 0.9 ± 0.09 | 3.89 ± 0.16 |
| 1 mg | 121.63 ± 2.93 | 9.44 ± 1.07 $p < 0.02$ | 0.81 ± 0.06 | 4.11 ± 0.11 |
| 0.1 mg | 120.73 ± 2.53 | 9.67 ± 1.27 $p < 0.02$ | 0.95 ± 0.05 | 4.05 ± 0.19 |
| Control | 119.77 ± 3.67 | 12.81 ± 2.01 | 0.98 ± 0.08 | 4.00 ± 0.11 |

The fact that these animals have a normal carbohydrate metabolism is very important, as most livestock and/or patients under recombinant GH therapy develop impaired glucose metabolism and insulin resistance. Creatinine concentration (a measure of kidney function) was normal in all animals. Pigs that developed antibodies to GHRH showed a tendency to increased urea levels and decreased glucose levels.

Body composition studies by dual-energy x-ray absorptiometry (total body fat, non-bone lean tissue mass and bone mineral content), K40 potassium (lean body mass) and carcass neutron activation analysis (nitrogen) showed a proportional increase of all internal organs in GHRH injected animals (heart, lung, liver, spleen, brain, adrenals, stomach, kidney, pancreas, intestine). Nevertheless, the final body composition was different: animals injected with pSP-HV-GHRH at different ages gained proportionally less fat than controls and were leaner at the end of the study (4.34±0.04 g of fat gained/kg of fat free mass gained per day for injection at birth, 4.4±0.04 g for injection at 7 days, versus controls 5.63±0.34 g, p<0.05). Bone mineral density was higher in animals injected at 14 days after birth, and correlates with increased efficacy of the treatment: 0.363±0.005 g/cm$^2$ versus 0.329±0.003 g/cm$^2$ in controls, p<0.004.

Treated pigs did not experience any side effects from the therapy, had normal biochemical profiles, and had no associated pathology or organomegaly. From a functional standpoint, the increases in IGF-I levels and enhancement in growth and changes in body composition (with decreased fat deposition by 22%) were dramatic in extent. The effects of the stimulation of GHRH on bone metabolism were even more remarkable, with an increase in bone mineral density by 10%. These results indicate that ectopic expression of myogenic HV-GHRH vectors has the potential to replace classical GH therapy regimens and may stimulate the GH axis in a more physiologically appropriate manner. The HV-GHRH molecule, which displays a high degree of stability and GH secretory activity in pigs, may also be useful in human clinical medicine. However, a skilled artisan is aware that a minimal plasmid dose should be determined on a pertinent model and used in order to avoid the unwanted pathology associated with antibody development, and routine methods in the art and/or described herein teach how to achieve this goal.

The molecular techniques used to produce alterations in any conceivable encoded nucleic acid sequences are well established, and exemplified by the large number of scientific publications and patents in the field of molecular biology. Despite the accuracy of the molecular techniques used to create distinctive nucleic acid sequences, a skilled artisan recognizes that the expression of any given nucleic acid will influence the complex biochemistry of an entire organism. Thus, the highly predictable nature of constructing unique nucleic acid sequences must not be confused with unknown facts of an associated biological effect.

The invention described herein involves the utilization of several distinctive GHRH or analog nucleic acid sequences. Based upon the current understanding of protein-protein interactions, it is neither obvious nor possible to accurately speculate upon the in vivo parameters (e.g. half life, efficacy, post-translational modifications, etc.) of a GHRH sequence that contains a point mutation which alters a single amino acid in the polypeptide chain. As seen in the Examples provided herein, mutation of a few base pairs gave rise to GHRH mutants with significantly longer bio-availability. The endogenous GHRH has a half-life of 6-12 minutes in different species. The HV-GHRH has a half-life of 6 hours. In further analysis, the TI-GHRH (that has only two base pair difference with the HV-GHRH) has been shown to have a much higher effect in vivo on lean body mass than the HV-GHRH (from simple to double). This property was not evident in extensive in vitro studies on pituitary cell. Correspondingly, one skilled in the art would know how to perform the plasmid-mediated supplementation of GHRH or the related recombinant protein experimentation(s), characterizing variations and permutations on a unique nucleic acid sequence in a specific tissue to accurately evaluate the in vivo effect within a living organism. Therefore, the utilization of the distinctive nucleic acid sequence encoding GHRH or functional biological equivalent thereof or corresponding recombinant protein as a method to decrease body fat proportion and increase lean body mass could not have been predicted based on speculation.

Although not wanting to be bound by theory, it is believed that an increase in GHRH or functional biological equivalent will increase the GH levels to decrease body fat proportion and increase lean body mass. Hormones (e.g. GHRH and GH) often contain a complex feedback-regulated pathway. Without direct experimentation of GHRH or analogs used in gene or recombinant protein therapy, it could not have been predicted by one skilled in the art to determine which concentrations of non-native encoded sequences will yield desired results. Ideal regulation of a nucleic acid sequence encoding GHRH or functional biological equivalent thereof is further complicated by the tissue used for polynucleotide delivery, and would not have been obvious to one skilled in the art without actual experimentation with the distinctive sequence in a particular tissue. The invention described herein contains the descriptions and results of essential experimentation that explored tissue specific and inducible regulation of distinctive nucleic acid sequences that encoded GHRH or functional biological equivalent thereof, which was not obvious based upon prior art. The present invention is a significant step forward in developing non-viral therapy for large animals, including humans. In order for gene therapies to be transferred from rodents to large mammals, and ultimately to humans, it was surprising that extremely low quantities of plasmid were effective. It is shown herein that as little as 0.1 mg plasmid delivered under the proper electroporation conditions had an important biological impact that decreases the body fat proportion, increases lean body mass ("LBM"), or both of a subject. This plasmid quantity was 100 fold lower than the theoretical one, and could not have been predicted from the relative doses used in rodents (in average 1 mg/kg). Although not wanting to be bound by theory, unlike other therapies using growth factors (GH and/or IGF-I), GHRH is stimulating the endogenous secretion of hormones, and enhancing the own bio-potential of the animal, with no adverse effects. This experimental finding cannot be theoretically predicted, as the three hormones are members of the same growth axis.

The increase in lean body mass, decrease in body fat proportions, increase in bone density, and/or increase in bone rate of healing are a consequence of the GHRH molecules present in the subjects circulation, regardless of the means of the delivery. For example, one would obtain the same effect by delivering appropriate quantities of GHRH or analog thereof, outlined in FIG. 1, by classical recombinant protein therapy or nucleic acid transfer. Accordingly, successful plasmid-mediated supplementation of GHRH requires accurate delivery of the encoded sequences to the cells of a subject, resulting in expression of the gene product at levels appropriate to produce a biological effect. The duration of treatment will extend through the course of the disease symptoms, and possibly continuously. Since the method to deliver nucleic acid sequences to the cells of a subject is highly dependent on specific diseases and the encoded gene, it could not have been predicted by one skilled in the art which method and conditions are appropriate without laborious and failed experimentations. Thus, the preferred method of outlined for this invention is in vivo electroporation.

One skilled in the art readily appreciates that the present invention is well adapted to carry out the objectives and obtain the ends and advantages mentioned as well as those inherent therein. Methods, procedures, techniques, and kits described herein are presently representative of the preferred embodiments and are intended to be exemplary and are not intended as limitations of the scope. Changes therein and other uses will occur to those skilled in the art which are encompassed within the spirit of the invention or defined by the scope of the invention.

All of the methods and compositions disclosed and claimed herein can be made and executed without undue experimentation in light of the present disclosure. While the methods and compositions of this invention have been described in terms of preferred embodiments, it will be apparent to those of skill in the art that variations may be applied to the systems and compositions without departing from the concept, spirit, and scope of the invention. More specifically, it will be apparent that certain agents which are both chemically, structurally and physiologically related may be substituted for the agents descried herein while the same or similar results would be achieved. All such similar substitutes and modifications apparent to those skilled in the art are deemed to be within the spirit, and concept of the invention as defined by the appended claims.

REFERENCES CITED

The following references, to the extent that they provide exemplary procedural or other details supplementary to those set forth herein, are specifically incorporated herein by reference.

U.S. Patent Documents

U.S. Pat. No. 5,847,066 issued on Dec. 8, 1998 with Coy et al. listed as inventors.
U.S. Pat. No. 5,846,936 issued on Dec. 8, 1998 with Felix et al. listed as inventors.
U.S. Pat. No. 5,792,747 issued on Aug. 11, 1998 with Schally et al. listed as inventors.
U.S. Pat. No. 5,776,901 issued on Jul. 7, 1998 with Bowers et al. listed as inventors.
U.S. Pat. No. 5,756,264 issued on May 26, 1998 with Schwartz et al. listed as inventors.
U.S. Pat. No. 5,696,089 issued on Dec. 9, 1997 with Felix et al. listed as inventors.
U.S. Pat. No. 5,486,505 issued on Jan. 23, 1996 with Bowers et al. listed as inventors.
U.S. Pat. No. 5,292,721 issued on Mar. 8, 1994 with Boyd et al. listed as inventors.
U.S. Pat. No. 5,137,872 issued on Aug. 11, 1992 with Seely et al. listed as inventors.
U.S. Pat. No. 5,134,120 issued on Jul. 28, 1992 with Boyd et al. listed as inventors.
U.S. Pat. No. 5,084,442 issued on Jan. 28, 1992 with Felix et al. listed as inventors.
U.S. Pat. No. 5,061,690 issued on Oct. 29, 1991 with Kann et al. listed as inventors.
U.S. Pat. No. 5,036,045 issued on Jul. 30, 1991 with Thorner listed as the inventor.
U.S. Pat. No. 5,023,322 issued on Jun. 11, 1991 with Kovacs et al. listed as inventors.
U.S. Pat. No. 4,839,344 issued on Jun. 13, 1989 with Bowers et al. listed as inventors.
U.S. Pat. No. 4,410,512 issued on Oct. 18, 1983 with Bowers et al. listed as inventors.
U.S. Patent No. RE33,699 issued on Sep. 24, 1991 with Drengler listed as the inventor.
U.S. Pat. No. 4,833,166 issued on May 23, 1989 with Grosvenor et al. listed as inventors.
U.S. Pat. No. 4,228,158 issued on Oct. 14, 1980 with Momany et al. listed as inventors.
U.S. Pat. No. 4,228,156 issued on Oct. 14, 1980 with Momany et al. listed as inventors.
U.S. Pat. No. 4,226,857 issued on Oct. 7, 1980 with Momany et al. listed as inventors.
U.S. Pat. No. 4,224,316 issued on Sep. 23, 1980 with Momany et al. listed as inventors.
U.S. Pat. No. 4,223,021 issued on Sep. 16, 1980 with Momany et al. listed as inventors.
U.S. Pat. No. 4,223,020 issued on Sep. 16, 1980 with Momany et al. listed as inventors.
U.S. Pat. No. 4,223,019 issued on Sep. 16, 1980 with Momany et al. listed as inventors.
U.S. Pat. No. 4,956,288 issued on Sep. 11, 1990 with Barsoum listed as inventor.
U.S. Pat. No. 5,704,908 issued on Jan. 6, 1998 with Hofmann, et al. listed as inventors.
U.S. Pat. No. 5,702,384 issued on Dec. 30, 1997 with Umeyama, et al. listed as inventors.
U.S. Pat. No. 5,439,440 issued on Aug. 8, 1995 with Hofmann listed as inventor.
U.S. Pat. No. 5,874,534 issued on Feb. 23, 1999 with Vegeto, et al as inventors.
U.S. Pat. No. 5,935,934 issued on Aug. 10, 1999 with Vegeto, et al as inventors.
U.S. Pat. No. 5,789,215 issued on Aug. 4, 1998 with Bems, et al. as inventors.
U.S. Pat. No. 5,384,253 issued on Jan. 24, 1995 with Krzyzek, et al. as inventors.
U.S. Pat. No. 5,994,624 issued on Nov. 30, 1999 with Trolinder, et al. as inventors.
U.S. Pat. No. 5,981,274 issued on Nov. 9, 1999 with Tyrrell, et al. as inventors.

U.S. Pat. No. 5,945,100 issued on Aug. 31, 1999 with Fick as inventor.

U.S. Pat. No. 5,780,448 issued on Jul. 14, 1998 with Davis as inventor.

U.S. Pat. No. 5,736,524 issued on Apr. 7, 1998 with Content, et al. as inventors.

U.S. Pat. No. 5,702,932 issued on Dec. 30, 1997 with Hoy, et al. as inventors.

U.S. Pat. No. 5,656,610 issued on Aug. 12, 1997 with Shuler, et al. as inventors.

U.S. Pat. No. 5,589,466 issued on Dec. 31, 1996 with Felgner, et al. as inventors.

U.S. Pat. No. 5,580,859 issued on Dec. 3, 1996 with Felgner, et al. as inventors.

U.S. Pat. No. 5,610,042 issued on Mar. 11, 1997 with Chang, et al. as inventors.

U.S. Pat. No. 5,322,783 issued on Jun. 21, 1994 with Tomes, et al. as inventors.

U.S. Pat. No. 5,563,055 issued on Oct. 8, 1996 with Townsend, et al. as inventors.

U.S. Pat. No. 5,550,318 issued on Aug. 27, 1996 with Adams, et al. as inventors.

U.S. Pat. No. 5,538,877 issued on Jul. 23, 1996 with Lundquist, et al. as inventors.

U.S. Pat. No. 5,538,880 issued on Jul. 23, 1996 with Lundquist, et al. as inventors.

U.S. Pat. No. 5,302,523 issued on Apr. 12, 1994 with Coffee, et al. as inventors.

U.S. Pat. No. 5,464,765 issued on Nov. 7, 1995 with Coffee, et al. as inventors.

U.S. Pat. No. 5,591,616 issued on Jan. 7, 1997 with Hiei, et al. as inventors.

U.S. Pat. No. 4,684,611 issued on Aug. 4, 1987 with Schilperoort, et al. as inventors.

U.S. Pat. No. 4,952,500 issued on Aug. 28, 1990 with Finnerty, et al. as inventors.

WO 94/09699

WO95/06128;

REFERENCE LIST

Abruzzese, R. V., D. Godin, M. Burcin, V. Mehta, M. French, Y. Li, B. W. O'Malley, and J. L. Nordstrom. 1999. Ligand-dependent regulation of plasmid-based transgene expression in vivo. Hum. Gene Ther. 10:1499-1507.

Abruzzese, R. V., D. Godin, V. Mehta, J. L. Perrard, M. French, W. Nelson, G. Howell, M. Coleman, B. W. O'Malley, and J. L. Nordstrom. 2000. Ligand-dependent regulation of vascular endothelial growth factor and erythropoietin expression by a plasmid-based autoinducible GeneSwitch system. Mol. Ther. 2:276-287.

Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bemabeu. 1996. Cloning of the human platelet endothelial cell adhesion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucleic Acids Res. 20:4795-4801.

Argente, J., J. Pozo, and J. A. Chowen. 1996. The growth hormone axis: control and effects. Hormone Research 45 Suppl 1:9-11.

Barr, E. and J. M. Leiden. 1991. Systemic delivery of recombinant proteins by genetically modified myoblasts. Science 254:1507-1509.

Bercu, B. B., R. F. Walker 1997. Growth Hormone Secretagogues In Children With Altered Growth. Acta Paediatrica 86:102-106.

Bergsma, D. J., J. M. Grichnik, L. M. Gossett, and R. J. Schwartz. 1986. Delimitation and characterization of cis-acting DNA sequences required for the regulated expression and transcriptional control of the chicken skeletal alpha-actin gene. Molecular & Cellular Biology 6:2462-2475.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Blethen, S. L. 1995. Complications of growth hormone therapy in children. Curr. Opin. Pediatr. 7:466-471.

Blethen, S. L. and A. C. Rundle. 1996. Slipped capital femoral epiphysis in children treated with growth hormone. A summary of the National Cooperative Growth Study experience. Horm. Res. 46:113-116.

Bohlen, P., F. Esch, P. Brazeau, N. Ling, and R. Guillemin. 1983. Isolation and characterization of the porcine hypothalamic growth hormone releasing factor. Biochem. Biophys. Res. Commun. 116:726-734.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Bureau, M. F., J. Gehl, V. Deleuze, L. M. Mir, and D. Scherman. 2000. Importance of association between permeabilization and electrophoretic forces for intramuscular DNA electrotransfer. Biochim. Biophys. Acta 1474:353-359.

Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U.S.A 94:3596-3601.

Chen, C. and H. Okayama. 1987. High-efficiency transformation of mammalian cells by plasmid DNA. Mol. Cell Biol. 7:2745-2752.

Chevalier, R. L., S. Goyal, A. Kim, A. Y. Chang, D. Landau, and D. LeRoith. 2000. Renal tubulointerstitial injury from ureteral obstruction in the neonatal rat is attenuated by IGF-1. Kidney Int. 57:882-890.

Cocea, L. 1997. Duplication of a region in the multiple cloning site of a plasmid vector to enhance cloning-mediated addition of restriction sites to a DNA fragment. Biotechniques 23:814-816.

Cohn, S. H., A. N. Vaswani, S. Yasumura, K. Yuen, and K. J. Ellis. 1984. Improved models for determination of body fat by in vivo neutron activation. Am. J. Clin. Nutr. 40:255-259.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. Journal of Clinical Endocrinology & Metabolism 76:134-138.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. [Review]. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dhawan, J., L. C. Pan, G. K. Pavlath, M. A. Travis, A. M. Lanctot, and H. M. Blau. 1991. Systemic delivery of human growth hormone by injection of genetically engineered myoblasts. Science 254:1509-1512.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U.S.A 82:8325-8329.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., X. G. Li, and R. J. Schwartz. 1997. Enhanced growth by ectopic expression of growth hormone releasing hormone using an injectable myogenic vector. nature biotechnology 15:1285-1289.

Draghia-Akli, R., P. B. Malone, L. A. Hill, K. M. Ellis, R. J. Schwartz, and J. L. Nordstrom. 2002. Enhanced animal growth via ligand-regulated GHRH myogenic-injectable vectors. FASEB J. 16:426-428.

Dubreuil, P., T. Abribat, B. Broxup, and P. Brazeau. 1996. Long-term growth hormone-releasing factor administration on growth hormone, insulin-like growth factor-I concentrations, and bone healing in the Beagle. Canadian Journal of Veterinary Research 60:7-13.

Dubreuil, P., Y. Couture, G. Pelletier, D. Petitclerc, L. Delorme, H. Lapierre, P. Gaudreau, J. Morisset, and P. Brazeau. 1990a. Effect of long-term administration of porcine growth hormone-releasing factor and(or) thyrotropin-releasing factor on growth hormone, prolactin and thyroxine concentrations in growing pigs. J. Anim Sci. 68:95-107.

Dubreuil, P., D. Petitclerc, G. Pelletier, P. Gaudreau, C. Farmer, Mowles, TF, and P. Brazeau. 1990b. Effect of dose and frequency of administration of a potent analog of human growth hormone-releasing factor on hormone secretion and growth in pigs. Journal of Animal Science 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. Journal of Clinical Endocrinology & Metabolism 75:1115-1120.

Evans, W. S., S. M. Anderson, L. T. Hull, P. P. Azimi, C. Y. Bowers, and J. D. Veldhuis. 2001. Continuous 24-hour intravenous infusion of recombinant human growth hormone (GH)-releasing hormone-(1-44)-amide augments pulsatile, entropic, and daily rhythmic GH secretion in postmenopausal women equally in the estrogen-withdrawn and estrogen-supplemented states. J. Clin. Endocrinol. Metab 86:700-712.

Evans, W. S., M. L. Vance, D. L. Kaiser, R. P. Sellers, J. L. Borges, T. R. Downs, L. A. Frohman, J. Rivier, W. Vale, and M. O. Thorner. 1985. Effects of intravenous, subcutaneous, and intranasal administration of growth hormone (GH)-releasing hormone-40 on serum GH concentrations in normal men. Journal of Clinical Endocrinology & Metabolism 61:846-850.

Fechheimer, M., J. F. Boylan, S. Parker, J. E. Sisken, G. L. Patel, and S. G. Zimmer. 1987. Transfection of mammalian cells with plasmid DNA by scrape loading and sonication loading. Proc. Natl. Acad. Sci. U.S.A 84:8463-8467.

Fewell, J. G., F. MacLaughlin, V. Mehta, M. Gondo, F. Nicol, E. Wilson, and L. C. Smith. 2001. Gene therapy for the treatment. of hemophilia B using PINC-formulated plasmid delivered to muscle with electroporation. Mol. Ther. 3:574-583.

Frohman, L. A., T. R. Downs, E. P. Heimer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., L. L. Nernardis, and K. J. Kant. 1968. Hypothalamic stimulation of growth hormone secretion. Science 162:580-582.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and. 1995. The insulin gene promoter. A simplified nomenclature. Diabetes 44:1002-1004.

Gesundheit, N. and J. K. Alexander. 1995. Endocrine Therapy with Recombinant Hormones and Growth Factors. In: B. D. Weintraub (Ed.) Molecular Endocrinology: Basic Concepts and Clinical Correlations. pp. 491-507. Raven Press, Ltd., New York.

Gilbert, R. A., M. J. Jaroszeski, and R. Heller. 1997. Novel electrode designs for electrochemotherapy. Biochim. Biophys. Acta 1334:9-14.

Gopal, T. V. 1985. Gene transfer method for transient gene expression, stable transformation, and cotransformation of suspension cell cultures. Mol. Cell Biol. 5:1188-1190.

Graham, F. L. and A. J. van der Eb. 1973. Transformation of rat cells by DNA of human adenovirus 5. Virology 54:536-539.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Hafez, I. M., N. Maurer, and P. R. Cullis. 2001. On the mechanism whereby cationic lipids promote intracellular delivery of polynucleic acids. Gene Ther. 8:1188-1196.

Hamm, A., N. Krott, I. Breibach, R. Blindt, and A. K. Bosserhoff. 2002. Efficient transfection method for primary cells. Tissue Eng 8:235-245.

Harland, R. and H. Weintraub. 1985. Translation of mRNA injected into Xenopus oocytes is specifically inhibited by antisense RNA. J. Cell Biol. 101:1094-1099.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Horlick, R. A. and P. A. Benfield. 1989. The upstream muscle-specific enhancer of the rat muscle creatine kinase gene is composed of multiple elements. Mol. Cell Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Johnson, N. F., M. D. Hoover, D. G. Thomassen, Y. S. Cheng, A. Dalley, and A. L. Brooks. 1992. In vitro activity of silicon carbide whiskers in comparison to other industrial fibers using four cell culture systems. Am. J. Ind. Med. 21:807-823.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Kiamut, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10: 193-205.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Lee, S. H., W. Wang, S. Yajima, P. A. Jose, and M. M. Mouradian. 1997. Tissue-specific promoter usage in the DIA dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Chamsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. nature biotechnology 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lucas, M. L., L. Heller, D. Coppola, and R. Heller. 2002. IL-12 plasmid delivery by in vivo electroporation for the successful treatment of established subcutaneous B16.F1O melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macejak, D. G. and P. Sarnow. 1991. Internal initiation of translation mediated by the 5' leader of a cellular mRNA. Nature 353:90-94.

Madry, H., R. Reszka, J. Bohlender, and J. Wagner. 2001. Efficacy of cationic liposome-mediated gene transfer to mesangial cells in vitro and in vivo. J. Mol. Med. 79:184-189.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Mir, L. M., M. F. Bureau, J. Gehl, R. Rangara, D. Rouy, J. M. Caillaud, P. Delaere, D. Branellec, B. Schwartz, and D. Scherman. 1999. High-efficiency gene transfer into skeletal muscle mediated by electric pulses. Proc. Natl. Acad. Sci. U.S.A 96:4262-4267.

Morel, G., R. Gallego, L. Boulanger, E. Pintos, T. Garcia-Caballero, and P. Gaudreau. 1999. Restricted presence of the growth hormone-releasing hormone receptor to somatotropes in rat and human pituitaries. Neuroendocrinology 70:128-136.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., A. Nakamura, and H. M. Park. 1998. In vivo electroporation: A powerful and convenient means of nonviral gene transfer to tissues of living animals. Int. J. Mol. Med. 1:55-62.

Murray, R. A., H. G. Maheshwari, E. J. Russell, and G. Baumann. 2000. Pituitary hypoplasia in patients with a mutation in the growth hormone-releasing hormone receptor gene. AJNR Am. J. Neuroradiol. 21:685-689.

Murray, R. D. and S. M. Shalet. 2000. Growth hormone: current and future therapeutic applications. Expert. Opin. Pharmacother. 1:975-990.

Nabel, E. G., G. Plautz, F. M. Boyce, J. C. Stanley, and G. J. Nabel. 1989. Recombinant gene expression in vivo within endothelial cells of the arterial wall. Science 244: 1342-1344.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhlrmann, H. Liang, M. Oakley, A. Taye, B. K. Sim, and S. L. Hoffman. 2001. Codon optimization of gene fragments encoding Plasmodium falciparum merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Omirulleh, S., M. Abraham, M. Golovkin, I. Stefanov, M. K. Karabaev, L. Mustardy, S. Morocz, and D. Dudits. 1993. Activity of a chimeric promoter with the doubled CaMV 35S enhancer element in protoplast-derived cells and transgenic plants in maize. Plant Mol. Biol. 21:415-428.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potrykus, I., J. Paszkowski, M. W. Saul, J. Petruska, and R. D. Shillito. 1985. Molecular and general genetics of a hybrid foreign gene introduced into tobacco by direct gene transfer. Mol. Gen. Genet. 199:169-177.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U.S.A 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. Journal of Molecular & Cellular Cardiology 26:1393-1401.

Raghavachari, N. and W. E. Fahl. 2002. Targeted gene delivery to skin cells in vivo: a comparative study of liposomes and polymers as delivery vehicles. J. Pharm. Sci. 91:615-622.

Rippe, R. A., D. A. Brenner, and H. L. Leffert. 1990. DNA-mediated gene transfer into adult rat hepatocytes in primary culture. Mol. Cell Biol. 10:689-695.

Sambrook, J., E. F. Fritsch, and T. Maniatis. 1989. Molecular Cloning—A Laboratory Manual. Cold Spring Harbor Laboratory Press, Cold Spring Harbor, N.Y.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10:187-192.

Skroch, P., C. Buchman, and M. Karin. 1993. Regulation of human and yeast metallothionein gene transcription by heavy metal ions. Prog. Clin. Biol. Res. 380:113-28.:113-128.

Smith, L. C. and J. L. Nordstrom. 2000. Advances in plasmid gene delivery and expression in skeletal muscle. Curr. Opin. Mol. Ther. 2:150-154.

Somiari, S., J. Glasspool-Malone, J. J. Drabick, R. A. Gilbert, R. Heller, M. J. Jaroszeski, and R. W. Malone. 2000. Theory and in vivo application of electroporative gene delivery. Mol. Ther. 2:178-187.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J. Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Thorner, M. O., M. L. Vance, W. S. Evans, A. D. Rogol, J. Rivier, W. Vale, Blizzard, and RM. 1986. CLINICAL STUDIES WITH GHRH IN MAN. Hormone Research 24:91-98.

Thorner, M. O., M. L. Vance, M. L. Hartman, R. W. Holl, W. S. Evans, J. D. Veldhuis, E. Van Cauter, G. Copinschi, and C. Y. Bowers. 1990. Physiological role of somatostatin on growth hormone regulation in humans. Metabolism: Clinical & Experimental 39:40-42.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Toner, M. S., R. H. King, F. R. Dunshea, H. Dove, and C. S. Atwood. 1996. The effect of exogenous somatotropin on lactation performance of first-litter sows. J. Anim Sci. 74:167-172.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2(XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion [see comments]. Circulation 94:3281-3290.

Tur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

Vance, M. L. 1990. Growth-hormone-releasing hormone. [Review] [52 refs]. Clinical Chemistry 36:415-420.

Vance, M. L., D. L. Kaiser, W. S. Evans, R. Furlanetto, W. Vale, J. Rivier, and M. O. Thorner. 1985a. Pulsatile growth hormone secretion in normal man during a continuous 24-hour infusion of human growth hormone releasing factor (1-40). Evidence for intermittent somatostatin secretion. J. Clin. Invest. 75:1584-1590.

Vance, M. L., D. L. Kaiser, W. S. Evans, M. O. Thorner, R. Furlanetto, J. Rivier, W. Vale, G. Perisutti, and L. A. Frohman. 1985b. Evidence for a limited growth hormone (GH)-releasing hormone (GHRH)-releasable quantity of GH: effects of 6-hour infusions of GHRH on GH secretion in normal man. Journal of Clinical Endocrinology & Metabolism 60:370-375.

Vegeto, E., G. F. Allan, W. T. Schrader, M. J. Tsai, D. P. McDonnell, and B. W. O'Malley. 1992. The mechanism of RU486 antagonism is dependent on the conformation of the carboxy-terminal tail of the human progesterone receptor. Cell 69:703-713.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two years of replacement therapy in adults with growth hormone deficiency. Clin. Endocrinol. (Oxf) 47:485-494.

Vilquin, J. T., P. F. Kennel, M. Patumeau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wiethoff, C. M., J. G. Smith, G. S. Koe, and C. R. Middaugh. 2001. The potential role of proteoglycans in cationic lipid-mediated gene delivery. Studies of the interaction of cationic lipid-DNA complexes with model glycosaminoglycans. J. Biol. Chem. 276:32806-32813.

Wilson, J. M., L. K. Birinyi, R. N. Salomon, P. Libby, A. D. Callow, and R. C. Mulligan. 1989. Implantation of vascular grafts lined with genetically modified endothelial cells. Science 244:1344-1346.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wu, G. Y. and C. H. Wu. 1988a. Evidence for targeted gene delivery to Hep G2 hepatoma cells in vitro. Biochemistry 27:887-892.

Wu, G. Y. and C. H. Wu. 1988b. Receptor-mediated gene delivery and expression in vivo. J. Biol. Chem. 263:14621-14624.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Xu, J., Z. Nawaz, S. Y. Tsai, M. J. Tsai, and B. W. O'Malley. 1996. The extreme C terminus of progesterone receptor contains a transcriptional repressor domain that functions through a putative corepressor. Proc. Natl. Acad. Sci. USA 93:12195-12199.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J. Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

What is claimed:

1. A method of decreasing body fat proportion in a subject in need thereof, comprising:
   delivering into cells of the subject by direct injection or via electroporation, a nucleic acid expression construct that encodes a growth-hormone-increasing-hormone ("GHRH") or functional biological equivalent thereof, resulting in the expression and secretion of a protein encoded by the nucleic acid expression construct, wherein the encoded GHRH or functional biological equivalent thereof is of formula (SEQ ID NO: 6):

-$X_1$-$X_2$-DAIFTNSYRKVL-$X_3$-QLSARKLLQDI-$X_4$-$X_5$RQQGERNQEQGA-OH wherein the formula has the following characteristics:
   $X_1$ is a D- or L-isomer of the amino acid tyrosine ("Y"), or histidine ("H");
   $X_2$ is a D- or L-isomer of the amino acid alanine ("A"), valine ("V"), or isoleucine ("I");
   $X_3$ is a D- or L-isomer of the amino acid alanine ("A") or glycine ("G");
   $X_4$ is a D- cir L-isomer of the amino acid methionine ("M"), or leucine ("L");
   $X_5$ is a D- cir L-isomer of the amino acid series ("S") or asparagine ("N");
   or a combination thereof;
   and wherein the encoded GHRH or functional biological equivalent thereof facilitates growth hormone ("GH") secretion in the subject.

2. The method of claim 1, wherein delivering into the cells of the subject the nucleic acid expression construct is via electroporation.

3. The method of claim 1, wherein the cells of the subject are somatic cells, or stem cells.

4. The method of claim 1, wherein the nucleic acid expression construct comprises SEQ ID NO: 12.

5. The method of claim 1, wherein the nucleic acid expression construct further comprises a transfection-facilitating polypeptide.

6. The method of claim 5, wherein the transfection-facilitating polypeptide comprises a charged polypeptide.

7. The method of claim 1, wherein the encoded GHRH or functional biological equivalent thereof is expressed in tissue specific cells of the subject.

8. The method of claim 7, wherein the tissue specific cells of the subject comprises muscle cells.

9. The method of claim 1, wherein the encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide.

10. A method for increasing lean body mass a subject in need thereof, comprising the step of: delivering into cells of the subject by direct injection or via electroporation, a nucleic acid expression construct that encodes a growth-hormone-releasing-hormone ("GHRH") or functional biological equivalent thereof, wherein the encoded GHRH or functional biological equivalent thereof is of formula (SEQ ID NO: 6):

-$X_1$-$X_2$-DAIFTNSYRKVL-$X_3$-QLSARKLLQDI-$X_4$-$X_5$RQQGERNQEQGA-OH wherein the formula has the following characteristics:
$X_1$ is a D- or L-isomer of the amino acid tyrosine ("Y"), or histidine ("H");
$X_2$ is a D- or L-isomer of the amino acid alanine ("A"), valine ("V"), or isoleucine ("I");
$X_3$ is a D- or L-isomer of the amino acid alanine ("A") or glycine ("G");
$X_4$ is a D- cir L-isomer of the amino acid methionine ("M"), or leucine ("L");
$X_5$ is a D- cir L-isomer of the amino acid series ("S") or asparagine ("N");
or a combination thereof;
and wherein the encoded GHRH or functional biological equivalent thereof facilitates growth hormone ("GH") secretion in the subject.

11. The method of claim 10, wherein delivering into the cells of the subject the nucleic acid expression construct is via electroporation.

12. The method of claim 10, wherein the cells of the subject are somatic cells, or stem cells.

13. The method of claim 10 wherein the nucleic acid expression construct comprises SEQ ID NO: 12.

14. The method of claim 10, wherein the nucleic acid expression construct further comprises, a transaction-facilitating polypeptide.

15. The method of claim 14, wherein the transfection-facilitating polypeptide comprises a charged polypeptide.

16. The method of claim 10, wherein the encoded GHRH or functional biological equivalent thereof is expressed in tissue specific cells of the subject.

17. The method of claim 10, wherein the encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide.

18. A method for increasing bone density in a subject in need thereof, comprising:
delivering into cells of the subject by direct injection or via electroporation, a nucleic acid expression construct that encodes a growth-hormone-releasing-hormone ("GHRH") or functional biological equivalent thereof, wherein the encoded GHRH or functional biological equivalent thereof is of formula (SEQ ID NO: 6):

-$X_1$-$X_2$-DAIFTNSYRKVL-$X_3$-QLSARKLLQDI-$X_4$-$X_5$RQQGERNQEQGA-OH wherein the formula has the following characteristics:
$X_1$ is a D- or L-isomer of the amino acid tyrosine ("Y"), or histidine ("H");
$X_2$ is a D- or L-isomer of the amino acid alanine ("A"), valine ("V"), or isoleucine ("I");
$X_3$ is a D- or L-isomer of the amino acid alanine ("A") or glycine ("G");
$X_4$ is a D- cir L-isomer of the amino acid methionine ("M"), or leucine ("L");
$X_5$ is a D- cir L-isomer of the amino acid series ("S") or asparagine ("N");
or a combination thereof;

and wherein the encoded GHRH or functional biological equivalent thereof facilitates growth hormone ("GH") secretion in the subject.

19. The method of claim 18, wherein delivering into the cells of the subject the nucleic acid expression construct is via electroporation.

20. The method of claim 18, wherein the cells of the subject are somatic cells, or stem cells.

21. The claim 18, wherein the nucleic acid expression construct comprises SEQ ID NO: 12.

22. The method of claim 18, wherein the nucleic acid expression construct further comprises, a transaction-facilitating polypeptide.

23. The method of claim 22, wherein the transfection-facilitating polypeptide composes a charged polypeptide.

24. The method of claim 18, wherein the encoded GHRH or functional biological equivalent thereof is expressed in tissue specific cells of the subject.

25. The method of claim 24, wherein the tissue specific cells of the subject comprises muscle cells.

26. The method of claim 18, wherein the encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide.

27. A method for increasing a bone healing rate in a subject in need thereof, comprising:
delivering into cells of the subject by direct injection or via electroporation, a nucleic acid expression construct that encodes a growth-hormone-releasing-hormone ("GHRH") or functional biological equivalent thereof, wherein the encoded GHRH or functional biological equivalent thereof is of formula (SEQ ID NO: 6):

-$X_1$-$X_2$-DAIFTNSYRKVL-$X_3$-QLSARKLLQDI-$X_4$-$X_5$RQQGERNQEQGA-OH wherein the formula has the following characteristics:
$X_1$ is a D- or L-isomer of the amino acid tyrosine ("Y"), or histidine ("H");
$X_2$ is a D- or L-isomer of the amino acid alanine ("A"), valine ("V"), or isoleucine ("I");
$X_3$ is a D- or L-isomer of the amino acid alanine ("A") or glycine ("G");
$X_4$ is a D- cir L-isomer of the amino acid methionine ("M"), or leucine ("L");
$X_5$ is a D- cir L-isomer of the amino acid series ("S") or asparagine ("N");
or a combination thereof;
and wherein the encoded GHRH or functional biological equivalent thereof facilitates growth hormone ("GH") secretion in the subject.

28. The method of claim 27, wherein delivering into the cells of the subject the nucleic acid expression construct is via electroporation.

29. The method of claim 27, wherein the cells of the subject are somatic cells, or stem cells.

30. The method of claim 27 for increasing a bone healing, wherein the nucleic acid expression construct comprises SEQ ID NO: 12.

31. The method of claim 27, wherein the nucleic acid expression construct further comprises, a transfection-facilitating polypeptide.

32. The method of claim 31, wherein the transfection-facilitating polypeptide comprises a charged polypeptide.

33. The method of claim 27, wherein the encoded GHRH or functional biological equivalent thereof is expressed in tissue specific cells of the subject.

34. The method of claim 33, wherein the tissue specific cells of the subject comprises muscle cells.

35. The method of claim 27, wherein the encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide.

36. The method of claim 10, further comprising:
applying a cell-transfecting pulse to the tissue; wherein, the cell-transfecting pulse is delivered to an area in the tissue comprising the delivered nucleic acid expression construct.

37. The method of claim 10, further comprising:
placing a plurality of electrodes in the tissue before applying the cell-transfecting pulse to the tissue; wherein the nucleic acid expression construct is delivered to the tissue in an area that interposes the plurality of electrodes.

38. The method of claim 10, wherein the cell-transfecting pulse is an electrical pulse or a vascular pressure pulse.

39. The method of claim 10, wherein the delivering step is by injection, gene gun, or gold particle bombardment.

40. The method of claim 10, wherein the subject is a domesticated animal; a food animal; or a work animal.

41. The method of claim 10, wherein the subject is a human.

42. The method of claim 10, wherein the nucleic acid expression construct is substantially free of a viral backbone.

43. The method of claim 10, wherein a promoter of the nucleic acid expression construct comprises a tissue-specific promoter.

44. The method of claim 10, wherein the tissue-specific promoter comprises a muscle-specific promoter.

45. The construct of claim 10, wherein the promoter comprises SPc5-12 as set forth in SEQ ID NO: 7.

46. The method of claim 10, wherein a 3' untranslated region of the nucleic expression construct is a human growth hormone 3' UTR, bovine growth hormone 3' UTR, or SV40 polyadenylation signal.

47. The method of claim 10, wherein the encoded functional biological equivalent of GHRH is a polypeptide having similar or improved biological activity when compared to the GHRH polypeptide.

48. The method of claim 1, wherein the cells of the subject are muscle cells.

49. The method of claim 1, wherein the nucleic acid expression construct is a plasmid.

50. The method of claim 10, wherein the cells of the subject are muscle cells.

51. The method of claim 10, wherein the nucleic acid expression construct is a plasmid.

52. The method of claim 18, wherein the cells of the subject are muscle cells.

53. The method of claim 18, wherein the nucleic acid expression construct is a plasmid.

54. The method of claim 27, wherein the cells of the subject are muscle cells.

55. The method of claim 27, wherein the nucleic acid expression construct is a plasmid.

* * * * *

SEQUENCE LISTING

```
<160> NUMBER OF SEQ ID NOS: 27

<210> SEQ ID NO 1
<211> LENGTH: 40
<212> TYPE: PRT
<213> ORGANISM: artificial sequence
<220> FEATURE:
<223> OTHER INFORMATION: This is a functional biological equivalent of
      GHRH.

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
<213> ORGANISM: artificial sequence
<220> FEATURE:
<223> OTHER INFORMATION: This is a functional biological equivalent of
      GHRH.

<400> SEQUENCE: 2

Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 3
<211> LENGTH: 40
<212> TYPE: PRT
<213> ORGANISM: artificial sequence
<220> FEATURE:
<223> OTHER INFORMATION: This is a functional biological equivalent of
      GHRH.

<400> SEQUENCE: 3

Tyr Val Asp Ala Ile Phe Thr Asn Ser Tyr Arg Lys Val Leu Ala Gln
1               5                   10                  15
```

```
Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is a functional biological equivalent of
      GHRH.

<400> SEQUENCE: 4

Tyr Ala Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 5
<211> LENGTH: 44
<212> TYPE: PRT
<213> ORGANISM: artificial sequence
<220> FEATURE:
<223> OTHER INFORMATION: This is the artificial sequence for the
      (1-44)NH2

<400> SEQUENCE: 5

Thr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 6
<211> LENGTH: 40
<212> TYPE: PRT
<213> ORGANISM: artificial sequence
<220> FEATURE:
<223> OTHER INFORMATION: This is the artificial sequence for GHRH
      (1-40)OH.
<220> FEATURE:
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
<222> LOCATION: (28)..(28)
<223> OTHER INFORMATION: Xaa at position 28 may be serine or asparagine.
```

<400> SEQUENCE: 6

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Arg Asn Gln Glu Gln Gly Ala
        35                  40

<210> SEQ ID NO 7
<211> LENGTH: 323
<212> TYPE: DNA
<213> ORGANISM: artificial sequence
<220> FEATURE:
<223> OTHER INFORMATION: This is a nucleic acid sequence of a eukaryotic
      promoter c5-12.

<400> SEQUENCE: 7
cggccgtccg ccctcggcac catcctcacg acacccaaat atggcgacgg gtgaggaatg      60
gtggggagtt atttttagag cggtgaggaa ggtgggcagg cagcaggtgt tggcgctcta    120
aaaataactc ccgggagtta tttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323

<210> SEQ ID NO 8
<211> LENGTH: 190
<212> TYPE: DNA
<213> ORGANISM: artificial sequence
<220> FEATURE:
<223> OTHER INFORMATION: Nucleic acid sequence of a hGH poly A tail.

<400> SEQUENCE: 8
gggtggcatc cctgtgaccc ctccccagtg cctctcctgg ccctggaagt tgccactcca      60
gtgcccacca gccttgtcct aataaaatta gttgcatca ttttgtctga ctaggtgtcc    120
ttctataata ttatggggtg agggggggtg gtatggagca aggggcaagt tgggaagaca    180
acctgtaggg                                                           190

<210> SEQ ID NO 9
<211> LENGTH: 219
<212> TYPE: DNA
<213> ORGANISM: artificial sequence
<220> FEATURE:
<223> OTHER INFORMATION: cDNA for Porcine GHRH

<400> SEQUENCE: 9
atggtgctct gggtgttctt ctttgtgatc ctcaccctca gcaacagctc ccactgctcc      60
ccacctcccc ctttgaccct caggatgcgc cggcacgtag atgccatctt caccaacagc    120
taccggaagg tgctggccca gctgtccgcc cgcaagctgc tccaggacat cctgaacagg    180
cagcagggag agaggaacca agagcaagga gcataatga                           219

<210> SEQ ID NO 10
<211> LENGTH: 40
<212> TYPE: PRT
<213> ORGANISM: artificial sequence
<220> FEATURE:
<223> OTHER INFORMATION: amino acid sequence for porcine GHRH.

<400> SEQUENCE: 10

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
            35                  40

<210> SEQ ID NO 11
<211> LENGTH: 3534
<212> TYPE: DNA
<213> ORGANISM: artificial sequence
<220> FEATURE:
<223> OTHER INFORMATION: The operatively linked components of the
      HV-GHRH plasmid.

<400> SEQUENCE: 11
gttgtaaaac gacggccagt gaattgtaat acgactcact atagggcgaa ttggagctcc     60
accgcggtgg cggccgtccg ccctcggcac catcctcacg acacccaaat atggcgacgg    120
gtgaggaatg gtggggagtt attttttagag cggtgaggaa ggtgggcagg cagcaggtgt    180
tggcgctcta aaataactc ccgggagtta tttttagagc ggaggaatgg tggacaccca     240
aatatggcga cggttcctca cccgtcgcca tatttgggtg tccgccctcg gccggggccg    300
cattcctggg ggccgggcgg tgctcccgcc cgcctcgata aaaggctccg ggccggcgg    360 cggcccacga gctacccgga ggagcgggag gcgccaagct ctagaactag tggatcccaa    420
ggcccaactc cccgaaccac tcaggtcct gtggacagtc acctagctg ccatggtgct     480 ctgggtgttc ttctttgtga tcctcaccct cagcaacagc tcccactgct ccccacctcc    540 cccttttgacc ctcaggatgc ggcggcacgt agatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gtttttttgg tagagacggg   1080
gtttcaccat attggccagg ctggtctcca actcctaatc tcaggtgatc tacccacctt   1140
ggcctcccaa attgctggga ttacaggcgt gaaccactgc tcccttccct gtccttctga   1200
ttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga ggggggggccc ggtaccagct   1380 tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
```

| | |
|---|---|
| cagaatcagg ggataacgca ggaaagaaca tgtgagcaaa aggccagcaa aaggccagga | 1800 |
| accgtaaaaa ggccgcgttg ctggcgtttt tccataggct ccgcccccct gacgagcatc | 1860 |
| acaaaaatcg acgctcaagt cagaggtggc gaaacccgac aggactataa agataccagg | 1920 |
| cgtttccccc tggaagctcc ctcgtgcgct ctcctgttcc gaccctgccg cttaccggat | 1980 |
| acctgtccgc ctttctccct tcgggaagcg tggcgcttc tcatagctca cgctgtaggt | 2040 |
| atctcagttc ggtgtaggtc gttcgctcca agctgggctg tgtgcacgaa ccccccgttc | 2100 |
| agcccgaccg ctgcgcctta tccggtaact atcgtcttga gtccaacccg gtaagacacg | 2160 |
| acttatcgcc actggcagca gccactggta acaggattag cagagcgagg tatgtaggcg | 2220 |
| gtgctacaga gttcttgaag tggtggccta actacggcta cactagaaga acagtatttg | 2280 |
| gtatctgcgc tctgctgaag ccagttacct tcggaaaaag agttggtagc tcttgatccg | 2340 |
| gcaaacaaac caccgctggt agcggtggtt tttttgtttg caagcagcag attacgcgca | 2400 |
| gaaaaaaagg atctcaagaa gatcctttga tcttttctac ggggtctgac gctcagaaga | 2460 |
| actcgtcaag aaggcgatag aaggcgatgc gctgcgaatc gggagcggcg ataccgtaaa | 2520 |
| gcacgaggaa gcggtcagcc cattcgccgc caagctcttc agcaatatca cgggtagcca | 2580 |
| acgctatgtc ctgatagcgg tccgccacac ccagccggcc acagtcgatg aatccagaaa | 2640 |
| agcggccatt ttccaccatg atattcggca agcaggcatc gccatgggtc acgacgagat | 2700 |
| cctcgccgtc gggcatgcgc gccttgagcc tggcgaacag ttcggctggc gcgagcccct | 2760 |
| gatgctcttc gtccagatca tcctgatcga caagaccggc ttccatccga gtacgtgctc | 2820 |
| gctcgatgcg atgtttcgct tggtggtcga atgggcaggt agccggatca gcgtatgca | 2880 |
| gccgccgcat tgcatcagcc atgatggata ctttctcggc aggagcaagg tgagatgaca | 2940 |
| ggagatcctg ccccggcact cgcccaata gcagccagtc ccttcccgct tcagtgacaa | 3000 |
| cgtcgagcac agctgcgcaa ggaacgcccg tcgtggccag ccacgatagc cgcgctgcct | 3060 |
| cgtcctgcag ttcattcagg gcaccggaca ggtcggtctt gacaaaaaga accgggcgcc | 3120 |
| cctgcgctga cagccggaac acggcggcat cagagcagcc gattgtctgt tgtgcccagt | 3180 |
| catagccgaa tagcctctcc acccaagcgg ccggagaacc tgcgtgcaat ccatcttgtt | 3240 |
| caatcatgcg aaacgatcct catcctgtct cttgatcaga tcttgatccc ctgcgccatc | 3300 |
| agatccttgg cggcaagaaa gccatccagt ttactttgca gggcttccca accttaccag | 3360 |
| agggcgcccc agctggcaat tccggttcgc ttgctgtcca taaaaccgcc cagtctagca | 3420 |
| actgttggga agggcgatcg gtgcgggcct cttcgctatt acgccagctg gcgaaagggg | 3480 |
| gatgtgctgc aaggcgatta agttgggtaa cgccagggtt ttcccagtca cgac | 3534 |

<210> SEQ ID NO 12
<211> LENGTH: 3534
<212> TYPE: DNA
<213> ORGANISM: artificial sequence
<220> FEATURE:
<223> OTHER INFORMATION: The operatively linked components of the TI-GHRH plasmid.

<400> SEQUENCE: 12

| | |
|---|---|
| gttgtaaaac gacggccagt gaattgtaat acgactcact atagggcgaa ttggagctcc | 60 |
| accgcggtgg cggccgtccg ccctcggcac catcctcacg acacccaaat atggcgacgg | 120 |
| gtgaggaatg gtggggagtt attttttagag cggtgaggaa ggtgggcagg cagcaggtgt | 180 |
| tggcgctcta aaaataactc ccgggagtta ttttttagagc ggaggaatgg tggacaccca | 240 |

```
aatatggcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcaccct cagcaacagc tcccactgct ccccacctcc    540
cccctttgacc ctcaggatgc ggcggtatat cgatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcgggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gttttttgg tagagacggg   1080
gtttcaccat attggccagg ctggtctcca actcctaatc tcaggtgatc tacccacctt   1140
ggcctcccaa attgctggga ttacaggcgt gaaccactgc tcccttccct gtccttctga   1200
ttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga gggggggccc ggtaccagct   1380
tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
cagaatcagg ggataacgca ggaaagaaca tgtgagcaaa aggccagcaa aaggccagga   1800
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagacacg   2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagaaga   2460
actcgtcaag aaggcgatag aaggcgatgc gctgcgaatc gggagcggcg ataccgtaaa   2520
gcacgaggaa gcggtcagcc cattcgccgc caagctcttc agcaatatca cgggtagcca   2580
acgctatgtc ctgatagcgg tccgccacac ccagccggcc acagtcgatg aatccagaaa   2640
```

```
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt ttcccagtca cgac            3534
```

<210> SEQ ID NO 13
<211> LENGTH: 3534
<212> TYPE: DNA
<213> ORGANISM: artificial sequence
<220> FEATURE:
<223> OTHER INFORMATION: The operatively linked components of the
      TV-GHRH plasmid.

<400> SEQUENCE: 13

```
gttgtaaaac gacggccagt gaattgtaat acgactcact atagggcgaa ttggagctcc      60
accgcggtgg cggccgtccg ccctcggcac catcctcacg acacccaaat atggcgacgg     120
gtgaggaatg gtggggagtt attttttagag cggtgaggaa ggtgggcagg cagcaggtgt    180
tggcgctcta aaaataactc ccgggagtta tttttagagc ggaggaatgg tggacaccca    240 aatatgcga cggttcctca cccgtcgcca tatttgggtg tccgccctcg gccggggccg    300
cattcctggg ggcggggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcacccct cagcaacagc tcccactgct ccccaccctcc    540 cccttttgacc ctcaggatgc ggcggtatgt agatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt    1020
tgggattcca ggcatgcatg accaggctca gctaattttt gtttttttgg tagagacggg    1080
gtttcaccat attggccagg ctggtctcca actcctaatc tcaggtgatc tacccacctt    1140
```

```
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga gggggggccc ggtaccagct    1380
tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagacacg    2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca gcgtatgca    2880 gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
```

```
                                              gatgtgctgc aaggcgatta agttgggtaa cgccagggtt ttcccagtca cgac        3534
```

<210> SEQ ID NO 14
<211> LENGTH: 3534
<212> TYPE: DNA
<213> ORGANISM: artificial sequence
<220> FEATURE:
<223> OTHER INFORMATION: The operatively linked components of the
      15/27/28 GHRH plasmid.

<400> SEQUENCE: 14

```
gttgtaaaac gacggccagt gaattgtaat acgactcact atagggcgaa ttggagctcc      60
accgcggtgg cggccgtccg ccctcggcac catcctcacg acacccaaat atggcgacgg     120
gtgaggaatg gtggggagtt attttagag cggtgaggaa ggtgggcagg cagcaggtgt      180
tggcgctcta aaataactc ccgggagtta tttttagagc ggaggaatgg tggacaccca      240
aatatggcga cggttcctca cccgtcgcca tatttgggtg tccgccctcg gccggggccg     300
cattcctggg ggccgggcgg tgctcccgcc cgcctcgata aaaggctccg gggccggcgg     360
cggcccacga gctacccgga ggagcgggag gcgccaagct ctagaactag tggatcccaa     420
ggcccaactc cccgaaccac tcagggtcct gtggacagtc cacctagctg ccatggtgct     480
ctgggtgttc ttctttgtga tcctcaccct cagcaacagc tcccactgct ccccacctcc     540
cccctttgacc ctcaggatgc ggcggtatat cgatgccatc ttcaccaaca gctaccggaa    600
ggtgctggcc cagctgtccg cccgcaagct gctccaggac atcctgaaca gcagcaggg     660
agagaggaac caagagcaag gagcataatg actgcaggaa ttcgatatca agcttatcgg     720
ggtggcatcc ctgtgacccc tccccagtgc ctctcctggc cctggaagtt gccactccag     780
tgcccaccag ccttgtccta ataaaattaa gttgcatcat tttgtctgac taggtgtcct     840
tctataatat tatggggtgg aggggggtgg tatggagcaa ggggcaagtt gggaagacaa     900
cctgtagggc ctgcggggtc tattgggaac caagctggag tgcagtggca caatcttggc     960
tcactgcaat ctccgcctcc tgggttcaag cgattctcct gcctcagcct cccgagttgt    1020
tgggattcca ggcatgcatg accaggctca gctaatttt gttttttgg tagagacggg      1080
gtttcaccat attggccagg ctggtctcca actcctaatc tcaggtgatc tacccacctt    1140
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga gggggggccc ggtaccagct    1380
tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
```

-continued

```
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagcacg     2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt ttttttgtttg caagcagcag attacgcgca   2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt ttcccagtca cgac          3534
```

<210> SEQ ID NO 15
<211> LENGTH: 3534
<212> TYPE: DNA
<213> ORGANISM: artificial sequence
<220> FEATURE:
<223> OTHER INFORMATION: This is the entire plasmid sequence for
      wildtype GHRH.

<400> SEQUENCE: 15

```
gttgtaaaac gacggccagt gaattgtaat acgactcact atagggcgaa ttggagctcc      60
accgcggtgg cggccgtccg ccctcggcac catcctcacg cacccaaat atggcgacgg     120
gtgaggaatg gtgggagtt attttttagag cggtgaggaa ggtgggcagg cagcaggtgt     180
tggcgctcta aaaataactc ccgggagtta tttttagagc ggaggaatgg tggacaccca    240
aatatgcgcga cggttcctca cccgtcgcca tatttgggtg tccgccctcg gccggggccg    300
aatatgcga cggttcctca cccgtcgcca tatttgggtg tccgccctcg gccggggccg     300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
```

-continued

```
ctgggtgttc ttctttgtga tcctcaccct cagcaacagc tcccactgct ccccacctcc    540
cccttttgacc ctcaggatgc ggcggtatgc agatgccatc ttcaccaaca gctaccggaa    600
ggtgctgggc cagctgtccg cccgcaagct gctccaggac atcatgagca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gttttttttgg tagagacggg   1080
gtttcaccat attggccagg ctggtctcca actcctaatc tcaggtgatc tacccacctt   1140
ggcctcccaa attgctggga ttacaggcgt gaaccactgc tcccttccct gtccttctga   1200
ttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga ggggggggccc ggtaccagct   1380
tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
cagaatcagg ggataacgca ggaaagaaca tgtgagcaaa aggccagcaa aaggccagga   1800
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagcacg   2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagaaga   2460
actcgtcaag aaggcgatag aaggcgatgc gctgcgaatc gggagcggcg ataccgtaaa   2520
gcacgaggaa gcggtcagcc cattcgccgc caagctcttc agcaatatca cgggtagcca   2580
acgctatgtc ctgatagcgg tccgccacac ccagccggcc acagtcgatg aatccagaaa   2640
agcggccatt ttccaccatg atattcggca agcaggcatc gccatgggtc acgacgagat   2700
cctcgccgtc gggcatgcgc gccttgagcc tggcgaacag ttcggctggc gcgagcccct   2760
gatgctcttc gtccagatca tcctgatcga caagaccggc ttccatccga gtacgtgctc   2820
gctcgatgcg atgtttcgct tggtggtcga atgggcaggt agccggatca agcgtatgca   2880
```

| | |
|---|---|
| gccgccgcat tgcatcagcc atgatggata ctttctcggc aggagcaagg tgagatgaca | 2940 |
| ggagatcctg ccccggcact tcgcccaata gcagccagtc ccttcccgct tcagtgacaa | 3000 |
| cgtcgagcac agctgcgcaa ggaacgcccg tcgtggccag ccacgatagc cgcgctgcct | 3060 |
| cgtcctgcag ttcattcagg gcaccggaca ggtcggtctt gacaaaaaga accgggcgcc | 3120 |
| cctgcgctga cagccggaac acggcggcat cagagcagcc gattgtctgt tgtgcccagt | 3180 |
| catagccgaa tagcctctcc acccaagcgg ccggagaacc tgcgtgcaat ccatcttgtt | 3240 |
| caatcatgcg aaacgatcct catcctgtct cttgatcaga tcttgatccc ctgcgccatc | 3300 |
| agatccttgg cggcaagaaa gccatccagt ttactttgca gggcttccca accttaccag | 3360 |
| agggcgcccc agctggcaat tccggttcgc ttgctgtcca taaaaccgcc cagtctagca | 3420 |
| actgttggga agggcgatcg gtgcgggcct cttcgctatt acgccagctg gcgaaagggg | 3480 |
| gatgtgctgc aaggcgatta agttgggtaa cgccagggtt ttcccagtca cgac | 3534 |

```
<210> SEQ ID NO 16
<211> LENGTH: 4260
<212> TYPE: DNA
<213> ORGANISM: Artificial sequence
<220> FEATURE:
<223> OTHER INFORMATION: This is the sequence for the pSP-SEAP cDNA
      construct

<400> SEQUENCE: 16
```

| | |
|---|---|
| ggccgtccgc cttcggcacc atcctcacga cacccaaata tggcgacggg tgaggaatgg | 60 |
| tggggagtta tttttagagc ggtgaggaag gtgggcaggc agcaggtgtt ggcgctctaa | 120 |
| aaataactcc cggagttat ttttagagcg gaggaatggt ggacacccaa atatggcgac | 180 |
| ggttcctcac ccgtcgccat atttgggtgt ccgccctcgg ccggggccgc attcctgggg | 240 |
| gccgggcggt gctcccgccc gcctcgataa aaggctccgg ggccggcggc ggcccacgag | 300 |
| ctacccggag gagcgggagg cgccaagctc tagaactagt ggatccccg gctgcagga | 360 |
| attcgatatc aagcttcgaa tcgcgaattc gcccaccatg ctgctgctgc tgctgctgct | 420 |
| gggcctgagg ctacagctct ccctgggcat catcccagtt gaggaggaga acccggactt | 480 |
| ctggaaccgc gaggcagccg aggccctggg tgccgccaag aagctgcagc ctgcacagac | 540 |
| agccgccaag aacctcatca tcttcctggg cgatgggatg ggggtgtcta cggtgacagc | 600 |
| tgccaggatc ctaaaaggg agaagaagga caaactgggg cctgagatac ccctggccat | 660 |
| ggaccgcttc ccatatgtgg ctctgtccaa gacatacaat gtagacaaac atgtgccaga | 720 |
| cagtggagcc acagccacgg cctacctgtg cggggtcaag gcaacttcc agaccattgg | 780 |
| cttgagtgca gccgcccgct ttaaccagtg caacacgaca cgcggcaacg aggtcatctc | 840 |
| cgtgatgaat cgggccaaga agcagggaa gtcagtggga gtggtaacca ccacacgagt | 900 |
| gcagcacgcc tcgccagccg gcacctacgc ccacacggtg aaccgcaact ggtactcgga | 960 |
| cgccgacgtg cctgcctcgg cccgccagga ggggtgccag gacatcgcta cgcagctcat | 1020 |
| ctccaacatg gacattgacg tgatcctagg tggaggccga agtacatgt tcgcatggg | 1080 |
| aaccccagac cctgagtacc cagatgacta cagccaaggt gggaccaggc tggacgggaa | 1140 |
| gaatctggtg caggaatggc tggcgaagcg ccagggtgcc cggtatgtgt ggaaccgcac | 1200 |
| tgagctcatg caggcttccc tggaccccgt tgtgacccat ctcatgggtc tctttgagcc | 1260 |
| tggagacatg aaatacgaga tccaccgaga ctccacactg gaccctccc tgatgggagat | 1320 |
| gacagaggct gccctgcgcc tgctgagcag gaaccccgc ggcttcttcc tcttcgtgga | 1380 |

```
gggtggtcgc atcgaccatg gtcatcatga aagcagggct taccgggcac tgactgagac    1440
gatcatgttc gacgacgcca ttgagagggc gggccagctc accagcgagg aggacacgct    1500
gagcctcgtc actgccgacc actcccacgt cttctccttc ggaggctacc ccctgcgagg    1560
gagctccatc ttcgggctgg cccctggcaa ggcccgggac aggaaggcct acacggtcct    1620
cctatacgga aacggtccag gctatgtgct caaggacggc gcccggccgg atgttaccga    1680
gagcgagagc gggagccccg agtatcggca gcagtcagca gtgcccctgg acgaagagac    1740
ccacgcaggc gaggacgtgg cggtgttcgc gcgcggcccg caggcgcacc tggttcacgg    1800
cgtgcaggag cagaccttca tagcgcacgt catggccttc gccgcctgcc tggagcccta    1860
caccgcctgc gacctggcgc ccccgccgg caccaccgac gccgcgcacc cgggttactc    1920
tagagtcggg gcggccggcc gcttcgagca gacatgataa gatacattga tgagtttgga    1980
caaaccacaa ctagaatgca gtgaaaaaaa tgctttattt gtgaaatttg tgatgctatt    2040
gctttatttg taaccattat aagctgcaat aaacaagtta acaacaacaa ttgcattcat    2100
tttatgtttc aggttcaggg ggaggtgtgg gaggtttttt aaagcaagta aaacctctac    2160
aaatgtggta aaatcgataa ggatccgtcg accgatgccc ttgagagcct tcaacccagt    2220
cagctccttc cggtgggcgc ggggcatgac tatcgtcgcc gcacttatga ctgtcttctt    2280
tatcatgcaa ctcgtaggac aggtgccggc agcgctcttc cgcttcctcg ctcactgact    2340
cgctgcgctc ggtcgttcgg ctgcggcgag cggtatcagc tcactcaaag gcggtaatac    2400
ggttatccac agaatcaggg gataacgcag gaaagaacat gtgagcaaaa ggccagcaaa    2460
aggccaggaa ccgtaaaaag gccgcgttgc tggcgttttt ccataggctc cgcccccctg    2520
acgagcatca caaaaatcga cgctcaagtc agaggtggcg aaacccgaca ggactataaa    2580
gataccaggc gtttccccct ggaagctccc tcgtgcgctc tcctgttccg accctgccgc    2640
ttaccggata cctgtccgcc tttctccctt cgggaagcgt ggcgctttct catagctcac    2700
gctgtaggta tctcagttcg gtgtaggtcg ttcgctccaa gctgggctgt gtgcacgaac    2760
cccccgttca gcccgaccgc tgcgccttat ccggtaacta tcgtcttgag tccaacccgg    2820
taagacacga cttatcgcca ctggcagcag ccactggtaa caggattagc agagcgaggt    2880
atgtaggcgg tgctacagag ttcttgaagt ggtggcctaa ctacggctac actagaagga    2940
cagtatttgg tatctgcgct ctgctgaagc cagttacctt cggaaaaaga gttggtagct    3000
cttgatccgg caaacaaacc accgctggta gcggtggttt ttttgtttgc aagcagcaga    3060
ttacgcgcag aaaaaaagga tctcaagaag atcctttgat cttttctacg gggtctgacg    3120
ctcagtggaa cgaaaactca cgttaaggga ttttggtcat gagattatca aaaaggatct    3180
tcacctagat ccttttaaat taaaaatgaa gttttaaatc aatctaaagt atatatgagt    3240
aaacttggtc tgacagttac caatgcttaa tcagtgaggc acctatctca gcgatctgtc    3300
tatttcgttc atccatagtt gcctgactcc ccgtcgtgta gataactacg atacgggagg    3360
gcttaccatc tggccccagt gctgcaatga taccgcgaga cccacgctca ccggctccag    3420
atttatcagc aataaaccag ccagccggaa gggccgagcg cagaagtggt cctgcaactt    3480
tatccgcctc catccagtct attaattgtt gccgggaagc tagagtaagt agttcgccag    3540
ttaatagttt gcgcaacgtt gttgccattg ctacaggcat cgtggtgtca cgctcgtcgt    3600
ttggtatggc ttcattcagc tccggttccc aacgatcaag gcgagttaca tgatccccca    3660
tgttgtgcaa aaaagcggtt agctccttcg gtcctccgat cgttgtcaga agtaagttgg    3720
```

```
ccgcagtgtt atcactcatg gttatggcag cactgcataa ttctcttact gtcatgccat   3780
ccgtaagatg ctttctgtg  actggtgagt actcaaccaa gtcattctga aatagtgta    3840 tgcggcgacc gagttgctct tgcccggcgt caatacggga taataccgcg ccacatagca   3900
gaactttaaa agtgctcatc attggaaaac gttcttcggg gcgaaaactc tcaaggatct   3960
taccgctgtt gagatccagt tcgatgtaac ccactcgtgc acccaactga tcttcagcat   4020
cttttacttt caccagcgtt tctgggtgag caaaaacagg aaggcaaaat gccgcaaaaa   4080
agggaataag gcgacacgg  aaatgttgaa tactcatact cttcctttt  caatattatt   4140 gaagcattta tcagggttat tgtctcatga gcggatacat atttgaatgt atttagaaaa   4200
ataaacaaat aggggttccg cgcacatttc cccgaaaagt gccacctgac gcgccctgta   4260

<210> SEQ ID NO 17
<211> LENGTH: 2710
<212> TYPE: DNA
<213> ORGANISM: artificial sequence
<220> FEATURE:
<223> OTHER INFORMATION: Plasmid vector having GHRH optimized for mouse.

<400> SEQUENCE: 17
tgtaatacga ctcactatag ggcgaattgg agctccaccg cggtggcggc cgtccgccct     60
cggcaccatc ctcacgacac ccaaatatgg cgacgggtga ggaatggtgg ggagttattt    120
ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctggggcc  gggcggtgct    300 cccgcccgcc tcgataaaag gctccggggc cggcggcggc ccacgagcta cccggaggag    360
cgggaggcgc caagcggatc caaggcccca actccccgaa ccactcaggg tcctgtggac    420
agctcaccta gctgccatgg tgctctgggt gctctttgtg atcctcatcc tcaccagcgg    480
cagccactgc agcctgcctc ccagccctcc cttcaggatg cagaggcacg tggacgccat    540
cttcaccacc aactacagga agctgctgag ccagctgtac gccaggaagg tgatccagga    600
catcatgaac aagcagggcg agaggatcca ggagcagagg gccaggctga gctgataagc    660
ttatcggggt ggcatccctg tgaccccctcc ccagtgcctc tcctggccct ggaagttgcc    720
actccagtgc ccaccagcct tgtcctaata aaattaagtt gcatcatttt gtctgactag    780
gtgtccttct ataatattat ggggtggagg gggtggtat  ggagcaaggg gcaagttggg    840
aagacaacct gtagggctcg agggggggcc cggtaccagc ttttgttccc tttagtgagg    900
gttaatttcg agcttggtct tccgcttcct cgctcactga ctcgctgcgc tcggtcgttc    960
ggctgcggcg agcggtatca gctcactcaa aggcggtaat acggttatcc acagaatcag   1020
gggataacgc aggaaagaac atgtgagcaa aaggccagca aaaggccagg aaccgtaaaa   1080
aggccgcgtt gctggcgttt ttccataggc tccgcccccc tgacgagcat cacaaaaatc   1140
gacgctcaag tcagaggtgg cgaaacccga caggactata agataccag  gcgtttcccc   1200 ctggaagctc cctcgtgcgc tctcctgttc cgacctgcc gcttaccgga tacctgtccg    1260
cctttctccc ttcgggaagc gtggcgcttt ctcatagctc acgctgtagg tatctcagtt   1320
cggtgtaggt cgttcgctcc aagctgggct gtgtgcacga accccccgtt cagcccgacc   1380
gctgcgcctt atccggtaac tatcgtcttg agtccaaccc ggtaagacac gacttatcgc   1440
cactggcagc agccactggt aacaggatta gcagagcgag gtatgtaggc ggtgctacag   1500
agttcttgaa gtggtggcct aactacggct acactagaag aacagtattt ggtatctgcg   1560
```

```
ctctgctgaa gccagttacc ttcggaaaaa gagttggtag ctcttgatcc ggcaaacaaa    1620
ccaccgctgg tagcggtggt ttttttgttt gcaagcagca gattacgcgc agaaaaaaag    1680
gatctcaaga agatcctttg atcttttcta cggggctagc gcttagaaga actcatccag    1740
cagacggtag aatgcaatac gttgagagtc tggagctgca ataccataca gaaccaggaa    1800
acggtcagcc cattcaccac ccagttcctc tgcaatgtca cgggtagcca gtgcaatgtc    1860
ctggtaacgg tctgcaacac ccagacgacc acagtcaatg aaaccagaga acgaccatt     1920 ctcaaccatg atgttcggca ggcatgcatc accatgagta actaccaggt cctcaccatc    1980
cggcatacga gctttcagac gtgcaaacag ttcagccggt gccagaccct gatgttcctc    2040
atccaggtca tcctggtcaa ccagacctgc ttccatacgg gtacgagcac gttcaatacg    2100
atgttttgcc tggtggtcaa acggacaggt agctgggtcc agggtgtgca gacgacgcat    2160
tgcatcagcc atgatagaaa ctttctctgc cggagccagg tgagaagaca gcaggtcctg    2220
acccggaact tcacccagca gcagccagtc acgaccagct tcagtaacta catccagaac    2280
tgcagcacac ggaacaccag tggttgccag ccaagacaga cgagctgctt catcctgcag    2340
ttcattcaga gcaccagaca ggtcagtttt aacaaacaga actggacgac cctgtgcaga    2400
cagacggaaa acagctgcat cagagcaacc aatggtctgc tgtgcccagt cataaccaaa    2460
cagacgttca acccaggctg ccggagaacc tgcatgcaga ccatcctgtt caatcatgcg    2520
aaacgatcct catcctgtct cttgatcaga tcttgatccc ctgcgccatc agatccttgg    2580
cggcaagaaa gccatccagt ttactttgca gggcttccca accttaccag agggcgcccc    2640
agctggcaat tccggttcgc ttgctgtcca taaaaccgcc cagtctagca actgttggga    2700
agggcgatcg                                                          2710
```

<210> SEQ ID NO 18
<211> LENGTH: 2713
<212> TYPE: DNA
<213> ORGANISM: artificial sequence
<220> FEATURE:
<223> OTHER INFORMATION: Plasmid vector having GHRH optimized for rat.

<400> SEQUENCE: 18

```
tgtaatacga ctcactatag ggcgaattgg agctccaccg cggtggcggc cgtccgccct     60
cggcaccatc ctcacgacac ccaaatatgg cgacggtga ggaatggtgg ggagttattt     120
ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctgggggcc gggcggtgct    300
cccgcccgcc tcgataaaag gctccggggc cggcggcggc ccacgagcta cccggaggag    360
cgggaggcgc caagcggatc ccaaggccca actccccgaa ccactcaggg tcctgtggac    420
agctcaccta gctgccatgg ccctgtgggt gttcttcgtg ctgctgaccc tgaccagcgg    480
aagccactgc agcctgcctc ccagccctcc cttcagggtg cgccggcacg ccgacgccat    540
cttcaccagc agctacagga ggatcctggg ccagctgtac gctaggaagc tcctgcacga    600
gatcatgaac aggcagcagg gcgagaggaa ccaggagcag aggagcaggt tcaactgata    660
agcttatcgg ggtggcatcc ctgtgacccc tccccagtgc ctctcctggc cctggaagtt    720
gccactccag tgcccaccag ccttgtccta ataaaattaa gttgcatcat tttgtctgac    780
taggtgtcct tctataatat tatgggtgg aggggggtgg tatggagcaa ggggcaagtt    840
```

```
gggaagacaa cctgtagggc tcgaggggg gcccggtacc agcttttgtt cccttagtg       900 agggttaatt tcgagcttgg tcttccgctt cctcgctcac tgactcgctg cgctcggtcg       960
ttcggctgcg gcgagcggta tcagctcact caaaggcggt aatacggtta tccacagaat      1020
caggggataa cgcaggaaag aacatgtgag caaaaggcca gcaaaaggcc aggaaccgta      1080
aaaaggccgc gttgctggcg tttttccata ggctccgccc ccctgacgag catcacaaaa      1140
atcgacgctc aagtcagagg tggcgaaacc cgacaggact ataaagatac caggcgtttc      1200
cccctggaag ctccctcgtg cgctctcctg ttccgaccct gccgcttacc ggatacctgt      1260
ccgcctttct cccttcggga agcgtggcgc tttctcatag ctcacgctgt aggtatctca      1320
gttcggtgta ggtcgttcgc tccaagctgg gctgtgtgca cgaaccccc gttcagcccg      1380 accgctgcgc cttatccggt aactatcgtc ttgagtccaa cccggtaaga cacgacttat      1440
cgccactggc agcagccact ggtaacagga ttagcagagc gaggtatgta ggcggtgcta      1500
cagagttctt gaagtggtgg cctaactacg gctacactag aagaacagta tttggtatct      1560
gcgctctgct gaagccagtt accttcggaa aaagagttgg tagctcttga tccggcaaac      1620
aaaccaccgc tggtagcggt ggtttttttg tttgcaagca gcagattacg cgcagaaaaa      1680
aaggatctca agaagatcct ttgatctttt ctacggggct agcgcttaga agaactcatc      1740
cagcagacgg tagaatgcaa tacgttgaga gtctggagct gcaataccat acagaaccag      1800
gaaacggtca gcccattcac cacccagttc ctctgcaatg tcacgggtag ccagtgcaat      1860
gtcctggtaa cggtctgcaa cacccagacg accacagtca atgaaaccag agaaacgacc      1920
attctcaacc atgatgttcg gcaggcatgc atcaccatga gtaactacca ggtcctcacc      1980
atccggcata cgagctttca gacgtgcaaa cagttcagcc ggtgccagac cctgatgttc      2040
ctcatccagg tcatcctggt caaccagacc tgcttccata cgggtacgag cacgttcaat      2100
acgatgtttt gctggtggt caaacggaca ggtagctggg tccagggtgt gcagacgacg      2160
cattgcatca gccatgatag aaactttctc tgccggagcc aggtgagaag acagcaggtc      2220
ctgacccgga acttcaccca gcagcagcca gtcacgacca gcttcagtaa ctacatccag      2280
aactgcagca cacggaacac cagtggttgc cagccaagac agacgagctg cttcatcctg      2340
cagttcattc agagcaccag acaggtcagt tttaacaaac agaactggac gaccctgtgc      2400
agacagacgg aaaacagctg catcagagca accaatggtc tgctgtgccc agtcataacc      2460
aaacagacgt tcaacccagg ctgccggaga acctgcatgc agaccatcct gttcaatcat      2520
gcgaaacgat cctcatcctg tctcttgatc agatcttgat cccctgcgcc atcagatcct      2580
tggcggcaag aaagccatcc agtttacttt gcagggcttc ccaaccttac cagagggcgc      2640
cccagctggc aattccggtt cgcttgctgt ccataaaacc gcccagtcta gcaactgttg      2700
ggaagggcga tcg                                                        2713
```

<210> SEQ ID NO 19
<211> LENGTH: 2716
<212> TYPE: DNA
<213> ORGANISM: artificial sequence
<220> FEATURE:
<223> OTHER INFORMATION: Plasmid vector having GHRH optimized for bovine.

<400> SEQUENCE: 19

```
ccaccgcgt ggcggccgtc cgccctcggc accatcctca cgacacccaa atatggcgac         60
gggtgaggaa tggtggggag ttatttttag agcggtgagg aaggtgggca ggcagcaggt        120
```

```
gttggcgctc taaaaataac tcccgggagt tatttttaga gcggaggaat ggtggacacc      180
caaatatggc gacggttcct cacccgtcgc catatttggg tgtccgccct cggccggggc      240
cgcattcctg ggggccgggc ggtgctcccg cccgcctcga taaaaggctc cggggccggc      300
ggcggcccac gagctacccg gaggagcggg aggcgccaag cggatcccaa ggcccaactc      360
cccgaaccac tcagggtcct gtggacagct cacctagctg ccatggtgct gtgggtgttc      420
ttcctggtga ccctgaccct gagcagcgga agccacggca gcctgccag ccagcccctg       480 aggatcccta ggtacgccga cgccatcttc accaacagct acaggaagat cctgggccag      540
ctgagcgcta ggaagctcct gcaggacatc atgaacagg agcagggcga gaggaaccag       600
gagcagggcg cctgataagc ttatcggggt ggcatccctg tgaccctcc ccagtgcctc       660 tcctggccct ggaagttgcc actccagtgc ccaccagcct tgtcctaata aaattaagtt      720
gcatcatttt gtctgactag gtgtccttct ataatattat ggggtggagg gggtggtat       780 ggagcaaggg gcaagttggg aagacaacct gtagggctcg agggggggcc cggtaccagc      840
ttttgttccc tttagtgagg gttaatttcg agcttggtct tccgcttcct cgctcactga      900
ctcgctgcgc tcggtcgttc ggctgcggcg agcggtatca gctcactcaa aggcggtaat      960
acggttatcc acagaatcag gggataacgc aggaaagaac atgtgagcaa aaggccagca     1020
aaaggccagg aaccgtaaaa aggccgcgtt gctggcgttt ttccataggc tccgcccccc     1080
tgacgagcat cacaaaaatc gacgctcaag tcagaggtgg cgaaacccga caggactata     1140
aagataccag gcgtttcccc ctggaagctc cctcgtgcgc tctcctgttc cgaccctgcc     1200
gcttaccgga tacctgtccg cctttctccc ttcgggaagc gtggcgcttt ctcatagctc     1260
acgctgtagg tatctcagtt cggtgtaggt cgttcgctcc aagctgggct gtgtgcacga     1320
accccccgtt cagcccgacc gctgcgcctt atccggtaac tatcgtcttg agtccaaccc     1380
ggtaagacac gacttatcgc cactggcagc agccactggt aacaggatta gcagagcgag     1440
gtatgtaggc ggtgctacag agttcttgaa gtggtggcct aactacggct acactagaag     1500
aacagtattt ggtatctgcg ctctgctgaa gccagttacc ttcggaaaaa gagttggtag     1560
ctcttgatcc gacaaacaaa ccaccgctgg tagcggtggt ttttttgttt gcaagcagca     1620
gattacgcgc agaaaaaaag gatctcaaga agatcctttg atcttttcta cggggtctga     1680
cgctcagcta gcgctcagaa gaactcgtca agaaggcgat agaaggcgat gcgctgcgaa     1740
tcgggagcgg cgataccgta aagcacgagg aagcggtcag cccattcgcc gccaagctct     1800
tcagcaatat cacgggtagc caacgctatg tcctgatagc ggtccgccac acccagccgg     1860
ccacagtcga tgaatccaga aaagcggcca ttttccacca tgatattcgg caagcaggca     1920
tcgccatgag tcacgacgag atcctcgccg tcgggcatgc gcgccttgag cctggcgaac     1980
agttcggctg gcgcgagccc ctgatgctct tcgtccagat catcctgatc gacaagaccg     2040
gcttccatcc gagtacgtgc tcgctcgatg cgatgtttcg cttggtggtc gaatgggcag     2100
gtagccggat caagcgtatg cagccgccgc attgcatcag ccatgatgga ctttctcg       2160 gcaggagcaa ggtgagatga caggagatcc tgccccggca cttcgcccaa tagcagccag     2220
tcccttcccg cttcagtgac aacgtcgagc acagctgcgc aaggaacgcc cgtcgtggcc     2280
agccacgata gccgcgctgc ctcgtcctgc agttcattca gggcaccgga caggtcggtc     2340
ttgacaaaaa gaaccgggcg cccctgcgct gacagccgga acacggcggc atcagagcag     2400
ccgattgtct gttgtgccca gtcatagccg aatagcctct ccacccaagc ggccggagaa     2460
cctgcgtgca atccatcttg ttcaatcatg cgaaacgatc ctcatcctgt ctcttgatca     2520
```

```
gatcttgatc ccctgcgcca tcagatcctt ggcggcaaga aagccatcca gtttactttg    2580
cagggcttcc aaccttacc agagggcgcc ccagctggca attccggttc gcttgctgtc      2640
cataaaaccg cccagtctag caactgttgg gaagggcgat cgtgtaatac gactcactat    2700
agggcgaatt ggagct                                                    2716

<210> SEQ ID NO 20
<211> LENGTH: 2716
<212> TYPE: DNA
<213> ORGANISM: artificial sequence
<220> FEATURE:
<223> OTHER INFORMATION: Plasmid vector having GHRH optimized for ovine.

<400> SEQUENCE: 20
ccaccgcggt ggcggccgtc cgccctcggc accatcctca cgacacccaa atatggcgac     60
gggtgaggaa tggtgggag ttattttag agcggtgagg aaggtgggca ggcagcaggt      120
gttggcgctc taaaaataac tcccgggagt tattttaga gcggaggaat ggtggacacc    180
caaatatggc gacggttcct cacccgtcgc catatttggg tgtccgccct cggccggggc    240
cgcattcctg ggggccgggc ggtgctcccg cccgcctcga taaaaggctc cggggccggc   300
ggcggcccac gagctacccg gaggagcggg aggcgccaag cggatcccaa ggcccaactc   360
cccgaaccac tcagggtcct gtggacagct cacctagctg ccatggtgct gtgggtgttc   420
ttcctggtga ccctgaccct gagcagcgga agccacggca gcctgccag ccagcccctg    480 aggatcccta ggtacgccga cgccatcttc accaacagct acaggaagat cctgggccag   540
ctgagcgcta ggaagctcct gcaggacatc atgaacaggc agcagggcga aggaaccag    600 gagcagggcg cctgataagc ttatcggggt ggcatccctg tgacccctcc ccagtgcctc   660
tcctggccct ggaagttgcc actccagtgc ccaccagcct tgtcctaata aaattaagtt   720
gcatcatttt gtctgactag gtgtccttct ataatattat ggggtggagg gggtggtat   780 ggagcaaggg gcaagttggg aagacaacct gtagggctcg aggggggcc cggtaccagc   840 ttttgttccc tttagtgagg gttaatttcg agcttggtct tccgcttcct cgctcactga   900
ctcgctgcgc tcggtcgttc ggctgcggcg agcggtatca gctcactcaa aggcggtaat   960
acggttatcc acagaatcag gggataacgc aggaaagaac atgtgagcaa aaggccagca  1020
aaaggccagg aaccgtaaaa aggccgcgtt gctggcgttt ttccataggc tccgcccccc  1080
tgacgagcat cacaaaaatc gacgctcaag tcagaggtgg cgaaacccga caggactata  1140
aagataccag gcgtttcccc ctggaagctc cctcgtgcgc tctcctgttc cgaccctgcc  1200
gcttaccgga tacctgtccg cctttctccc ttcgggaagc gtggcgcttt ctcatagctc  1260
acgctgtagg tatctcagtt cggtgtaggt cgttcgctcc aagctgggct gtgtgcacga  1320 acccccgtt cagcccgacc gctgcgcctt atccggtaac tatcgtcttg agtccaaccc  1380
ggtaagacac gacttatcgc cactggcagc agccactggt aacaggatta gcagagcgag  1440
gtatgtaggc ggtgctacag agttcttgaa gtggtggcct aactacggct acactagaag  1500
aacagtattt ggtatctgcg ctctgctgaa gccagttacc ttcggaaaaa gagttggtag  1560
ctcttgatcc gacaaacaaa ccaccgctgg tagcggtggt ttttttgttt gcaagcagca  1620
gattacgcgc agaaaaaaag gatctcaaga agatcctttg atcttttcta cggggtctga  1680
cgctcagcta cgctcagaa gaactcgtca agaaggcgat agaaggcgat gcgctgcgaa  1740
tcgggagcgg cgataccgta aagcacgagg aagcggtcag cccattcgcc gccaagctct  1800
```

```
tcagcaatat cacgggtagc caacgctatg tcctgatagc ggtccgccac acccagccgg    1860
ccacagtcga tgaatccaga aaagcggcca ttttccacca tgatattcgg caagcaggca    1920
tcgccatgag tcacgacgag atcctcgccg tcgggcatgc gcgccttgag cctggcgaac    1980
agttcggctg gcgcgagccc ctgatgctct tcgtccagat catcctgatc gacaagaccg    2040
gcttccatcc gagtacgtgc tcgctcgatg cgatgtttcg cttggtggtc gaatgggcag    2100
gtagccggat caagcgtatg cagccgccgc attgcatcag ccatgatgga tactttctcg    2160
gcaggagcaa ggtgagatga caggagatcc tgccccggca cttcgcccaa tagcagccag    2220
tcccttcccg cttcagtgac aacgtcgagc acagctgcgc aaggaacgcc cgtcgtggcc    2280
agccacgata gccgcgctgc ctcgtcctgc agttcattca gggcaccgga caggtcggtc    2340
ttgacaaaaa gaaccgggcg cccctgcgct gacagccgga acacggcggc atcagagcag    2400
ccgattgtct gttgtgccca gtcatagccg aatagcctct ccacccaagc ggccggagaa    2460
cctgcgtgca atccatcttg ttcaatcatg cgaaacgatc ctcatcctgt ctcttgatca    2520
gatcttgatc ccctgcgcca tcagatcctt ggcggcaaga aagccatcca gtttactttg    2580
cagggcttcc caaccttacc agagggcgcc ccagctggca attccggttc gcttgctgtc    2640
cataaaaccg cccagtctag caactgttgg gaagggcgat cgtgtaatac gactcactat    2700
agggcgaatt ggagct                                                   2716

<210> SEQ ID NO 21
<211> LENGTH: 2713
<212> TYPE: DNA
<213> ORGANISM: artificial sequence
<220> FEATURE:
<223> OTHER INFORMATION: Plasmid vector having GHRH optimized for
      chicken.

<400> SEQUENCE: 21
tgtaatacga ctcactatag ggcgaattgg agctccaccg cggtggcggc cgtccgccct      60
cggcaccatc ctcacgacac ccaaatatgg cgacgggtga ggaatggtgg ggagttatt     120 ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctgggggcc gggcggtgct    300
cccgcccgcc tcgataaaag gctccggggc cggcggcggc ccacgagcta cccggaggag    360
cgggaggcgc caagcggatc ccaaggccca actccccgaa ccactcaggg tcctgtggac    420
agctcaccta gctgccatgg ccctgtgggt gttctttgtg ctgctgaccc tgacctccgg    480
aagccactgc agcctgccac ccagcccacc cttccgcgtc aggcgccacg ccgacggcat    540
cttcagcaag gcctaccgca agctcctggg ccagctgagc gcacgcaact acctgcacag    600
cctgatggcc aagcgcgtgg gcagcggact gggagacgag gccgagcccc tgagctgata    660
agcttatcgg ggtggcatcc ctgtgacccc tccccagtgc ctctcctggc cctggaagtt    720
gccactccag tgcccaccag ccttgtccta ataaaattaa gttgcatcat tttgtctgac    780
taggtgtcct tctataatat tatgggtggg aggggggtgg tatggagcaa ggggcaagtt    840
gggaagacaa cctgtagggc tcaggggggg cccggtacc agcttttgtt cccttttagtg    900 agggttaatt tcgagcttgg tcttccgctt cctcgctcac tgactcgctg cgctcggtcg    960
ttcggctgcg gcgagcggta tcagctcact caaaggcggt aatacggtta tccacagaat    1020
caggggataa cgcaggaaag aacatgtgag caaaaggcca gcaaaggcc aggaaccgta    1080
```

```
aaaaggccgc gttgctggcg ttttttccata ggctccgccc ccctgacgag catcacaaaa    1140
atcgacgctc aagtcagagg tggcgaaacc cgacaggact ataaagatac caggcgtttc    1200
cccctggaag ctccctcgtg cgctctcctg ttccgaccct gccgcttacc ggatacctgt    1260
ccgcctttct cccttcggga agcgtggcgc tttctcatag ctcacgctgt aggtatctca    1320
gttcggtgta ggtcgttcgc tccaagctgg gctgtgtgca cgaaccccccc gttcagcccg    1380 accgctgcgc cttatccggt aactatcgtc ttgagtccaa cccggtaaga cacgacttat    1440
cgccactggc agcagccact ggtaacagga ttagcagagc gaggtatgta ggcggtgcta    1500
cagagttctt gaagtggtgg cctaactacg gctacactag aagaacagta tttggtatct    1560
gcgctctgct gaagccagtt accttcggaa aaagagttgg tagctcttga tccggcaaac    1620
aaaccaccgc tggtagcggt ggtttttttg tttgcaagca gcagattacg cgcagaaaaa    1680
aaggatctca agaagatcct ttgatctttt ctacggggct agcgcttaga agaactcatc    1740
cagcagacgg tagaatgcaa tacgttgaga gtctggagct gcaataccat acagaaccag    1800
gaaacggtca gcccattcac cacccagttc ctctgcaatg tcacgggtag ccagtgcaat    1860
gtcctggtaa cggtctgcaa cacccagacg accacagtca atgaaaccag agaaacgacc    1920
attctcaacc atgatgttcg gcaggcatgc atcaccatga gtaactacca ggtcctcacc    1980
atccggcata cgagctttca gacgtgcaaa cagttcagcc ggtgccagac cctgatgttc    2040
ctcatccagg tcatcctggt caaccagacc tgcttccata cgggtacgag cacgttcaat    2100
acgatgtttt gctggtggt caaacggaca ggtagctggg tccagggtgt gcagacgacg    2160
cattgcatca gccatgatag aaactttctc tgccggagcc aggtgagaag acagcaggtc    2220
ctgacccgga acttcaccca gcagcagcca gtcacgacca gcttcagtaa ctacatccag    2280
aactgcagca cacggaacac cagtggttgc cagccaagac agacgagctg cttcatcctg    2340
cagttcattc agagcaccag acaggtcagt tttaacaaac agaactggac gaccctgtgc    2400
agacagacgg aaaacagctg catcagagca accaatggtc tgctgtgccc agtcataacc    2460
aaacagacgt caacccagg ctgccggaga acctgcatgc agaccatcct gttcaatcat    2520
gcgaaacgat cctcatcctg tctcttgatc agatcttgat ccccctgcgcc atcagatcct    2580 tggcggcaag aaagccatcc agtttacttt gcagggcttc ccaaccttac cagagggcgc    2640
cccagctggc aattccggtt cgcttgctgt ccataaaacc gcccagtcta gcaactgttg    2700
ggaagggcga tcg    2713
```

<210> SEQ ID NO 22
<211> LENGTH: 55
<212> TYPE: DNA
<213> ORGANISM: artificial sequence
<220> FEATURE:
<223> OTHER INFORMATION: Nucleic acid sequence of hGH" 5' UTR.

<400> SEQUENCE: 22

```
caaggcccaa ctccccgaac cactcagggt cctgtggaca gctcacctag ctgcc    55
```

<210> SEQ ID NO 23
<211> LENGTH: 782
<212> TYPE: DNA
<213> ORGANISM: artificial sequence
<220> FEATURE:
<223> OTHER INFORMATION: Sequence of a plasmid pUC-18 origin of
      replicaition

<400> SEQUENCE: 23

-continued

```
tcttccgctt cctcgctcac tgactcgctg cgctcggtcg ttcggctgcg gcgagcggta    60
tcagctcact caaaggcggt aatacggtta tccacagaat caggggataa cgcaggaaag   120
aacatgtgag caaaaggcca gcaaaaggcc aggaaccgta aaaaggccgc gttgctggcg   180 ttttccata ggctccgccc ccctgacgag catcacaaaa atcgacgctc aagtcagagg    240
tggcgaaacc cgacaggact ataaagatac caggcgtttc ccctggaag ctccctcgtg    300 cgctctcctg ttccgaccct gccgcttacc ggatacctgt ccgcctttct cccttcggga   360
agcgtggcgc tttctcatag ctcacgctgt aggtatctca gttcggtgta ggtcgttcgc   420
tccaagctgg gctgtgtgca cgaacccccc gttcagcccg accgctgcgc cttatccggt   480
aactatcgtc ttgagtccaa cccggtaaga cacgacttat cgccactggc agcagccact   540
ggtaacagga ttagcagagc gaggtatgta ggcggtgcta cagagttctt gaagtggtgg   600
cctaactacg gctacactag aaggacagta tttggtatct gcgctctgct gaagccagtt   660
accttcggaa aaagagttgg tagctcttga tccggcaaac aaaccaccgc tggtagcggt   720
ggtttttttg tttgcaagca gcagattacg cgcagaaaaa aaggatctca agaagatcct   780
tt                                                                  782
```

<210> SEQ ID NO 24
<211> LENGTH: 5
<212> TYPE: DNA
<213> ORGANISM: artificial sequence
<220> FEATURE:
<223> OTHER INFORMATION: This is a NEO ribosomal binding site.

<400> SEQUENCE: 24

```
tcctc                                                                 5
```

<210> SEQ ID NO 25
<211> LENGTH: 29
<212> TYPE: DNA
<213> ORGANISM: artificial sequence
<220> FEATURE:
<223> OTHER INFORMATION: Nucleic acid sequence of a prokaryotic PNEO
      promoter.

<400> SEQUENCE: 25

```
accttaccag agggcgcccc agctggcaa                                      29
```

<210> SEQ ID NO 26
<211> LENGTH: 3558
<212> TYPE: DNA
<213> ORGANISM: artificial sequence
<220> FEATURE:
<223> OTHER INFORMATION: Sequence for the inducible pGR1774 containing
      GHRH.

<400> SEQUENCE: 26

```
atgcctggag acgccatcca cgctgttttg acctccatag aagacaccgg gaccgatcca    60
gcctccgcgg ccgggaacgg tgcattggaa cgcggattcc ccgtgttaat taacaggtaa   120
gtgtcttcct cctgtttcct tcccctgcta ttctgctcaa ccttcctatc agaaactgca   180
gtatctgtat ttttgctagc agtaatacta acggttcttt ttttctcttc acaggccacc   240
atgtagaact agtgatccca aggcccaact ccccgaacca ctcagggtcc tgtggacagc   300
tcacctagct gccatggtgc tctgggtgtt cttctttgtg atcctcaccc tcagcaacag   360
ctcccactgc tccccacctc ccccttgac cctcaggatg cggcggtatg cagatgccat    420
cttcaccaac agctaccgga aggtgctggg ccagctgtcc gcccgcaagc tgctccagga   480
```

-continued

```
catcatgagc aggcagcagg gagagagcaa ccaagagcga ggagcataat gactgcagga    540
attcgatatc aagcttatcg gggtggcatc cctgtgaccc ctccccagtg cctctcctgg    600
ccctggaagt tgccactcca gtgcccacca gccttgtcct aataaaatta agttgcatca    660
ttttgtctga ctaggtgtcc ttctataata ttatggggtg gagggggggtg gtatggagca    720 aggggcaagt tggaagacaa acctgtaggg cctgcgggt  ctattgggaa ccaagctgga    780
gtgcagtggc acaatcttgg ctcactgcaa tctccgcctc ctgggttcaa gcgattctcc    840
tgcctcagcc tcccgagttg ttgggattcc aggcatgcat gaccaggctc agctaatttt    900 tgttttttg  gtagagacgg ggtttcacca tattggccag gctggtctcc aactcctaat    960
ctcaggtgat ctacccacct tggcctccca aattgctggg attacaggcg tgaaccactg   1020
ctcccttccc tgtccttctg attttaaaat aactatacca gcaggaggac gtccagacac   1080
agcataggct acctggccat gcccaaccgg tgggacattt gagttgcttg cttggcactg   1140
tcctctcatg cgttgggtcc actcagtaga tgcctgttga attcgatacc gtcgacctcg   1200
agggggggcc cggtaccagc ttttgttccc tttagtgagg gttaatttcg agcttggcgt   1260
aatcatggtc atagctgttt cctgtgtgaa attgttatcc gctcacaatt ccacacaaca   1320
tacgagccgg aagcataaag tgtaaagcct ggggtgccta atgagtgagc taactcacat   1380
taattgcgtt gcgctcactg cccgctttcc agtcggaaaa cctgtcgtgc cagctgcatt   1440
aatgaatcgg ccaacgcgcg gggagaggcg gtttgcgtat tgggcgctct tccgcttcct   1500
cgctcactga ctcgctgcgc tcggtcgttc ggctgcggcg agcggtatca gctcactcaa   1560
aggcggtaat acggttatcc acagaatcag gggataacgc aggaaagaac atgtgagcaa   1620
aaggccagca aaaggccagg aaccgtaaaa aggccgcgtt gctggcgttt ttccataggc   1680
tccgcccccc tgacgagcat cacaaaaatc gacgctcaag tcagaggtgg cgaaacccga   1740
caggactata aagataccag gcgtttcccc ctggaagctc cctcgtgcgc tctcctgttc   1800
cgaccctgcc gcttaccgga tacctgtccg cctttctccc ttcgggaagc gtggcgcttt   1860
ctcatagctc acgctgtagg tatctcagtt cggtgtaggt cgttcgctcc aagctgggct   1920
gtgtgcacga accccccgtt cagcccgacc gctgcgcctt atccggtaac tatcgtcttg   1980
agtccaaccc ggtaagacac gacttatcgc cactggcagc agccactggt aacaggatta   2040
gcagagcgag gtatgtaggc ggtgctacag agttcttgaa gtggtggcct aactacggct   2100
acactagaag aacagtattt ggtatctgcg ctctgctgaa gccagttacc ttcggaaaaa   2160
gagttggtag ctcttgatcc ggcaaacaaa ccaccgctgg tagcggtggt ttttttgttt   2220
gcaagcagca gattacgcgc agaaaaaaag gatctcaaga agatcctttg atcttttcta   2280
cggggtctga cgctcagaag aactcgtcaa gaaggcgata aaggcgatg  cgctgcgaat   2340 cgggagcggc gataccgtaa agcacgagga agcggtcagc ccattcgccg ccaagctctt   2400
cagcaatatc acgggtagcc aacgctatgt cctgatagcg gtccgccaca cccagccggc   2460
cacagtcgat gaatccagaa aagcggccat tttccaccat gatattcggc aagcaggcat   2520
cgccatgggt cacgacgaga tcctcgccgt cgggcatgcg cgccttgagc ctggcgaaca   2580
gttcggctgg cgcgagcccc tgatgctctt cgtccagatc atcctgatcg acaagaccgg   2640
cttccatycg agtacgtgct cgctcgatgc gatgtttcgc ttggtggtcg aatgggcagg   2700
tagccggatc aagcgtatgc agccgccgca ttgcatcagc catgatggat actttctcgg   2760
caggagcaag gtgagatgac aggagatcct gccccggcac ttcgcccaat agcagccagt   2820
```

```
cccttcccgc ttcagtgaca acgtcgagca cagctgcgca aggaacgccc gtcgtggcca    2880
gccacgatag ccgcgctgcc tcgtcctgca gttcattcag ggcaccggac aggtcggtct    2940
tgacaaaaag aaccgggcgc ccctgcgctg acagccggaa cacggcggca tcagagcagc    3000
cgattgtctg ttgtgcccag tcatagccga atagcctctc acccaagcg gccggagaac     3060 ctgcgtgcaa tccatcttgt tcaatcatgc gaaacgatcc tcatcctgtc tcttgatcag    3120
atcttgatcc cctgcgccat cagatccttg gcggcaagaa agccatccag tttactttgc    3180
agggcttccc aaccttacca gagggcgccc cagctggcaa ttccggttcg cttgctgtcc    3240
ataaaaccgc ccagtctagc aactgttggg aagggcgatc ggtgcgggcc tcttcgctat    3300
tacgccagct ggcgaaaggg ggatgtgctg caaggcgatt aagttgggta acgccagggt    3360
tttcccagtc acgacgttgt aaaacgacgg ccagtgaatt gtaatacgac tcactatagg    3420
gcgaattaat tcgagcttgc atgcctgcag gtcgaagcg gagtactgtc ctccgagtgg     3480
agtactgtcc tccgagcgga gtactgtcct ccgagtcgag ggtcgaagcg gagtactgtc    3540
ctccgagtgg agtactgt                                                  3558
```

```
<210> SEQ ID NO 27
<211> LENGTH: 4855
<212> TYPE: DNA
<213> ORGANISM: artificial Sequence
<220> FEATURE:
<223> OTHER INFORMATION: Sequence for the muscle-specific GeneSwitch
      plasmid, pGS1633

<400> SEQUENCE: 27
```

```
agggccgct ctagctagag tctgcctgcc ccctgcctgg cacagcccgt acctggccgc      60
acgctccctc acaggtgaag ctcgaaaact ccgtccccgt aaggagcccc gctgcccccc    120
gaggcctcct ccctcacgcc tcgctgcgct cccggctccc gcacggccct gggagaggcc    180
cccaccgctt cgtccttaac gggccggcg gtgccggggg attatttcgg ccccggcccc     240 ggggggggccc ggcagacgct ccttatacgg cccggcctcg ctcacctggg ccgcggccag   300
gagcgccttc tttgggcagc gccgggccgg ggccgcgccg ggcccgacac ccaaatatgg    360
cgacggccgg ggccgcattc ctgggggccg ggcggtgctc ccgcccgcct cgataaaagg    420
ctccggggcc ggcgggcgac tcagatcgcc tggagacgcc atccacgctg ttttgacctc    480
catagaagac accgggaccg atccagcctc cgcggccggg aacggtgcat tggaacgcgg    540
attccccgtg ttaattaaca ggtaagtgtc ttcctcctgt ttccttcccc tgctattctg    600
ctcaaccttc ctatcagaaa ctgcagtatc tgtattttg ctagcagtaa tactaacggt     660
tctttttttc tcttcacagg ccaccaagct accggtccac catggactcc cagcagccag    720
atctgaagct actgtcttct atcgaacaag catgcgatat ttgccgactt aaaaagctca    780
agtgctccaa agaaaaaccg aagtgcgcca agtgtctgaa gaacaactgg gagtgtcgct    840
actctcccaa aaccaaaagg tctccgctga ctagggcaca tctgacagaa gtggaatcaa    900
ggctagaaag actggaacag ctatttctac tgatttttcc tcgagaccag aaaaagttca    960
ataaagtcag agttgtgaga gcactggatg ctgttgctct cccacagcca gtgggcgttc   1020
caaatgaaag ccaagcccta agccagagat tcacttttc accaggtcaa gacatacagt   1080
tgattccacc actgatcaac ctgttaatga gcattgaacc agatgtgatc tatgcaggac   1140
atgacaacac aaaacctgac acctccagtt ctttgctgac aagtcttaat caactaggcg   1200
agaggcaact tctttcagta gtcaagtggg ctaaatcatt gccaggtttt cgaaacttac   1260
```

-continued

```
atattgatga ccagataact ctcattcagt attcttggat gagcttaatg gtgtttggtc    1320
taggatggag atcctacaaa cacgtcagtg ggcagatgct gtattttgca cctgatctaa    1380
tactaaatga acagcggatg aaagaatcat cattctattc attatgcctt accatgtggc    1440
agatcccaca ggagtttgtc aagcttcaag ttagccaaga agagttcctc tgtatgaaag    1500
tattgttact tcttaataca attcctttgg aagggctacg aagtcaaacc cagtttgagg    1560
agatgaggtc aagctacatt agagagctca tcaaggcaat tggtttgagg caaaaaggag    1620
ttgtgtcgag ctcacagcgt ttctatcaac ttacaaaact tcttgataac ttgcatgatc    1680
ttgtcaaaca acttcatctg tactgcttga atacattat ccagtcccgg gcactgagtg    1740
ttgaatttcc agaaatgatg tctgaagtta ttgctgggtc gacgcccatg gaattccagt    1800
acctgccaga tacagacgat cgtcaccgga ttgaggagaa acgtaaaagg acatatgaga    1860
ccttcaagag catcatgaag aagagtcctt tcagcggacc caccgacccc cggcctccac    1920
ctcgacgcat tgctgtgcct tcccgcagct cagcttctgt ccccaagcca gcacccagc    1980 cctatccctt tacgtcatcc ctgagcacca tcaactatga tgagtttccc accatggtgt    2040
ttccttctgg gcagatcagc caggcctcgg ccttggcccc ggcccctccc caagtcctgc    2100
cccaggctcc agcccctgcc cctgctccag ccatggtatc agctctggcc caggccccag    2160
ccctgtcccc agtcctagcc ccaggccctc ctcaggctgt ggccccacct gcccccaagc    2220
ccacccaggc tggggaagga acgctgtcag aggccctgct gcagctgcag tttgatgatg    2280
aagacctggg ggccttgctt ggcaacagca cagacccagc tgtgttcaca gacctggcat    2340
ccgtcgacaa ctccgagttt cagcagctgc tgaaccaggg catacctgtg ccccccaca    2400 caactgagcc catgctgatg gagtaccctg aggctataac tcgcctagtg acaggggccc    2460
agaggccccc cgacccagct cctgctccac tgggggcccc ggggctcccc aatggcctcc    2520
tttcaggaga tgaagacttc tcctccattg cggacatgga cttctcagcc ctgctgagtc    2580
agatcagctc ctaaggatcc tccggactag aaaagccgaa ttctgcagga attgggtggc    2640
atccctgtga cccctcccca gtgcctctcc tggccctgga agttgccact ccagtgccca    2700
ccagccttgt cctaataaaa ttaagttgca tcattttgtc tgactaggtg tccttctata    2760
atattatggg gtggagggg gtggtatgga gcaagggca agttgggaag acaacctgta    2820
gggctcgagg gggggcccgg taccagcttt tgttcccttt agtgagggtt aatttcgagc    2880
ttggcgtaat catggtcata gctgtttcct gtgtgaaatt gttatccgct cacaattcca    2940
cacaacatac gagccggaag cataaagtgt aaagcctggg gtgcctaatg agtgagctaa    3000
ctcacattaa ttgcgttgcg ctcactgccc gctttccagt cgggaaacct gtcgtgccag    3060
ctgcattaat gaatcggcca acgcgcgggg agaggcggtt tgcgtattgg gcgctcttcc    3120
gcttcctcgc tcactgactc gctgcgctcg gtcgttcggc tgcggcgagc ggtatcagct    3180
cactcaaagg cggtaatacg gttatccaca gaatcagggg ataacgcagg aaagaacatg    3240
tgagcaaaag gccagcaaaa ggccaggaac cgtaaaaagg ccgcgttgct ggcgtttttc    3300
cataggctcc gcccccctga cgagcatcac aaaaatcgac gctcaagtca gaggtggcga    3360
aacccgacag gactataaag ataccaggcg tttccccctg gaagctccct cgtgcgctct    3420
cctgttccga ccctgccgct taccggatac ctgtccgcct ttctcccttc gggaagcgtg    3480
gcgctttctc atagctcacg ctgtaggtat ctcagttcgg tgtaggtcgt tcgctccaag    3540
ctgggctgtg tgcacgaacc ccccgttcag cccgaccgct gcgccttatc cggtaactat    3600
cgtcttgagt ccaacccggt aagacacgac ttatcgccac tggcagcagc cactggtaac    3660
```

```
aggattagca gagcgaggta tgtaggcggt gctacagagt tcttgaagtg gtggcctaac    3720
tacggctaca ctagaaggac agtatttggt atctgcgctc tgctgaagcc agttaccttc    3780
ggaaaaagag ttggtagctc ttgatccggc aaacaaacca ccgctggtag cggtggtttt    3840
tttgtttgca agcagcagat tacgcgcaga aaaaaaggat ctcaagaaga tcctttgatc    3900
ttttctacgg ggtctgacgc tcagaagaac tcgtcaagaa ggcgatagaa ggcgatgcgc    3960
tgcgaatcgg gagcggcgat accgtaaagc acgaggaagc ggtcagccca ttcgccgcca    4020
agctcttcag caatatcacg ggtagccaac gctatgtcct gatagcggtc cgccacaccc    4080
agccggccac agtcgatgaa tccagaaaag cggccatttt ccaccatgat attcggcaag    4140
caggcatcgc catgcgtcac gacgagatcc tcgccgtcgg gcatgcgcgc cttgagcctg    4200
gcgaacagtt cggctggcgc gagcccctga tgctcttcgt ccagatcatc ctgatcgaca    4260
agaccggctt ccatccgagt acgtgctcgc tcgatgcgat gtttcgcttg gtggtcgaat    4320
gggcaggtag ccggatcaag cgtatgcagc cgccgcattg catcagccat gatggatact    4380
ttctcggcag gagcaaggtg agatgacagg agatcctgcc ccggcacttc gcccaatagc    4440
agccagtccc ttcccgcttc agtgacaacg tcgagcacag ctgcgcaagg aacgcccgtc    4500
gtggccagcc acgatagccg cgctgcctcg tcctgcagtt cattcagggc accggacagg    4560
tcggtcttga caaaaagaac cgggcgcccc tgcgctgaca gccggaacac ggcggcatca    4620
gagcagccga ttgtctgttg tgcccagtca tagccgaata gcctctccac ccaagcggcc    4680
ggagaacctg cgtgcaatcc atcttgttca atcatgcgaa acgatcctca tcctgtctct    4740
tgatcagatc ttgatcccct gcgccatcag atccttggcg gcaagaaagc catccagttt    4800
actttgcagg gcttcccaac cttaccagag ggcgaattcg agcttgcatg cctgc         4855
```